(12) United States Patent
Soleta et al.

(10) Patent No.: US 7,799,571 B2
(45) Date of Patent: Sep. 21, 2010

(54) CONTROL OF N-(PHOSPHONOMETHYL)IMINODIACETIC ACID CONVERSION IN MANUFACTURE OF GLYPHOSATE

(75) Inventors: Donald D. Soleta, St. Louis, MO (US); David R. Eaton, St. Louis, MO (US); Peter E. Rogers, St. Louis, MO (US); Eduardo A. Casanova, Chesterfield, MO (US); John Wagenknecht, Cedar Hill, MO (US); Leonard Aynardi, St. Louis, MO (US); David Z. Becher, St. Louis, MO (US); Robert E. Byrd, Columbia, IL (US); James P. Coleman, Maryland Heights, MO (US); Walter K. Gavlick, Chesterfield, MO (US); Eric A. Haupfear, St. Charles, MO (US); Oliver Lerch, Eureka, MO (US); Carl Mumford, Tuscola, IL (US); Alfredo Oba, Sao Jose dos Campos (BR); Stephen D. Prosch, Ballwin, MO (US); Bart Roose, Melson (BE); Mark D. Scaia, St. Louis, MO (US); Lowell R. Smith, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/910,146

(22) PCT Filed: Apr. 3, 2006

(86) PCT No.: PCT/US2006/012214
§ 371 (c)(1), (2), (4) Date: Jun. 20, 2008

(87) PCT Pub. No.: WO2006/107824
PCT Pub. Date: Oct. 12, 2006

(65) Prior Publication Data
US 2009/0011515 A1 Jan. 8, 2009

Related U.S. Application Data

(60) Provisional application No. 60/667,783, filed on Apr. 1, 2005.

(51) Int. Cl.
*G01N 33/00* (2006.01)
(52) U.S. Cl. .......................... 436/104; 436/171; 562/17
(58) Field of Classification Search .................... None
See application file for complete search history.

(56) References Cited

U.S. PATENT DOCUMENTS 3,835,000 A 9/1974 Frazier et al.

(Continued)

FOREIGN PATENT DOCUMENTS

GB 1428499 3/1976

(Continued)

OTHER PUBLICATIONS

Written Opinion issued in International Application No. PCT/US2006/012214 dated Dec. 21, 2006, 19 pages.
International Search Report issued in International Application No. PCT/US2006/012214 dated Dec. 21, 2006, 4 pages.

*Primary Examiner*—Yelena G Gakh
*Assistant Examiner*—David Weisz
(74) *Attorney, Agent, or Firm*—Senniger Powers LLP; Joseph A. Schaper

(57) ABSTRACT

This invention relates to the preparation of N-(phosphonomethyl)glycine ("glyphosate") from N-(phosphonomethyl)iminodiacetic acid ("PMIDA"), and more particularly to methods for control of the conversion of PMIDA, for the identification of reaction end points relating to PMIDA conversion and the preparation of glyphosate products having controlled PMIDA content.

10 Claims, 20 Drawing Sheets

U.S. PATENT DOCUMENTS

| | | | |
|---|---|---|---|
| 4,624,937 A | 11/1986 | Chou | |
| 5,043,475 A | 8/1991 | Fields, Jr. | |
| 5,077,431 A | 12/1991 | Fields, Jr. | |
| 5,087,740 A | 2/1992 | Smith | |
| 5,095,140 A | 3/1992 | Fields, Jr. | |
| 5,137,834 A | 8/1992 | Repasi | |
| 5,948,938 A | 9/1999 | Nakano et al. | |
| 6,365,772 B1 | 4/2002 | Cullen et al. | |
| 6,417,133 B1 | 7/2002 | Ebner et al. | |
| 6,586,621 B2 | 7/2003 | Leiber et al. | |
| 6,603,039 B1 | 8/2003 | Ebner et al. | |
| 6,818,450 B2 | 11/2004 | Eaton et al. | |
| 6,956,005 B2 | 10/2005 | Leiber | |
| 6,963,009 B2 | 11/2005 | Leiber et al. | |
| 7,015,351 B2 | 3/2006 | Haupfear et al. | |
| 2002/0068836 A1 | 6/2002 | Haupfear et al. | |
| 2002/0197725 A1 | 12/2002 | Eaton et al. | |
| 2004/0010160 A1 | 1/2004 | Coleman et al. | |
| 2005/0059840 A1 | 3/2005 | Haupfear et al. | |
| 2005/0176989 A1 | 8/2005 | Coleman et al. | |
| 2006/0020143 A1 | 1/2006 | Leiber | |
| 2006/0106248 A1 | 5/2006 | Scaia et al. | |
| 2006/0229466 A1 | 10/2006 | Arhancet et al. | |

FOREIGN PATENT DOCUMENTS

| | | | |
|---|---|---|---|
| WO | 9638455 A1 | 12/1996 | |
| WO | 0009517 A2 | 2/2000 | |
| WO | 03068387 A1 | 8/2003 | |
| WO | 2005016519 A1 | 2/2005 | |
| WO | 2006031938 A2 | 3/2006 | |
| WO | 2006107824 A3 | 10/2006 | |

VOLTAGE SIGNAL -------- CURRENT SIGNAL ———

CONTROL OF N-(PHOSPHONOMETHYL)IMINODIACETIC ACID CONVERSION IN MANUFACTURE OF GLYPHOSATE

CROSS-REFERENCE TO RELATED APPLICATIONS

This application is a United States national stage application based on International Application No. PCT/US2006/012214, filed Apr. 3, 2006, and claims the benefit of U.S. provisional application Ser. No. 60/667,783, filed Apr. 1, 2005.

BACKGROUND OF THE INVENTION

This invention relates to the preparation of N-(phosphonomethyl)glycine ("glyphosate") from N-(phosphonomethyl)iminodiacetic acid ("PMIDA"), and more particularly to methods for control of the conversion of PMIDA, for the identification of reaction end points relating to PMIDA conversion and the preparation of glyphosate products having controlled PMIDA content.

N-(phosphonomethyl)glycine, known in the agricultural chemical art as glyphosate, is a highly effective and commercially important broad spectrum phytotoxicant useful in controlling the growth of germinating seeds, emerging seedlings, maturing and established woody and herbaceous vegetation, and aquatic plants. Glyphosate is used as a post-emergent herbicide to control the growth of a wide variety of annual and perennial grass and broadleaf weed species in cultivated crop lands, including cotton production, and is the active ingredient in the ROUNDUP family of herbicides available from Monsanto Company (Saint Louis, Mo.).

Glyphosate and salts thereof are conveniently applied in aqueous herbicidal formulations, usually containing one or more surfactants, to the foliar tissues (i.e., the leaves or other photosynthesizing organs) of the target plant. After application, the glyphosate is absorbed by the foliar tissues and translocated throughout the plant. Glyphosate noncompetitively blocks an important biochemical pathway that is common to virtually all plants. More specifically, glyphosate inhibits the shikimic acid pathway that leads to the biosynthesis of aromatic amino acids. Glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS) found in plants.

Various commercial processes are available for the preparation of glyphosate. For example, glyphosate may be produced by the catalytic oxidation of PMIDA in an aqueous medium. Such reaction may be conducted in either a batch or continuous mode in the presence of a catalyst that typically comprises particulate carbon, or a noble metal such as Pt on a carbon support. The catalyst is typically slurried in an aqueous solution of PMIDA within a stirred tank reactor, and molecular oxygen introduced into the reactor to serve as the oxidant. The reaction is exothermic. Temperature of the reactor is conventionally controlled by transfer of heat from the reaction mixture to a cooling fluid in an indirect heat exchanger. The heat exchanger may comprise coils immersed in the reaction mixture within the reactor, a jacket on the exterior of the reactor, or an external heat exchanger through which the reaction mixture is circulated from the reactor.

Recovery of the glyphosate product typically comprises one or more crystallization steps. The mother liquor stream or streams obtained in the crystallization may be recycled to crystallization or reaction steps of the process. A fraction of the mother liquor(s) is generally removed from the process in order to purge by-products. Crystallized glyphosate may be dried and sold as a solid crystalline product. A substantial fraction of the glyphosate crystals are commonly neutralized with a base such as isopropylamine, KOH, etc. in an aqueous medium to produce a concentrated salt solution. A concentrated formulation comprising such glyphosate salt solution, and often also other components such as, for example, various surfactants, is a principal product of commerce.

It is desirable to achieve substantially complete conversion of PMIDA to glyphosate during the course of the reaction. Although some unreacted PMIDA can be recovered and recycled to the reaction system, there are unavoidable losses that translate into loss of yield. The quality of the glyphosate product may also be compromised by residual PMIDA that is not removed in the glyphosate product recovery system.

Processes have been proposed by which the reaction can be deliberately conducted only to partial conversion, and the resulting relatively large fraction of unreacted PMIDA separated from the reaction mixture and recycled to the reaction system. However, processes which require the recycle of a high fraction of PMIDA involve capital intensive recovery and recycle systems, and require relatively complicated schemes for removal of impurities. As a consequence, it is often preferred to conduct the oxidation reaction to a high conversion, in some instances to a substantial extinction of PMIDA.

However, it is not desirable to extend the reaction time so as to unnecessarily expose the product glyphosate to the acidic and oxidative conditions of the aqueous reaction system. Glyphosate itself is subject to oxidation to form the by-product aminomethylphosphonic acid ("AMPA"). Relatively extended and/or severe reaction conditions can be effective to drive the conversion of PMIDA to glyphosate, but can also cause a loss of glyphosate yield by further conversion of glyphosate to AMPA. Extending the reaction cycle also increases the potential for loss of yield in the formation of N-methylglyphosate ("NMG") by reaction of by-product formaldehyde or formaldehyde and formic acid with glyphosate. Other impurities such as N-formylglyphosate ("NFG"), N-methylaminomethylphosphonic acid ("MAMPA") and glycine may also be formed. All these impurities and by-products may also potentially compromise the quality of the glyphosate product.

Consequently, there is a need in the art for methods for monitoring the conversion of PMIDA to glyphosate, and more particularly for identifying an end point at which, or residence time over which, a target conversion (target residual PMIDA concentration) has been attained. A PMIDA content up to about 6000 ppm by weight, basis glyphosate in the ultimate glyphosate product is typical of commercial production. In a product recovery process comprising crystallization of glyphosate such as that described, e.g., in U.S. Application Publication No. US 2005/0059840 A1, expressly incorporated herein by reference, the PMIDA content of the glyphosate product can be maintained at less than 6000 ppm if the PMIDA content of the product reaction solution is not greater than about 2500 ppm on a glyphosate basis.

SUMMARY OF THE INVENTION

The present invention provides multiple modifications and improvements in a process for preparing glyphosate by the catalytic oxidation of PMIDA. Process modifications are disclosed which provide for the preparation of a glyphosate product having a relatively low PMIDA content. Certain of these modifications comprise selection and control of reaction conditions to produce a product reaction solution of glyphosate which has a lower PMIDA content than has been achieved in normal practice. Further in accordance with the invention, various methods are disclosed for monitoring the conversion of PMIDA in the catalytic oxidation reaction, for detecting an end point of a batch oxidation reaction, for determining an appropriate residence time in a continuous oxidation reaction, and/or for selecting and controlling reaction conditions for the production of a reaction product having a relatively low residual PMIDA content.

Briefly, therefore, in several of its aspects, the present invention is directed to a process for the preparation of glyphosate comprising oxidation of PMIDA or a salt thereof. The process comprises contacting PMIDA with an oxidizing agent in an aqueous reaction medium within an oxidation reaction zone in the presence of a catalyst for the oxidation, thereby effecting oxidation of PMIDA and producing a reaction solution comprising glyphosate or another intermediate which can be converted to glyphosate.

In various embodiments, the reaction solution is further processed to produce a glyphosate product containing not more than about 600 ppm PMIDA or salt thereof; and in certain of these embodiments, the oxidation of PMIDA in the aqueous reaction medium is continued until the concentration of PMIDA in the reaction medium has been reduced to a terminal concentration such that product recovery or other further processing yields a glyphosate product comprising not greater than about 600 ppm by weight PMIDA, basis glyphosate.

The invention is further directed to a method of supplying a glyphosate product for applications in which it is desirable to maintain the PMIDA content of the product at consistently less than about 0.06 wt. % on a glyphosate basis. In accordance with the method, glyphosate is produced in a manufacturing facility by a process which comprises catalytic oxidation of PMIDA in an aqueous medium within an oxidation reaction zone in the presence of a catalyst for the oxidation. During designated operations within the facility, the process is conducted under conditions effective to consistently produce a glyphosate product having a PMIDA content less than about 0.06 wt. %, basis glyphosate. The product produced during such designated operations is segregated from other glyphosate product produced during other operations wherein the other glyphosate product has an PMIDA content greater than about 0.06 wt. %, basis glyphosate.

The invention is further directed to various methods for monitoring or detecting the conversion of PMIDA to glyphosate or another intermediate for glyphosate in the course of the catalytic oxidation of PMIDA in an aqueous reaction medium within an oxidation reaction zone.

One such method comprises obtaining a series of Fourier transform infrared ("FTIR") analyses of the PMIDA content of the aqueous reaction medium or a sample thereof during the course of the reaction. A target conversion of PMIDA is identified for oxidation of PMIDA to glyphosate or another intermediate for glyphosate, and/or by a target residual N-(phosphonomethyl)iminodiacetic acid content. From a plurality of FTIR analyses, a projection is made of the batch reaction time or continuous oxidation residence time within the oxidation reaction zone at which said target conversion or end point may be anticipated to be attained.

In another method for estimating PMIDA conversion or residual PMIDA content, a potential is applied between a working electrode and another electrode immersed in the aqueous reaction medium or a sample thereof. Measurement is made of a function of the power consumed in maintaining a select current density, or a select potential difference between the electrodes.

According to a still further method for monitoring or detecting the conversion of PMIDA to glyphosate or another intermediate for glyphosate in the course of the catalytic oxidation of PMIDA in an aqueous reaction medium within an oxidation reaction zone, the exothermic heat generated in the oxidation reaction is measured; and the proportion of PMIDA that has been converted to glyphosate or another intermediate in the reaction zone is estimated by a method comprising comparing the heat generated in the reaction zone with the mass of PMIDA charged to the reaction zone and the exothermic heat of reaction for the oxidation of PMIDA to glyphosate or another glyphosate intermediate.

In particular applications, the instantaneous rate of exothermic heat generated in the oxidation reaction zone is monitored during conversion of PMIDA to glyphosate or the another intermediate for glyphosate; and the residual concentration of PMIDA in the aqueous reaction medium within the reaction zone is estimated by a method comprising comparing the rate of exothermic heat generation with the mass of aqueous medium containing PMIDA that is charged to the reaction zone or a function thereof. In a particular application of this method, the rate of heat generation is measured under conditions of non-zero order oxidation of PMIDA to glyphosate.

Another method for monitoring or detecting the conversion of PMIDA to glyphosate or another intermediate for glyphosate in the course of the catalytic oxidation of PMIDA in an aqueous reaction medium within an oxidation reaction zone comprises measuring the generation of carbon dioxide in the reaction zone; and the proportion of PMIDA that has been converted to glyphosate or another intermediate in reaction zone is estimated by a method comprising comparing the carbon dioxide generated in the reaction zone with the mass of PMIDA charged to the reaction zone and the unit carbon dioxide generation obtained from the oxidation of PMIDA to glyphosate or the other intermediate for glyphosate. The estimate of conversion is made either on the basis of cumulative $CO_2$ generation, instantaneous $CO_2$ generation, or a combination thereof. In a particular application, the instantaneous rate of $CO_2$ generation is measured under conditions of non-zero order reaction.

In a PMIDA oxidation reaction wherein the oxidizing agent comprises molecular oxygen, the conversion of PMIDA to glyphosate and the residual PMIDA concentration can also be estimated from the cumulative consumption of oxygen or the instantaneous rate of oxygen consumption during the reaction. In certain advantageous embodiments the instantaneous rate of oxygen consumption is measured under conditions of non-zero order reaction.

In various applications of the method wherein the oxygen consumption are tracked, the method is otherwise similar to or substantially the same as that described above with respect to FTIR.

In further embodiments of the invention, the residual PMIDA concentration or extent of conversion can be monitored by following the dissolved oxygen content or oxidation/reduction potential of the aqueous reaction medium wherein the oxidation of PMIDA takes place, or the $CO_2$ content of the vent gas from the reaction zone. Where the oxidizing agent comprises molecular oxygen, the progress of the conversion or the residual PMIDA concentration may be determined from the $O_2$ content of the vent gas. A high conversion and/or reaction end point is typically indicated by an increase in the $O_2$ content or a decrease in the $CO_2$ content of the vent gas; or by an increase in the dissolved oxygen content of the aqueous reaction medium.

In a still further embodiment of the invention, a series of chromatographic analyses of the PMIDA content of the aqueous reaction medium are obtained during the course of the oxidation reaction and a target conversion of PMIDA and/or a target end point defined by a target residual PMIDA concentration is identified and the series of chromatographic analyses used to project the batch reaction time or continuous oxidation residence time at which the target conversion or end point may be anticipated to be attained. In another embodiment for monitoring or detecting the conversion of PMIDA to glyphosate or another intermediate for glyphosate in the course of the catalytic oxidation of PMIDA in an aqueous reaction medium within an oxidation reaction zone, the aminomethylphosphonic acid content of the aqueous reaction medium is monitored and used to determine the conversion of PMIDA or identify an endpoint of the oxidation reaction.

The various methods of the invention for monitoring conversion, detecting or projecting a reaction end point, and/or detecting residual PMIDA concentration may be used in combination. Any two or more of the disclosed methods can be combined. For example, a particular method may provide a cross check of one or more of the others or otherwise provide a basis for refining the estimate obtained from another method or combination of other methods.

As further disclosed herein, the methods for monitoring conversion can be integrated into a programmed process control scheme based on an algorithm that may be based on historical operating and analytical data, and which can be updated by on-line or off-line analytical data in combination with current or historical measurement of various process parameters, including but not limited to those that form the specific basis for the estimates of conversion.

DESCRIPTION OF THE PREFERRED EMBODIMENTS

Figure 1:
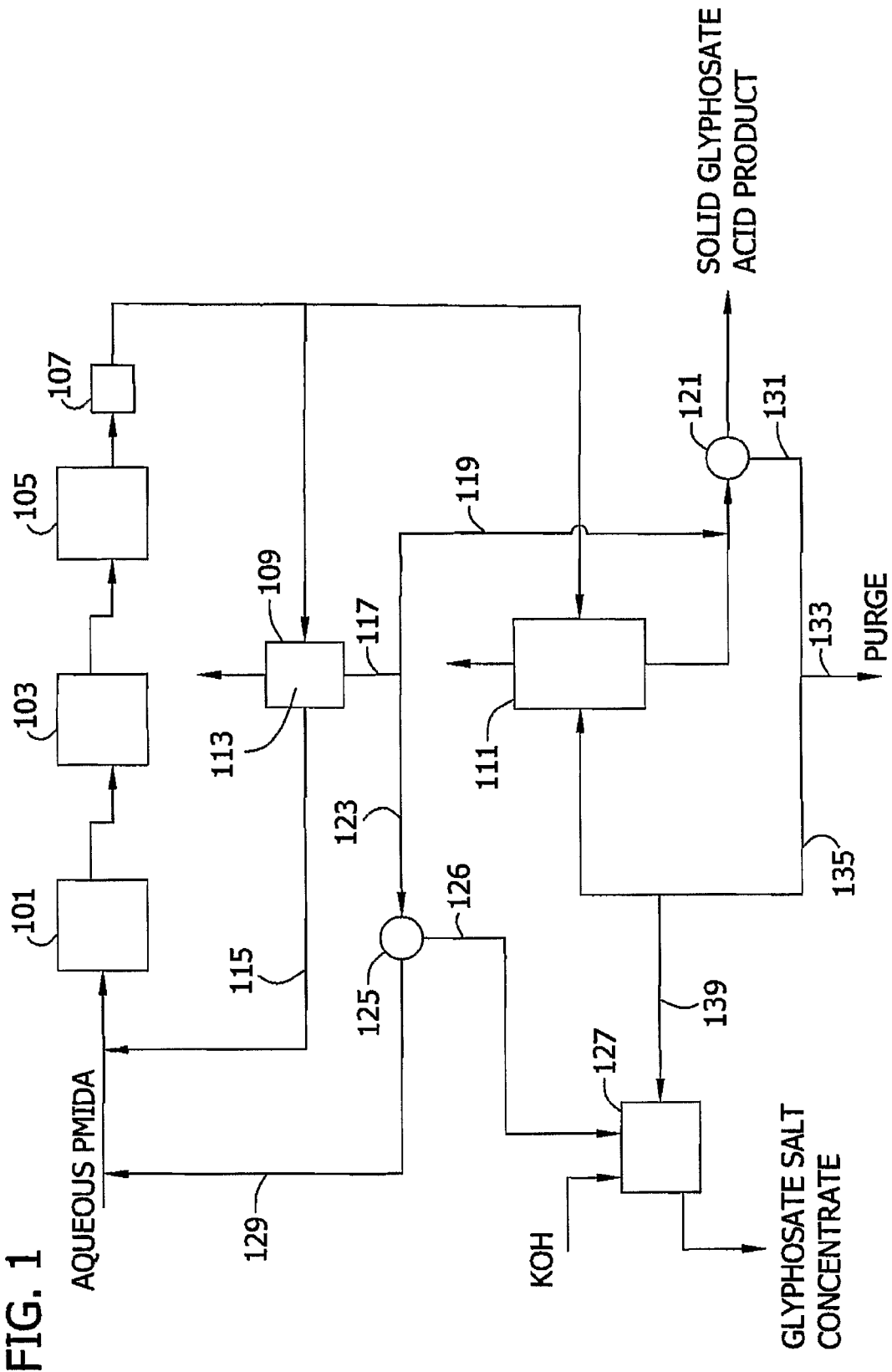
FIG. 1 is a schematic flow sheet illustrating a continuous process for the manufacture of glyphosate from PMIDA, in which the modifications of the present invention for production of a low PMIDA content glyphosate product may be implemented.

In a preferred process for the manufacture of glyphosate, an aqueous solution of N-(phosphonomethyl)iminodiacetic acid ("PMIDA") is contacted with an oxidizing agent in the presence of a catalyst. The catalyst may be, for example, a particulate activated carbon as described in Chou U.S. Pat. No. 4,624,937, a noble metal on carbon catalyst as described in Ebner et al. U.S. Pat. No. 6,417,133, or a transition metal/nitrogen composition on carbon catalyst as described in U.S. Application Publication No. US 2004/0010160 A1; International Publication No. WO 2005/016519 A1; and copending and co-assigned U.S. application Ser. No. 11/357,900, filed Feb. 17, 2006, entitled TRANSITION METAL-CONTAINING CATALYSTS AND CATALYST COMBINATIONS INCLUDING TRANSITION METAL-CONTAINING CATALYSTS AND PROCESSES FOR THEIR PREPARATION AND USE AS OXIDATION CATALYSTS, all of which are expressly incorporated herein by reference.

Conventionally, the oxidation reaction is conducted in one or more stirred tank reactors wherein the catalyst is slurried in an aqueous solution of PMIDA. The reactor(s) may be operated in either a batch or continuous mode. Where the reaction is conducted in a continuous mode, the aqueous reaction medium may be caused to flow through a fixed bed comprising a catalyst for the oxidation, or through a plurality of continuous stirred tank reactors ("CSTRs") in series. The oxidizing agent is preferably molecular oxygen, though other oxidants such as, for example, hydrogen peroxide or ozone, may also be used. Where molecular oxygen is used, the reaction is conveniently conducted at a temperature in the range from about 70° C. to about 140° C., more typically in the range from about 80° C. to about 120° C. Where a particulate noble metal catalyst is used, it is typically slurried in the reaction solution at a concentration of from about 0.5% to about 5% by weight.

In a series of CSTRS, the temperature of each reactor is independently controlled, but typically each reactor is operated in substantially the same temperature range as the other(s). Preferably, the temperature is controlled at a level that maintains glyphosate in solution and achieves substantial oxidation of by-product formaldehyde and formic acid, without excessive formation of either by-product iminodiacetic acid ("IDA"), which typically results from oxidation of PMIDA, or by-product aminomethylphosphonic acid ("AMPA"), which typically results from oxidation of glyphosate. Formation of each of these by-products generally tends to increase with temperature, with IDA formation occurring principally in the first or second reactor where PMIDA concentration is highest, and AMPA being formed principally in the last or penultimate reactor where glyphosate concentration is relatively high. Where the oxidant is molecular oxygen, it may be introduced independently into one or more, preferably all, of the series of CSTRs. Typically, the oxygen pressure may be in the range of about 15 to about 300 psig, more typically in the range of about 40 to about 150 psig. Where CSTRs are arranged for cascaded flow without intermediate transfer pumps, the pressure in each successive CSTR is preferably lower than the pressure in the immediately preceding CSTR so as to assure a positive differential for promoting forward flow. Typically, oxygen pressure in the first of a series of CSTRs is operated at a level approximating its pressure vessel rating, while each of the remaining reactors in the series are operated at a pressure that is within its rating, but also sufficiently below the pressure prevailing in the immediately preceding reactor to ensure forward flow. For example, in a system comprising three such reactors in series, the first reactor might be operated at a pressure in the range of from about 105 to about 125 psig, the second reactor at from about 85 to about 100 psig and the third reactor at about 60 to about 80 psig.

A process comprising a series of CSTRs for manufacture of glyphosate is illustrated in FIG. 1. Catalytic oxidation of PMIDA is conducted in a series of CSTRs 101 to 105 in each of which an aqueous solution of PMIDA is contacted with molecular oxygen in the presence of a particulate catalyst slurried in the aqueous reaction medium. A reaction mixture or slurry exiting the final CSTR 105 is directed to a catalyst filter 107 wherein particulate catalyst is removed for recycle to the reaction system. For recovery of glyphosate product, filtered reaction solution is divided between a vacuum crystallizer 109, typically operated without substantial heat input (i.e., substantially adiabatically) and an evaporative crystallizer 111 wherein water is driven off the aqueous phase by transfer heat from a heat transfer fluid such as steam. A crystallization slurry 113 produced in vacuum crystallizer 109 is allowed to settle, and the supernatant mother liquor 115, which contains some unreacted PMIDA, is decanted and may be recycled to the reaction system, typically to CSTR 101. A solid technical grade glyphosate may be recovered from the underflow slurry 117 exiting the decantation step. According to the optional process alternative illustrated in FIG. 1, the concentrated vacuum crystallizer slurry 117 underflowing from the decantation is divided into two fractions. One fraction 119 is mixed with the crystal slurry exiting the evaporative crystallizer 111 and directed to a centrifuge 121 which separates a solid crystalline technical grade glyphosate acid product that may be used or sold in the form of a solid wet centrifuge cake or after the centrifuge cake has been dried in a conventional manner. The other vacuum crystallizer underflow slurry fraction 123 is directed to another centrifuge 125 which separates a solid crystalline product that is used to prepare a concentrated glyphosate salt solution. For this purpose, solids 126 exiting centrifuge 125 are directed to a salt makeup tank 127 where they are neutralized with a base such as potassium hydroxide (KOH) or isopropylamine in an aqueous medium to a typical concentration of from about 400 to about 650 grams per liter, acid equivalent.

Mother liquor 129 from centrifuge 125 contains PMIDA in a proportion sufficient to justify recycle of at least a portion thereof to reactor 101. Mother liquor 131 from centrifuge 121 is divided into a purge fraction 133, which is removed from the process, and a recycle fraction 135, which is returned to evaporative crystallizer 111.

In addition to unreacted PMIDA, the oxidation reaction solution typically contains small proportions of other impurities that are innocuous but generally ineffective as herbicides, and which can compromise the crystallization step and/or reduce productivity. These must ultimately be removed from the process, in part via purge 133 and in part as minor components of glyphosate products. To balance the proportion of impurities purged in fraction 133 with those removed in the aqueous glyphosate salt concentrate product, a mother liquor transfer line 139 is provided for optional transfer of mother liquor from line 135 to neutralization tank 127.

Figure 2:
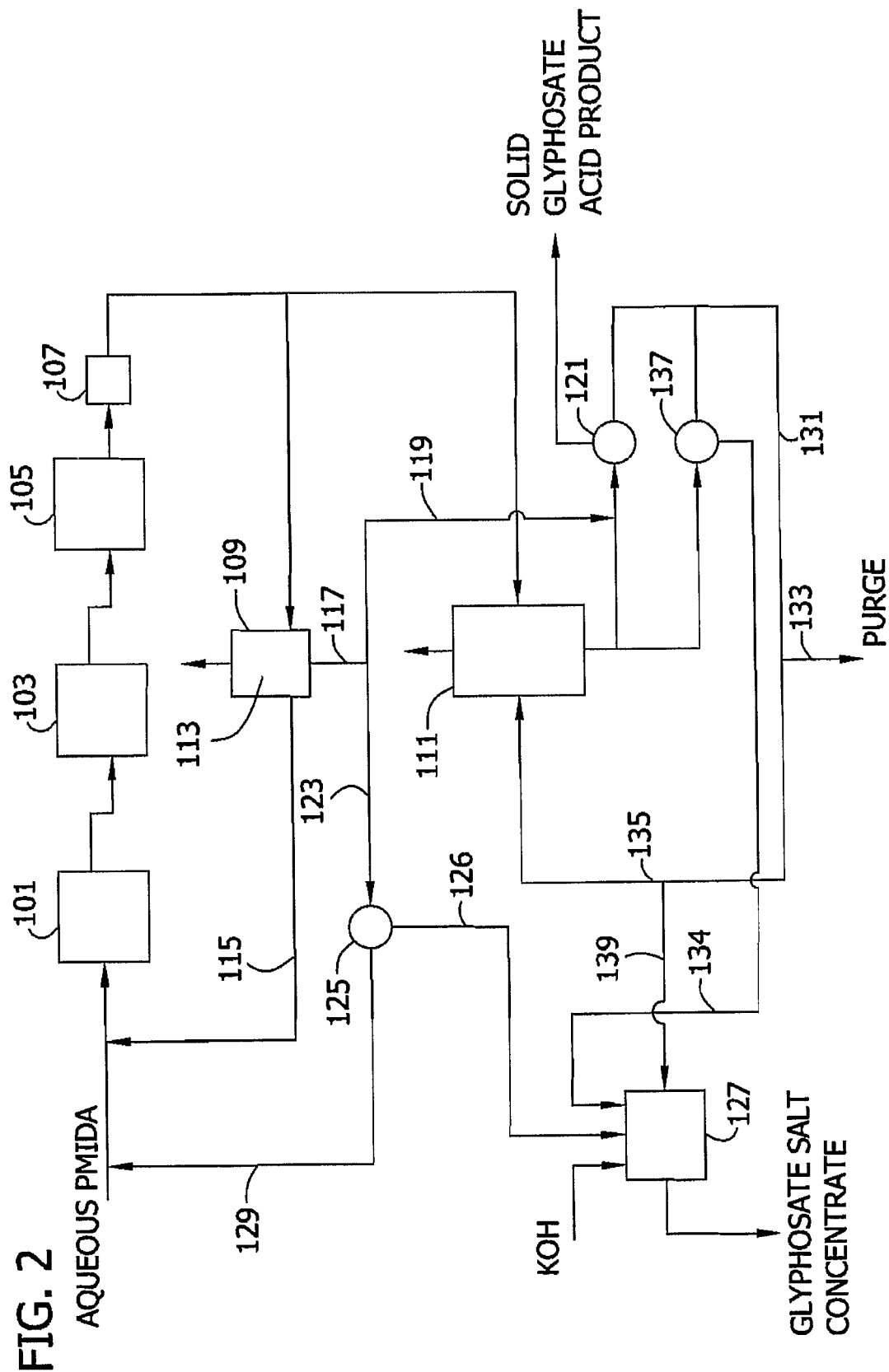
FIG. 2 is a schematic flow sheet illustrating an alternative embodiment of the process of FIG. 1 in which PMIDA that accumulates in the product recovery area can be removed from the process in a controlled manner, more particularly in a manner that allocates PMIDA removal between a solid glyphosate acid product, a concentrated glyphosate salt solution, and a purge stream.

FIG. 2 illustrates a modest refinement of the process of FIG. 1 wherein the crystal slurry exiting evaporative crystallizer 111 is divided between centrifuge 121 and a parallel centrifuge 137. The centrifuge wet-cake from centrifuge 121 is removed from the process and may be utilized or sold as a solid technical grade glyphosate acid product, but the wet-cake 134 from centrifuge 137 is directed to tank 127 for use in preparing a glyphosate salt concentrate. The mother liquor draining from both centrifuges 121 and 137 is combined as stream 131 which is divided between purge stream 133 and stream 135 which is recycled to the evaporative crystallizer.

In operation of the continuous oxidation process depicted in FIGS. 1 and 2, a slurry comprising an aqueous solution comprising from about 6.5% to about 11% by weight PMIDA is introduced continuously into CSTR 101. The aqueous reaction medium formed in CSTR 101 may typically contain from about 0.5% to about 5%, more typically from about 2% to about 5% by weight of a particulate noble metal catalyst suspended therein. For example, the catalyst may comprise a bifunctional noble metal on carbon catalyst as described in U.S. Pat. Nos. 6,417,133, 6,603,039, 6,586,621, 6,963,009, and 6,956,005, U.S. Application Publication No. US 2006/0020143 A1 and International Publication No. WO 2006/031938 A2, which are expressly incorporated herein by reference. A source of oxygen, e.g., air, or preferably oxygen enriched air or substantially pure oxygen, is sparged into the aqueous reaction medium within reactor 101 at pressure in the range from about 105 to about 125 psig and reaction is typically conducted at a temperature in the range from about 90° to about 115° C. Typically, a PMIDA conversion to glyphosate in the range of about 82% to about 85% is realized in reactor 101. Reaction solution containing slurried catalyst exiting CSTR 101 flows to second stage CSTR 103 which is operated under substantially the same temperature conditions as CSTR 101, but with oxygen sparged at an oxygen pressure in the range from about 85 and about 100 psig. PMIDA conversion achieved at the exit of reactor 103 is typically in the range from about 90% to about 97% (i.e., conversion within the second reactor is from about 8% to about 15%, basis, the PMIDA charged to reactor 101).

Reaction solution with slurried catalyst exiting CSTR 103 flows to a third CSTR 105. Oxygen is sparged into reactor 105 at a pressure in the range of from about 60 to about 80 psig. Typically, the temperature of reactor 105 is maintained in substantially the same range as reactors 101 and 103. Conversion in reactor 105 is typically 3% to 5%, basis the PMIDA entering reactor 101, resulting in an overall PMIDA conversion in the continuous reaction system from about 97% to about 99.5%.

Reactors 101 through 105 are vented under feed back pressure control. In a preferred mode of operation, the flow rate of oxygen to each reactor is controlled to establish and maintain a target consumption of the oxygen that is introduced into the reactor in the oxidation of PMIDA and reaction by-products such as formaldehyde and formic acid. The proportionate consumption of oxygen introduced into the reactor is referred to herein as the oxygen utilization. In conventional operation, the pressure is preferably established at a level that provides an oxygen utilization of at least 60%, preferably at least about 80%, more preferably at least about 90%. Consistent with the preferred oxygen utilization, the oxygen feed is divided among a series of CSTRs generally in proportion to the reaction rate prevailing in each of the reactors. Preferably, the reactors are sized to provide a residence time effective to accomplish a substantial fraction of the conversion in the first of a series of, e.g., three CSTRs. For example, 65% to 80% of the oxygen may be fed to the first of three reactors, 20% to 30% to the second, and 1% to 5% to the third. Typically, reaction in all but the last of a series of CSTRs is pseudo zero order in PMIDA. It is believed that this zero order reaction behavior is due to the reaction being mass transfer limited during this portion of the process. Under finishing conditions in the last reactor, the reaction is non-zero order in PMIDA, e.g., approximately first order. As discussed hereinbelow, as the catalyst mass ages, deactivates, conversion may be maintained by increasing the oxygen flow rates, at the same or different allocations of oxygen among reactors (e.g., in the process of FIGS. 1 and 2 by increasing the proportion of oxygen introduced into reactor 101 or 103), to accomplish more of the conversion in the reactors upstream of the last reactor.

Where the oxygen utilization is relatively high, especially where it is greater than 80% or 90%, it has been found that the PMIDA content of the effluent from the final reactor is typically in the range of from about 800 to about 2500 ppm by weight on a solution basis, i.e., from about 8000 to about 25000 ppm by weight on a glyphosate basis. Where glyphosate is recovered by crystallization from the reaction solution in the manner described above, the PMIDA content of the glyphosate product(s) is generally substantially higher than in the product reaction solution exiting reactor 105. Due to recycle of mother liquor containing PMIDA, the aqueous crystallizer feed solutions from which glyphosate is crystallized generally contain PMIDA in a ratio to glyphosate that is at least 25% higher, or in various steady state operations at least 50% higher, than the ratio of PMIDA to glyphosate in the product reaction solution, generally substantially more than 50% higher (in a batch oxidation reaction process the PMIDA concentration in the crystallizer feed solution may be $\geqq 3\times$ the concentration in the oxidation reaction solution, more typically $\geqq 5\times$, even more typically $\geqq 8\times$). The extent of PMIDA buildup is limited by the volume of purge fraction 133. However, when a process of the type illustrated in FIGS. 1 and 2 has reached substantially steady state operation, a PMIDA range of from about 800 to 2500 ppm by weight in the final reaction solution may typically translate into a concentration of 2000 to 6000 ppm by weight on a glyphosate basis in the final glyphosate product, provided that a purge stream is provided in which a reasonable fraction, perhaps up to 10%, of the PMIDA contained in the reaction solution is purged from the process. Where more than one form of product is produced, e.g., where product is provided in both the form of solid technical grade particulate glyphosate acid product and a concentrated solution of a glyphosate salt, the PMIDA content may vary between the plural products, depending in part on the direction and division of various process streams in the product recovery scheme.

It will be understood that a variety of other schemes may be used for the preparation of a glyphosate reaction solution by the catalyzed oxidation of a PMIDA substrate and for the recovery of glyphosate product(s) from a glyphosate reaction solution in the form of a solid technical grade glyphosate product and/or concentrated glyphosate salt solution. For example, the filtered reaction solution may all be directed to an evaporative crystallizer and the product recovered from the crystallizer slurry in a filter or centrifuge for use either as glyphosate acid or in the preparation of a concentrated glyphosate salt solution. In such process, the mother liquor may be divided into a purge fraction and a fraction which is recycled to the evaporative crystallizer. Alternatively, all or a portion of the mother liquor which is not purged may be recycled to the oxidation reaction system. Various oxidation reaction systems for the catalytic oxidation of a PMIDA substrate and alternative process schemes for recovering plural glyphosate products from the oxidation reaction solution, including schemes utilizing substantially adiabatic vacuum crystallization, are known and described, for example, by Haupfear et al. in U.S. Pat. No. 7,015,351 and U.S. Application Publication No. US 2005/0059840 A1, the entire contents of which are expressly incorporated herein by reference.

The process as described above can be routinely operated to generate a product reaction solution exiting the reaction system having a residual PMIDA content of not greater than about 0.25 wt. % (2500 ppm by weight), basis the reaction solution, and that the glyphosate recovered from this solution in accordance with the process as illustrated in FIG. 2 typically has a PMIDA content not greater than about 0.6 wt. % (6000 ppm by weight), glyphosate basis.

It has recently been discovered that, for some applications, it is desirable to produce a glyphosate product having a PMIDA content not greater than about 600 ppm by weight, glyphosate basis. It has further been determined that a concentrated aqueous solution of glyphosate salt and a solid glyphosate acid product, each having a glyphosate basis PMIDA content of <600 ppm by weight, can be consistently produced in accordance with the process of FIGS. 1 and 2, provided that the conversion is sufficient to reduce the PMIDA content of the product reaction solution to about 45 to 60 ppm by weight plus an increment corresponding to whatever fraction of PMIDA may be separated in the product recovery system and returned to the reactor in recycle fractions such as mother liquor streams 115 and 129. For example, to achieve a target concentration of 50 ppm on a glyphosate production rate basis where the PMIDA recycle rate is 200 ppm on the same basis (i.e., the ratio of the rate at which PMIDA enters the oxidation reaction zone(s) in the recycle stream to the rate at which glyphosate flows out in the product reaction solution stream), a residual PMIDA concentration of about 250 ppm can be tolerated in the product reaction solution exiting reactor 105. In the absence of significant PMIDA recycle to the reaction system, as, for example, in a typical batch reaction process, the PMIDA content of the product reaction solution is preferably reduced to the level sought in the PMIDA product. However, higher levels can still be tolerated where the product recovery process includes means for purging a PMIDA-enriched fraction, such as by ion exchange of PMIDA from glyphosate as described hereinbelow.

In the commercial manufacture of glyphosate, low levels of PMIDA in the product reaction solution, effective to yield a glyphosate product having a PMIDA content not greater than about 600 ppm without excessive purge or special separation techniques, have been occasionally and incidentally obtained on a transitory basis under certain non-steady state operating conditions, e.g., during startup of a glyphosate process. However, prior to the present invention, low or otherwise controlled PMIDA content product has not been obtained on a deliberate, consistent or reliable basis. In sustained operation of conventional commercial systems for known commercial applications, generation of such extra low PMIDA content glyphosate would not have been justified, because of the penalties in yield, productivity and/or quality (with respect to by-product impurities such as AMPA and NMG) incurred under the conditions which might have been effective for such sustained operation.

In accordance with the invention, various process stratagems have been discovered for consistently and permanently controlling the PMIDA content of the product reaction solution and particularly at a level below about 60 ppm, or below the sum of about 60 ppm and an increment, if any, corresponding to recycle of unreacted PMIDA from other process operations, for example, in recycle to the oxidation reaction zone from the glyphosate product recovery operation in the continuous process illustrated in FIGS. 1 and 2 or from other further processing steps such as conversion of PMIDA to the N-oxide in accordance with the processes of U.S. Pat. Nos. 5,043,475, 5,077,431 and/or 5,095,140. In addition or in the alternative to such modifications to the reaction system, modifications to the glyphosate recovery process have been devised to recover a low PMIDA content glyphosate product, e.g., <600 ppm, in either one of a plurality of products, or in all the glyphosate products of the process.

Other schemes have been developed for generating a reaction solution having an unreacted PMIDA content <250 ppm on a campaign basis, and/or modifying the glyphosate recovery process on a campaign basis to produce a glyphosate product having a PMIDA content <600 ppm.

Modifications in PMIDA Oxidation Reaction Conditions and Systems

In accordance with the present invention, it has been discovered that oxygen flow to the reactor(s) may be optionally adjusted in a manner that reduces the concentration of PMIDA in the final reaction solution, resulting in a generally proportionate decrease in the PMIDA content of the glyphosate product or products. Generally, it has been found that increasing oxygen flow in one or more of the reactors enhances the conversion of PMIDA to glyphosate. The exact relationship of oxygen flow to PMIDA conversion varies significantly with the other conditions of the process, with the nature of the catalyst, with catalyst age and concentration, with batch vs. continuous operation, with product throughput, and with the peculiarities of the configuration of a specific reactor, its oxygen feed point, agitation system and gas flow patterns. However, those skilled in the art can readily adjust the oxygen flow rate for a specific reactor or series of reactors to obtain a desired response in increased conversion of PMIDA. By way of example, where a continuous reaction system of the type illustrated in FIG. 1 is operating at a residual PMIDA level of 800 to 1500 ppm in the reaction solution exiting CSTR 105, the PMIDA content of the product reaction solution may be reduced to from about 150 to about 250 ppm by a proportionate increase in the sum of the oxygen flow rates to reactors 101 to 105 of roughly from about 0.1 to about 2% relative to the sum of flow rates that yields a PMIDA content of 800 ppm under otherwise identical process conditions, or by adjusting the reaction temperature or the agitation intensity in the reaction zone. Alternatively, such reduction in PMIDA content of the product reaction solution may be achieved by increasing the flow rate of oxygen to the last of the series of reactors, reactor 105, by at least about 5%, typically from about 10% to about 30% relative to the flow rate which yields a PMIDA content of 800 ppm under otherwise identical reaction conditions.

Over an extended period of operations, the catalyst may deactivate to the extent that desired conversion can no longer be achieved by adjustment of oxygen flow to the last of a series of CSTRs. However, up to a limit defined by useful catalyst life (or at augmentation or partial replacement with fresh catalyst), the desired conversion can still be maintained by progressively increasing the oxygen flow to the earlier reactors, e.g., reactors 101 and 103 in FIGS. 1 and 2. Preferably, the oxygen flow rate is increased sufficiently to actually increase the conversion in the reaction solution exiting the penultimate reactor, so that the duty imposed on the last reactor is reduced. Thus, the desired ultimate conversion is obtained even though the productivity of the last reactor per se has declined. Conversion can also be increased by increasing residence time in the reactors. As those skilled in the art will appreciate, an infinite number of combinations of flow rates to the respective reactors may be available to achieve the desired level of PMIDA in the product reaction solution.

In a batch reaction system, the PMIDA content of the reaction solution may optionally be reduced by extending the cycle during which a source of oxygen is sparged into the aqueous reaction medium. For a given operation, a conventional oxygen flow cycle may be identified by any convenient conventional means, as, for example, by periodic analysis of samples from the reactor. Where performance as a function of time is reasonably consistent, timing of the batch may be sufficient and sampling may not be necessary. In any case, it has been discovered that, by extending the oxygen sparging cycle by from about 2 to about 15 minutes, more typically from about 5 to about 10 minutes, PMIDA conversion can be increased to reduce residual PMIDA content from a range from about 275 to about 350 ppm to a range from about 50 to about 100 ppm or even lower.

The achievement of a low PMIDA content in the filtered aqueous reaction product stream by increased oxygen flow or extended batch cycle typically involves a modest penalty in glyphosate yield and an increase in the concentration of certain impurities, prominently aminomethylphosphonic acid ("AMPA"). Where a noble metal on carbon catalyst is used for the reaction, these schemes may also typically result in an increased rate of deactivation of catalyst, resulting in increased catalyst consumption. However, the reduced PMIDA content generally affords a benefit in those applications in which it is desirable to utilize a glyphosate product having a low PMIDA content, such as in the preparation of herbicidal glyphosate compositions for the control of weeds in genetically-modified cotton crops, that outweighs the adverse effects on yield and the minor increase in impurities.

In accordance with the invention, several additional modifications to the reaction system have been identified that can be used in lieu of, or in combination with increased oxygen flow as described above.

Alternatively, or in addition to increasing oxygen flow to the reactor(s), enhanced conversion of PMIDA can be achieved by operation at relatively high reaction temperature within the aforesaid range of from about 70° to 140° C., and/or by modification of the catalyst system.

Conversion of PMIDA is promoted by operation at elevated temperature, e.g., in the range of about 110° C. or above, typically from about 110° to about 125° C. Because higher temperature leads to increased by-product formation, such as by oxidation of glyphosate to AMPA, the temperature is preferably not increased to more than the extent that may be necessary, either alone or in combination with other modifications such as oxygen flow rate, to achieve the target level of PMIDA. A significant effect on conversion can be achieved by operation in the range of from about 115° to about 125° C., or perhaps optimally in the range of from about 118° to about 125° C.

The catalyst system may be modified by an increased charge of noble metal on carbon catalyst, by adding activated carbon to the catalyst system and/or by altering the selection of promoter for the noble metal on carbon catalyst. It has also been found that the catalyst activity may be enhanced by selection of calcination conditions, control of the calcination atmosphere, and other conditions prevailing during the preparation of a noble metal on carbon catalyst, as described, for example, in International Publication No. WO 2006/031938 A2. If a fresh catalyst charge is increased beyond a threshold level, e.g., above a concentration in the range of from about 1.5% to about 2% by weight, the effect may be to increase the oxidation of PMIDA to IDA rather than glyphosate. However, while PMIDA may oxidize to IDA resulting in an overall selectivity loss, the net effect is still to reduce the PMIDA content of the final glyphosate product. Moreover, when a catalyst mass has been used through a substantial number of recycles, activity of the catalyst mass may usefully be increased by purging some fraction of the spent catalyst and adding fresh catalyst in its place. When this method is followed, PMIDA conversion may be significantly enhanced without significant formation of IDA, i.e., selectivity to glyphosate may be substantially preserved.

An activated carbon catalyst such as the catalyst that is described by Chou in U.S. Pat. No. 4,624,937, is highly effective for oxidation of PMIDA to glyphosate, even if not as effective for oxidation of by-product $C_1$ species such as formaldehyde and formic acid. The carbon catalyst is also relatively inexpensive compared to the noble metal on carbon catalyst, though it is typically consumed at a substantially higher rate. Thus, a fairly liberal addition of carbon catalyst to either a batch reactor, or to the last of a series of cascaded CSTRs, (e.g., in a proportion of at least about 1.5% by weight, typically from about 2.5% to about 3.5% by weight, basis, the noble metal on carbon catalyst charge) can materially reduce the residual PMIDA content in the final reaction solution.

Certain transition metals such as Bi and Te are effective as promoters to improve the effectiveness of a noble metal on carbon catalyst for oxidation of by-product $C_1$ species such as formaldehyde and formic acid. However, data indicate that the oxidation of PMIDA may be marginally retarded by such promoters, perhaps by directing oxygen to contact and react with $C_1$ species in preference to PMIDA. When used either alone or in combination with activated carbon for preparation of low PMIDA content glyphosate, a noble metal catalyst can either have no promoter, or have a promoter whose identity and loading is selected to minimize any negative effect on the kinetics of the PMIDA oxidation. In this connection, a particular reactor, such as the final reactor in a series of CSTRs, can be dedicated to substantial extinction of PMIDA, and the use of a catalyst which has no promoter, or in which the promoter is selected to be favorable to PMIDA oxidation, can be limited to the dedicated reactor.

Because further thermal effects are minimal once a relatively high conversion has been achieved, a finishing reactor, such as the final reactor in a series of continuous reactors, can readily be operated as a flow reactor, e.g., with a fixed catalyst bed, rather than a back-mixed reactor, so as to enhance the driving force for extinction of PMIDA. Moreover, such finishing reactor can be added, for example, as reactor n+1 after a series of n CSTRs, for example as the fourth reactor following reactor 105 of FIG. 1. Optionally, the catalyst loaded in such reactor can predominantly or exclusively comprise activated carbon.

In order to minimize residual PMIDA in the product reaction solution exiting the final stage of a cascaded continuous stirred tank reaction system, it is helpful to minimize short circuiting of aqueous medium from the reactor inlet to the reactor exit. Thus, in accordance with principles known to the art, the feed point, exit point, baffle array, agitation pattern and agitation intensity may be selected to minimize the extent of short circuiting. Where a CSTR is provided with an external heat exchanger through which the reaction mixture is circulated for removal of the heat of reaction, the reaction mixture may conveniently be withdrawn from the reactor at a forward flow port in the circulating line. Advantageously, the inlet for reaction medium can be positioned in the same circulating line downstream of the exit port by a distance sufficient to avoid any short circuiting due to axial backmixing. For example, the exit port can be placed in the circulating line upstream of the heat exchanger and the inlet port can be located immediately downstream of the heat exchanger.

In accordance with the invention, further process modifications outside the principal PMIDA oxidation system, may be used to reduce the PMIDA content of the finished glyphosate product(s). Such additional modifications, as described hereinbelow, may be used together with or in lieu of any combination of the modifications to the reaction system that are described above.

PMIDA Purge

For example, in the process of FIG. 1, the volume of purge stream fraction 133 can be increased relative to evaporative crystallizer mother liquor recycle fraction 135, thus reducing the steady state inventory of PMIDA in the glyphosate product recovery area of the process. The extent of purge required to obtain a given specification for a given form of glyphosate product varies depending on the PMIDA content of the filtered reaction product stream and the exact material balance of the overall process, and especially the material balance of the glyphosate recovery area. The effect of increased purge may be augmented by a more extended wash of the separated glyphosate solids that are obtained as a centrifuge cake in centrifuges 121 and 125, or in filters or centrifuges that may be used in alternative schemes for product recovery. Increased wash volume is ordinarily integrated with the purging scheme because either the wash liquor itself must be purged; or, if the wash liquor is combined with one or more of the recycle mother liquor streams, it marginally increases the amount of PMIDA which must be purged from the process. In either case, the net purge volume is generally increased by an increment corresponding to the volume of the wash liquor. An increase of wash volume might be achieved independently of the purge fraction where the quality of the wash solution permits its use in preparing the aqueous solution of PMIDA which is introduced into the reaction system.

Ion Exchange

In a further alternative embodiment of the invention, PMIDA may be removed from one or more process streams by ion exchange. A variety of options may be followed in providing for removal of PMIDA by ion exchange. For example, an ion exchange column could be used to remove PMIDA from mother liquor as it is recycled from the evaporative crystallizer centrifuge 121 (and/or 137) before separation of purge fraction 133, or in recycle mother liquor fraction 135 after separation of the purge fraction, or in stream 129 from centrifuge 125. Alternatively, or additionally, an ion exchanger could be positioned in the filtered reaction solution stream ahead of the point where it is divided between the vacuum crystallizer 109 and the evaporative crystallizer 111 in FIG. 1.

In an ion exchange system, the PMIDA-bearing stream is contacted with an anion exchange resin, preferably an anion exchange resin which has a greater affinity for the more strongly acidic PMIDA anion than for the relatively more weakly acidic glyphosate anion and for many of the other compounds in this stream. Because the process stream from which PMIDA is to be removed typically has a high ratio of glyphosate to PMIDA, the resin's affinity for PMIDA should be significantly greater than its affinity for glyphosate. Efficient separation of PMIDA is enhanced where the affinity of the resin for PMIDA is at least two times, three times, four times, five times, 10 times, 20 times or as much as 100 times its affinity for glyphosate. Weakly basic exchange resins are preferred. Functional sites of conventional weak base anion exchange resins typically comprise secondary amine or tertiary amines. Available anion exchange resins typically comprise, e.g., a styrene butadiene polymer having a secondary or tertiary amine site which may be protonated in acidic solution to function as an anion exchanger. Suitable commercially available resins include, for example: AMBERLYST A21, AMBERLITE IRA-35, AMBERLITE IRA-67, AMBERLITE IRA-94 (all from Rohm & Haas, Philadelphia, Pa.), DOWEX 50×8-400 (Dow Chemical Company, Midland, Mich.), LEWATIT MP-62, IONAC™ 305, IONAC™ 365 and IONAC™ 380 (Sybron Chemicals, Birmingham, N.J.), and DUOLITE™ a-392 (Diamond Shamrock Corp., Dallas, Tex.).

A complication in removal of PMIDA by ion exchange can arise from the presence of a substantial fraction of chlorides in the filtered reaction solution, which tend to be concentrated somewhat in the solution ultimately subjected to ion exchange such as evaporative crystallizer mother liquor 131. When an acidic solution such as mother liquor recycle solution 131 is passed over an anion exchange resin, chloride ions are retained at the protonated amine sites preferentially to PMIDA. Where this is the case, two columns may typically be provided in series, with the first column dedicated to removal of chloride ions, with either a strong or weak base anion exchange resin, and the effluent from the first column passed through a second column comprising a weak base exchange resin wherein PMIDA anions are removed. Each column may be eluted and the anion exchange resin regenerated by passage of a caustic solution, typically sodium hydroxide (NaOH), through the column.

The solution from which PMIDA and/or chlorides are to be removed is passed through the column in which the desired exchange occurs until breakthrough of the ion to be removed is observed in the effluent from the column. Breakthrough may occur when the entire column has reached an equilibrium level of chloride ion or PMIDA as the case may be. As saturation is approached, the capacity of the column for the target anion may be reduced to some extent by the presence of the anions of components that are of comparable acidity as the target anion, e.g., phosphate and N-formylglyphosate ("NFG"). Breakthrough may be determined by any conventional means of detection, including, for example, conductivity, absorbance of light (254 nm), pH and the like. In a preferred method, PMIDA breakthrough is detected by monitoring conductivity of the column eluate. For example, as described in greater detail below, a potential may be applied between a working electrode and another electrode immersed in the column eluate or a sample thereof, and measurement made of a function of the power consumed in maintaining a select current density, or a select potential difference between the electrodes. Alternatively, the end point of an ion exchange cycle can be practiced by volumetric control of the quantity of aqueous solution passed through the column (i.e., the cumulative quantity of mother liquor or other PMIDA-containing stream passed through the anion exchange bed relative to the volume of the bed, typically expressed in "bed volumes.").

After an ion exchange cycle is complete, the column can be eluted to remove the anion that has been collected therein.

A column in which chlorides have been collected may be eluted with a caustic solution, e.g., NaOH, to regenerate free amine sites and produce an eluate salt solution that may typically be discarded. Interstitial caustic is removed by washing the column with water. Unless interstitial caustic is removed, it is recycled to the crystallizer with adverse impact on the crystallization.

A column in which PMIDA has been collected may first be washed with water to displace process liquid from the column. Thereafter the column may be eluted with a strong acid such as HCl to remove PMDIA for recovery; and then regenerated, typically with a caustic solution such as NaOH, and then washed with water to remove interstitial caustic. Eluate comprising PMIDA can be recycled to the reaction system for further conversion of the PMIDA to glyphosate. Illustrative examples of acids which can be used for elution of PMIDA from an ion exchange column include strong mineral acids such as hydrochloric acid or sulfuric acid. In various embodiments, the ion exchange resin may be contacted with a wash solution, or multiple wash solutions during a series of wash steps subsequent to elution. Suitable wash solutions include, for example, water, a buffer solution, a strong base such as KOH, NaOH, or $NH_4OH$ or a weaker base such as $Na_2CO_3$.

During elution of a column loaded with PMIDA, the column effluent is monitored for the conjugate base of the strong acid, e.g., chloride ion when $Cl^-$ is detected in the effluent. Upon appearance of chlorides, recycle of eluate to the PMIDA oxidation step is terminated, and the column is washed with water, then caustic and then again water to return it to the free amine state. If desired, buffers and/or solvents may be used in washing of the column after elution, but this is not ordinarily necessary or useful.

Ion exchange can be conducted at ambient or elevated temperature. More particularly, the mother liquor from the evaporative crystallizer centrifuge 121 (and/or 137) may be treated by ion exchange resin without heating or cooling prior to introduction into the ion exchange column. Typically, this stream has a temperature in the range of from about 45° to about 85° C., more typically from about 55° to about 75° C. Column dimensions and flow rates through the column are governed by standard column design principles and can be readily determined by one skilled in the art.

If desired, a third column can be provided downstream of the PMIDA column for recovery of glyphosate by ion exchange. See, for example, the process as described in U.S. Pat. No. 5,087,740, which is expressly incorporated by reference herein.

In various embodiments, a still further ion exchange column may be provided for recovery of platinum or other noble metal that may have been leached from the catalyst used in the oxidation of PMIDA. A process for recovery of such noble metal by ion exchange is described in copending and co-assigned U.S. application Ser. No. 11/273,410, filed Nov. 14, 2005, entitled RECOVERY OF NOBLE METALS FROM AQUEOUS PROCESS STREAMS, which is also expressly incorporated herein by reference. Preferably, ion exchange for recovery of noble metal is conducted upstream of the ion exchanger used for separation of PMIDA or removal of chlorides.

In a continuous process such as that illustrated in FIG. 1, a pair of ion exchange columns can be provided in parallel for each ion exchange operation that is conducted as part of the process. In this manner, one column can be used for removal of target anion while the other is being eluted and regenerated.

Although ion exchange has been described above with reference to ion exchange columns, the resin may alternatively be added directly with agitation as a solid phase reagent to the stream from which the PMIDA (or other target anion) is to be removed. Ion exchange operations have been described above with reference to the continuous processes depicted in FIGS. 1 and 2. Removal of excess PMIDA by ion exchange is also useful in a simplified glyphosate product recovery scheme in which all product reaction solution is directed to a single glyphosate recovery stage such as a single evaporative crystallizer. A single crystallizer typically may be used where the oxidation reaction is conducted in a batch mode. In such a process, glyphosate crystals are separated from the crystallization slurry by filtration or centrifugation, and the mother liquor typically recycled to the crystallizer. In extended operations, a fraction of mother liquor is purged to remove impurities. Ion exchange for removal of PMIDA from the mother liquor allows reduction of the purge fraction necessary to provide a given PMIDA specification in the glyphosate product. Also, the PMIDA which removed can be recovered by elution as described above and recycled to the oxidation reactor.

Figure 3:
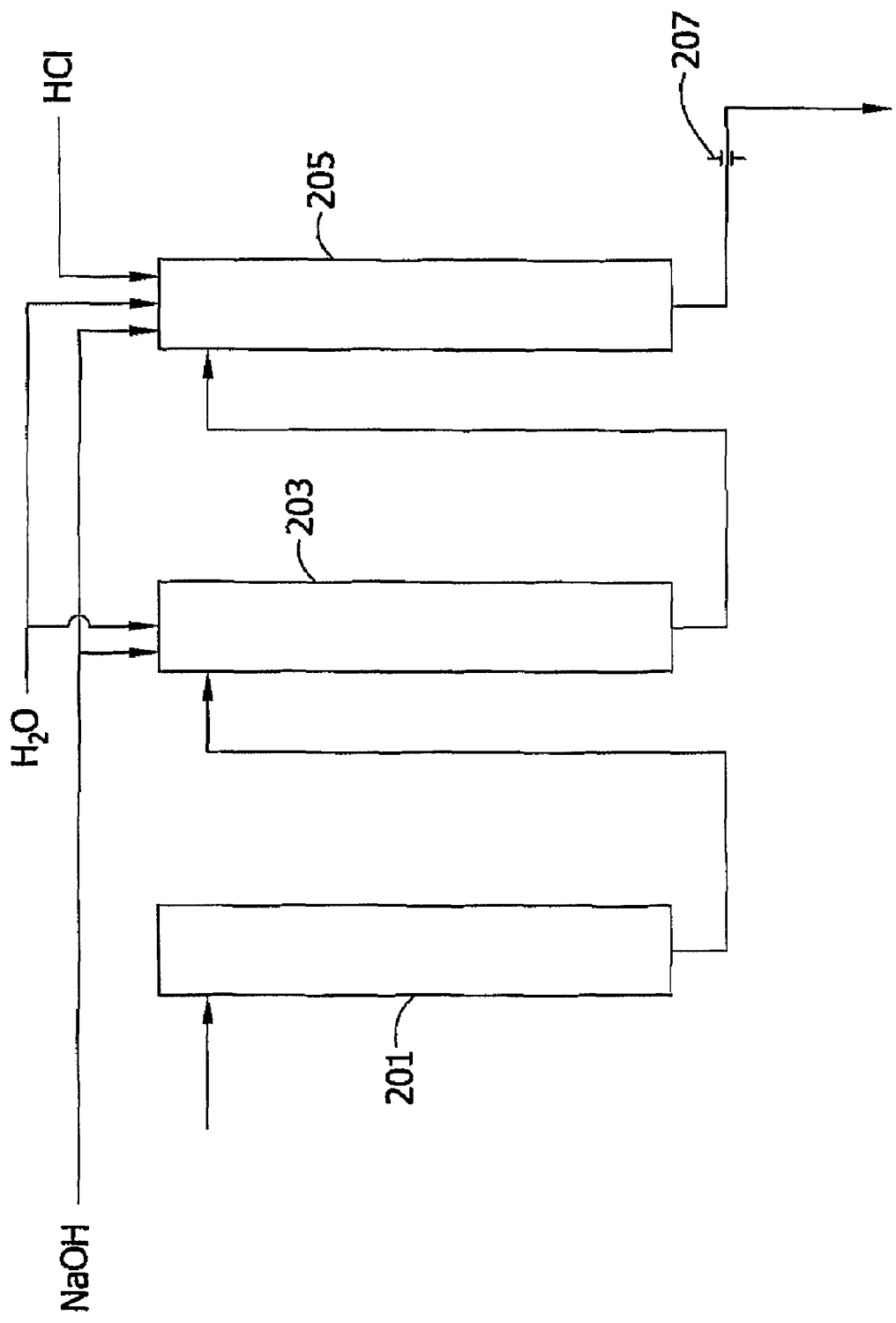
FIG. 3 is a schematic flow sheet illustrating an exemplary ion exchange system that may be used in conjunction with the process for the manufacture of glyphosate illustrated in FIG. 1 or 2.

FIG. 3 illustrates an exemplary ion exchange system, located, for example, in stream 131 of FIG. 1 or 2, upstream of the purge 133. As illustrated, the system comprises three columns in series, a platinum (or other noble metal) recovery column 201, a chloride removal column 203 and a PMIDA removal column 205. Column 201 comprises an adsorption zone which may comprise activated carbon, or more typically a weak base anion exchange resin, strong base anion exchange resin, strong acid cation exchange resin weak acid cation exchange resin, chelating resin, or in some instances, mixtures thereof. Specific resins useful in the recovery of solubilized platinum are described in U.S. Ser. No. 11/273, 410, expressly incorporated herein by reference. Preferably, a chelating resin is used. Column 203 comprises an anion exchange zone containing a resin of the type described hereinabove for removal of chlorides, and column 205 comprises an anion exchange zone containing a resin of the type described for the removal of PMIDA.

Although only a single column is depicted for each recovery or removal operation in FIG. 3, typically at least a pair of columns is provided in parallel at each stage to allow one column to be eluted, regenerated, and washed while the other is in operation for removal of Pt, $Cl^-$ or PMIDA, respectively. Operating conditions for column 201 are described in U.S. Ser. No. 11/273,410. As further described in the above-mentioned application, breakthrough of noble metal from column 201 may be detected by ICP-MS, ICP-OES, or AA. A simple conductivity device is effective for determining breakthrough of chlorides from column 203 or 205.

While FIG. 3 depicts separate columns (or column pairs) in series for chloride removal and PMIDA removal, respectively, the two columns function as a single adsorption system so far as adsorption phenomena are concerned, at least in the case where the ion exchange properties of the resins used in columns 203 and 205 are substantially the same. In any case, all adsorbable components of the solution are initially adsorbed on column 203 but PMIDA is progressively displaced by Cl– as the column becomes loaded. PMIDA desorbed from or passing through column 203 is adsorbed on the anion exchange resin in column 205. When column 203 (or a corresponding adsorption zone within a single column) becomes loaded with chloride, the latter ions eventually break through in the effluent from column 203 (or corresponding zone) and begin displacing the PMIDA from column 205 (or a corresponding downstream adsorption zone of a single column). Separating the adsorption bed into two columns facilitates monitoring the chloride wave and scheduling regeneration of anion exchange resin for sustained operations. Breakthrough from column 205 may result from either saturation of the resin therein with PMIDA or displacement of PMIDA by chloride. In either case, breakthrough may occur before maximum PMIDA loading is realized, with the PMIDA content of the effluent progressively increasing as column saturation is approached, rising to the level in the inlet mother liquor stream when saturation is reached. Where chloride displaces PMIDA, the PMIDA loading reaches a maximum and then begins to decline as it is displaced by chloride. In the system depicted in FIG. 3, this condition can be avoided if column 203 is regenerated as soon as chloride breakthrough is observed. In either case, process operators can identify an optimum balance between PMIDA removal efficiency and column loading.

Regardless of whether the chloride and PMIDA ions are removed in physically separate adsorption beds in series or in a single adsorption bed, the adsorption system may be considered to comprise two distinct adsorption zones, one in which chlorides are being adsorbed and another in which PMIDA is being adsorbed. However, the size and location of these adsorption zones are not static. The boundary between the zones moves as the chloride wave advances in displacing PMIDA from the resin.

Shown at 207 is a device effective to sense breakthrough of PMIDA from column 205. The device comprises a pair of electrodes immersed in the stream exiting the column or a sample thereof, and is controlled to maintain a select current density or impose a select voltage or schedule of voltages between the electrodes. Where the device is controlled to maintain a select current density, breakthrough of PMIDA is reflected in a drop, typically a relatively sharp drop in the voltage required to maintain the select current density. Where a select voltage, or programmed series of voltages is imposed, breakthrough of PMIDA is indicated by a significant increase in current at a voltage that is sufficient for electrolytic oxidation of $C_1$s and PMIDA but not residual glyphosate. Detailed descriptions of devices which function on these bases are set forth in greater detail below.

Whenever any of columns 201, 203 or 205 reaches a breakthrough condition, introduction of mother liquor is terminated and the adsorbed component recovered. In the case of column 205, PMIDA may be eluted with a strong acid such as HCl. Both columns 203 and 205 may be regenerated using a caustic eluant, followed by a water wash, as described above. The aqueous NaCl eluate may be discarded. In the case of column 201, the noble metal component may optionally be eluted with an eluant, e.g., an acidic eluant where the noble metal species is present in the form of cation, or a caustic eluant where the noble metal is present in an anion. However, in the case of column 201, more quantitative recovery can generally be achieved by removing the loaded resin from the column, incinerating the resin, and recovering noble metal from the ash.

Recovery of noble metal in column 201 is typically in the range between about 60% and about 85%, or even higher. Thus, in monitoring operation of this column "breakthrough" is a relative term, and the breakthrough detection device is calibrated to detect an increase in signal above a steady state level. In any event, a portion of the noble metal is typically lost in purge stream 133 or in the product glyphosate salt concentrate. Where PMIDA is removed by ion exchange via column 205, it has been found that a portion of the noble metal passing through columns 201 and 203 is adsorbed on the resin contained in column 205. If this column is regenerated or washed with aqueous ammonia, the platinum is desorbed, and ultimately lost either in the purge stream or by incorporation into the aqueous glyphosate salt product. However, it has been discovered that if the column is regenerated with a strong base such as an alkali metal hydroxide, e.g., NaOH or KOH, and washed with strong base or water, platinum species are typically not desorbed, but remain on the column, thus allowing ultimate recovery of this fraction of the platinum by removal and incineration of the resin.

Disposition of the eluates from columns 203 and 205, respectively, is as described above. The acidic eluate comprising PMIDA is typically recycled to the reaction system. As regeneration proceeds, the chloride content typically declines in the caustic regeneration solution exiting the column. Advantageously, a portion of the caustic regeneration solution, particularly that exiting the column toward the end of the regeneration cycle, may be preserved and used in a subsequent regeneration cycle in the same or a parallel PMIDA removal column.

Although an anion exchange resin which has a substantially higher affinity for PMIDA than for glyphosate is preferably selected for column 205, some glyphosate is typically removed along with PMIDA from the mother liquor or other solution that is processed in the column. The incidence of glyphosate removal may be relatively significant when the column contains fresh or freshly regenerated resin. As PMIDA accumulates in the column, the glyphosate fraction moves down (or in any event toward the column exit) in a manner similar to the operation of a chromatographic column. In an alternative embodiment of the process, the effluent from column 205 may be monitored not only for PMIDA but also for glyphosate. As the column becomes loaded with PMIDA, glyphosate breaks through first. When the column is eluted, a glyphosate fraction comes off first and may be segregated for recycle, e.g., to the evaporative crystallizer. Prior to elution, the column is washed for removal of residual glyphosate caught in the interstitial spaces between the resin beads. The glyphosate content of the wash solution may also be sufficient to justify recycle to the evaporative crystallizer.

Where the operation of column 205 is monitored by use of device 207, the threshold voltage at which a significant current density is realized may first be observed to decline to a value reflective of the oxidation of glyphosate. Such threshold voltage substantially prevails until PMIDA breakthrough approaches. During elution, a similar voltage response or requirement should be observed during elution of the glyphosate fraction which may be directed, e.g., to a feed tank for the evaporative crystallizer. When the voltage required to sustain a target current density declines to a value reflective of the oxidation of PMIDA, the eluate may be redirected for recycle to the reactor, or alternatively to the purge.

According to a further alternative for recovery of glyphosate, a column loaded with both glyphosate and PMIDA may be initially eluted with a relatively weak base such as isopropylamine ("IPA") to remove the relatively weakly sorbed glyphosate in the form of the salt. Optionally and preferably, neat liquid IPA can be used for the elution, which produces an eluate consisting of a relatively concentrated solution of the IPA salt of glyphosate. This eluate may be directed to neutralization and mixing tank 127 and used directly in producing aqueous IPA glyphosate concentrates.

In accordance with a further process alternative, as mentioned above, another column comprising an ion exchange zone comprising a resin effective for sorption of glyphosate, typically a further ion exchange column, can be provided downstream of column 205. This column is not shown in FIG. 3 but may be positioned to receive the process stream that has been passed in series through columns 203 and 205, or in series through columns 201, 203 and 205.

Polishing Reactor in Product Recovery Process

According to a further alternative, PMIDA can be removed from product recovery process streams by catalytic oxidation to glyphosate. In addition to or in lieu of a finishing reactor as described above in the principal reaction train, polishing reactor(s) can be positioned in one or more process streams within a product recovery system of the type illustrated in FIG. 1. For example such a reactor could be positioned in the feed stream to evaporative crystallizer 111 (as a pre-recovery polishing reactor), in mother liquor stream 131 exiting evaporative crystallizer centrifuge 113, or elsewhere in the process.

Such a further finishing or polishing reactor can optionally be operated with a carbon only catalyst. Moreover, since only marginal oxidation is involved, thermal effects are minimal, making it at least potentially advantageous to operate the reactor as a flow reactor with a fixed bed of catalyst, thus enhancing the driving force for substantial extinction of PMIDA. Where the reactor is placed in stream 131, ahead of the purge stream, the effect on overall yield of the marginal oxidation of glyphosate to AMPA is minimal. Oxidation reaction systems for preparation of glyphosate reaction solutions by catalytic oxidation of a PMIDA substrate including finishing or pre-recovery polishing reactors are described by Haupfear et al. in U.S. Pat. No. 7,015,351, the entire contents of which is incorporated herein by reference.

According to a still further alternative, the process may typically include a feed tank for the catalyst filter 107, and a further marginal reduction in the residual PMIDA content may be realized by sparging an oxygen-containing gas, e.g., substantially 100% $O_2$ into the contents of the filter feed tank, or into the slurry of catalyst in product reaction solution in a line entering the feed tank. In order to prevent settling of catalyst in the filter feed tank, its contents are typically agitated, which may aid in oxygen distribution, mass transfer and consequent oxidation of residual PMIDA. Oxygen sparging may contribute to agitation.

Crystallizer Operations

Process options effective to produce a product of relatively low PMIDA content have implications for the operation of evaporative crystallizer 111. PMIDA has been found to function as a solubilizer for glyphosate. Thus, where the reaction system is operated under such conditions as to yield a filtered product reaction solution of relatively low PMIDA content, and/or where the filtered reaction solution is passed through a finishing reactor for further conversion of PMIDA to glyphosate, and/or where PMIDA is removed from recycle mother liquor by ion exchange, solubility of glyphosate in the recycle mother liquor can be lowered. At a given system pressure, a lower PMIDA/glyphosate ratio causes crystallization to commence at relatively lower temperature, which can result in fouling of process side heat exchanger surfaces in or associated with the evaporative crystallizer.

Figure 4:
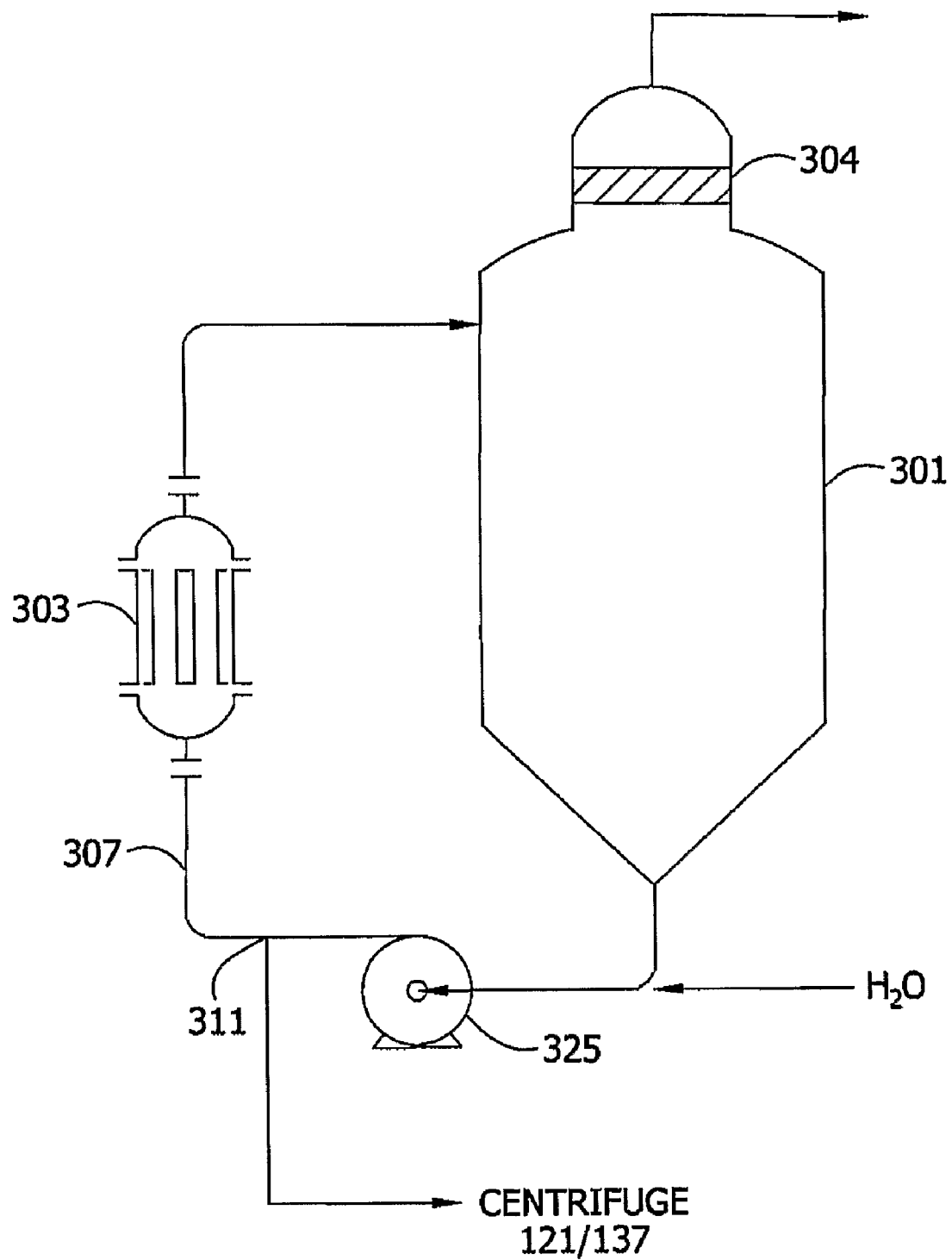
FIG. 4 is a schematic flow sheet illustrating an evaporative crystallization system modified to accommodate low PMIDA content in the feed solution without excessive fouling of the heat exchange surfaces and which may be used in conjunction with the process for the manufacture of glyphosate illustrated in FIG. 1 or 2.

FIG. 4 illustrates an evaporative crystallization system modified to accommodate low PMIDA content in the feed solution without excessive fouling of the heat exchange surfaces. In the system of FIG. 4, crystallizer 109 comprises a vapor liquid separator 301, an external heat exchanger 303, and an axial or centrifugal circulation pump 305 and line 307 for circulation of the crystallization slurry between the vapor liquid separator through the heat exchanger. A mist eliminator 309 in the upper portion of the vapor liquid separator helps to collect entrained liquid and return it to the liquid phase within the separator body. Crystallization slurry is drawn off through port 311 in the circulation line for delivery to centrifuge 121 and optionally centrifuge 137. Fouling of heat exchanger 303 is potentially attributable to accumulation of glyphosate on the process side tube surfaces, but may also be attributable to plugging of the heat exchanger tubes with large chunks of crystalline material which may calve off the walls of separator 301.

It may further be noted that the commencement of crystallization at lower temperature results in an enhanced crystallization yield. While this effect may be advantageous from the standpoint of initial crystallizer productivity, and marginally beneficial with regard to yield on raw materials, the higher solids content of the circulating slurry is believed to have an adverse effect on heat transfer. Increased solids content increases the effective viscosity of the circulating slurry, thereby increasing pressure drop through the heat exchanger. At a given limiting pump head, this results in a decreased flow rate, decreased velocity along the process side of the tube wall, and consequently decreased heat transfer coefficients. Thus, even without any fouling or plugging of tubes, heat transfer rates and productivity can be compromised by the higher solids content obtained as the crystallization temperature drops with PMIDA content.

In any event, injection of water into the circulating pump suction imposes a sensible heat load that tends to reduce the rate of precipitation in the tubes. Although water injection does not reduce the steady state composition of the liquid phase in the vapor/liquid separator, it marginally reduces the degree of supersaturation in the liquid phase entering the heat exchanger, and may thus marginally reduce the tendency of the tubes to foul by further encrustation with glyphosate. Perhaps more significantly, it reduces the solids content of the slurry passing through the heat exchanger, thus reducing the viscosity, and contributing to increased process side velocity and heat transfer coefficients.

Injection of water above the mist eliminator is useful in minimizing pressure drop through the mist eliminator and controlling the extent of crystallization on the walls of the separator. Increasing the slurry circulation rate via pump 303 serves to reduce the temperature rise in the heat exchanger and enhance the scouring action of the circulating slurry, further contributing to control of fouling.

Aside from the complications which it can create in the operation of the evaporative crystallizer, ion exchange also functions to reduce the chloride and phosphate content of the mother liquor circulating in the evaporative crystallization system. Whether as a result of lower chloride and phosphate content or otherwise, it has been found that enhanced crystal growth is achieved in the evaporative crystallizer in operations wherein PMIDA, and necessarily also chloride and phosphate, is removed by ion exchange. The larger crystals thus produced have superior dewatering properties as compared to the crystals obtained in an evaporative crystallization system wherein a mother liquor of relatively high PMIDA, Cl–, and/or phosphate concentration circulates between the evaporative crystallizer and centrifuge 121 or 121 and 137. Production of relatively larger crystals is advantageous in removal of residual impurities, including PMIDA, by separation of solids from mother liquor in the centrifuge(s) and washing of the centrifuge cake. It has further been observed that, where the crystallizer is operated to consistently generate relatively large glyphosate particles, the fouling effect of reduced PMIDA content is at least partially offset. Heat exchange surfaces are generally less prone to fouling in an operation wherein heat is transferred to a slurry comprising relatively large particles than in an operation where relatively fine crystals are produced.

Designated Operations for Low PMIDA Glyphosate

Certain of the process modifications as described above are effective for producing low PMIDA content glyphosate, but involve risks with regard to yield, productivity, product quality and catalyst deactivation as affected by the presence of by-product impurities such as AMPA, NMG, etc. Thus, for example, while modifications comprising increased oxygen flow or extended batch cycles or higher temperatures are effective for lowering the PMIDA content, they involve risk of overreaction, resulting in the oxidation of glyphosate to AMPA, or the formation of by-products such as NMG. Modifications to the material balance of the glyphosate recovery system, such as those discussed above in connection with FIG. 2, can result in yield losses due to increased purge of unreacted PMIDA from the process, and the direct loss of glyphosate yield that is associated with the glyphosate content of the purge stream.

Further in accordance with the invention, operation of the process can optionally be managed to consistently and reliably meet demand for low PMIDA glyphosate product, while minimizing the net impact on yield and productivity, and enabling the manufacture of product which does not require an exceptionally low PMIDA content to be conducted under conditions which afford optimal yield, productivity and AMPA/NMG content without constraints that can otherwise be imposed by operation under conditions which generate the exceptionally low PMIDA product.

In accordance with such embodiments of the invention, glyphosate is produced in an industrial manufacturing facility which comprises a reaction system for the catalytic oxidation of PMIDA in an aqueous medium. During designated operations within such facility, the process is conducted under conditions effective to consistently produce a glyphosate product having a PMIDA content less than about 0.06 wt. %, basis glyphosate. The glyphosate product as produced under such conditions is segregated from other glyphosate product that is produced under other conditions wherein the PMIDA content is greater than 0.06 wt. %, typically greater than 0.10 wt. %, more typically greater than 0.15 wt. % on a glyphosate basis.

In the practice of such embodiments of the invention, the catalytic reaction system may optionally be operated in accordance with any of the various alternatives described above for providing a product reaction solution containing PMIDA in a proportion less than about 60 ppm by weight, basis glyphosate plus an increment, if any, resulting from PMIDA that is recycled to the reaction zone. Additionally, or alternatively, the product recovery operation may be operated under added or modified purge conditions to yield one or more glyphosate products containing less than about 0.06 wt. % PMIDA, or ion exchange may be used to remove PMIDA from a stream from which glyphosate is crystallized or otherwise recovered. The designated operations may, for example, comprise a campaign during which all or part of the glyphosate produced in the facility is generated under conditions effective to provide a low PMIDA content. Such a campaign can be of any desired duration, e.g., a week, two weeks, a month or several months, sufficient, e.g., to produce at least 1500 metric tons, more typically at least about 7500 metric tons of the low PMIDA product. As part of the method for producing low PMIDA glyphosate on a campaign basis, a manufacturing forecast is preferably prepared based on projected sales data, and the periods during which all or part of the operations of the industrial facility are dedicated to production of low PMIDA glyphosate may be designated on an organized basis in view of such forecasts. In the practice of these embodiments of the invention, it may be advantageous, for example, to schedule the production of low PMIDA glyphosate during startup after a maintenance turnaround of the reaction system, product recovery system or both; or after introduction of a fresh catalyst charge. Where there is any predictable volatility to raw material prices, scheduling can further be determined on the basis of such prices.

Where the facility comprises a plurality of batch oxidation reactors for the conversion of PMIDA to glyphosate, one or more of the plurality of reactors may be dedicated for a select period of time to operation under conditions effective to produce a product reaction solution containing less than about 250 ppm PMIDA, glyphosate basis.

Where the facility comprises a continuous reaction system for the conversion of PMIDA to glyphosate, the system may typically comprise a plurality of continuous stirred tank reactors ("CSTRs") in series. In such a series of, e.g., two or three CSTRs, the last of the reactors may function as a finishing reactor which operates under terminal conditions, typically at >300 ppm PMIDA, more typically in the range of 500 ppm PMIDA, glyphosate basis. In designated operations, the conditions in the final reactor may be modified by increased oxygen flow, higher temperature, etc., to yield a product reaction solution containing <250 ppm PMIDA. Over a campaign necessary to produce some minimum quantity of glyphosate, e.g., at least about 1500 metric tons, preferably at least about 3000 metric tons, more preferably at least about 7500 metric tons, the finishing reactor may be dedicated to operation under such conditions.

To maintain productivity, it may be preferable to achieve the desired PMIDA content in the product reaction solution by altering conditions in the entire series of reactors, as by increasing the oxygen flows thereto. Where the manufacturing facility comprises a plurality of continuous reaction trains, one or more of these may be dedicated to the production of low PMIDA glyphosate, either permanently or during a low PMIDA product campaign, while the remaining reaction trains may be operated under conditions optimal for producing glyphosate of a higher acceptable PMIDA content.

Allocation of PMIDA Among Plural Grades of Glyphosate

On either a permanent or campaign basis, the processes as illustrated in FIGS. 1 and 2 may also be adapted to produce different grades of glyphosate product, e.g., one grade that has a PMIDA content less than 600 ppm for use in those applications in which it is desirable to utilize a glyphosate product having a low PMIDA content, such as in the preparation of herbicidal glyphosate compositions for the control of weeds in genetically-modified cotton crops, and another grade of higher PMIDA content which is quite satisfactory for multiple other applications. Generally, the centrifuge wet-cake produced in centrifuge 125 has a lower PMIDA content than the wet-cake produced in centrifuge 121 (or 137) because the mother liquor from the vacuum crystallizer is less concentrated than the mother liquor from the evaporative crystallizer, and because no recycle mother liquor stream is introduced into vacuum crystallizer 109. The PMIDA content of the solid glyphosate acid product removed from the process by centrifuge 121 can be balanced with the PMIDA content of the salt concentrate exiting the process from neutralization tank 127 by increasing the fraction of vacuum crystallizer slurry underflow 117 from the decantation step that is directed to evaporative crystallizer centrifuges 121 relative to that which is directed to centrifuge 125 and/or by increasing the fraction of evaporative crystallizer slurry that is directed to centrifuge 137 for production of evaporative crystallizer centrifuge wet-cake to be incorporated into the concentrated glyphosate salt solution in salt makeup tank 127. If desired, the PMIDA content can be unbalanced, and a disproportionately low GI content salt concentrate prepared by minimizing the fraction of vacuum crystallizer slurry 117 directed to centrifuge 121, and transferring mother liquor from the evaporative crystallizer circuit to the neutralization tank via mother liquor transfer line 139 and/or by eliminating the fraction of evaporative crystallizer slurry which is directed to centrifuge 137.

Alternatively, a low PMIDA content solid glyphosate acid product can be prepared by diverting PMIDA to the salt makeup tank 127. In this case, a relatively high fraction of the vacuum crystallizer slurry underflowing the decantation step is directed to centrifuge 121, and a high fraction of the evaporative crystallizer slurry is sent to centrifuge 137. According to these various process schemes, the process material balance can be managed to contemporaneously, or indeed simultaneously, to produce two separate glyphosate products of distinctly different glyphosate basis PMIDA content.

As a further alternative to the preparation of low PMIDA content glyphosate product, the product obtained during process startup can be segregated and dedicated for use in glyphosate composition for application to and weed control in genetically-modified cotton crops. By starting up with water in the evaporators, neutralization tank and process storage vessels (not shown), the impact of PMIDA in recycle mother liquor can be avoided immediately after startup, and kept to a modest level during the early portion of the transient period in which the product recovery area gravitates to steady state operation.

Further alternative process schemes for allocating residual PMIDA among two or more glyphosate products are described by Haupfear et al. in U.S. Application Publication No. US 2005/0059840 A1, the entire text of which is expressly incorporated herein by reference.

Whether by sequential operation, segregated operations, or control of process material balance to simultaneously yield different grade products, the processes of the invention can be implemented to yield a plurality of differing grade products, including a low PMIDA product having a glyphosate basis PMIDA content typically less than about 1000 ppm, preferably less than about 600 ppm, and at least 25% lower than at least one other, or preferably any other, of such plurality. Moreover, using any one or more of the various process stratagems described above (or below), a low PMIDA product may be produced having a glyphosate basis PMIDA content that is less than about 1000 ppm, or less than about 600 ppm, and at least about 50% lower, or even at least about 75% lower, than the PMIDA content of another of the plurality of products, or preferably any such plurality.

Conversion and End Point Determination

As noted above, modifications to the oxidation process conditions to achieve an exceptionally low PMIDA content may inevitably involve some penalty in yield, productivity, catalyst deactivation, cost and/or AMPA/NMG content of the glyphosate product. These penalties can be largely avoided by the alternative of operating the reaction system under conditions optimal for the generation of a product reaction solution having a PMIDA content in the range of from about 300 to about 800 ppm, and removing PMIDA by ion exchange in the course of glyphosate product recovery. However, the ion exchange process involves its own capital, operating and maintenance costs. Accordingly, a further incremental advantage can be achieved by controlling the operation of the oxidation reaction system to generate a product reaction solution that meets a desired PMIDA content sufficient to yield an ultimate product of the preferred specification, e.g., <600 ppm PMIDA, while avoiding overreaction that consumes glyphosate and unnecessarily increases the AMPA or NMG content of the reaction solution.

Further in accordance with the invention, various methods and systems have been devised to monitor the conversion of PMIDA and/or the composition of the product reaction solution and to identify an end point or residence time at which the reaction can be terminated and/or the product reaction solution withdrawn from the reactor. These include: (i) in-line chromatography; (ii) Fourier transform infra red analysis; (iii) determination of cumulative oxygen consumption and/or time differential oxygen consumption; (iv) monitoring oxidation/reduction potential; (v) monitoring dissolved oxygen concentration in the aqueous liquid reaction medium; (vi) monitoring the oxygen concentration in reactor vent gas; (vii) monitoring the $CO_2$ concentration in the reactor vent gas; (viii) determining cumulative $CO_2$ generation and/or analysis of the $CO_2$ generation profile; (ix) monitoring instantaneous $O_2$ consumption; (x) monitoring instantaneous $CO_2$ generation; (xi) electrochemical indication of residual PMIDA; (xii) cumulative heat balance on the reaction system; (xiii) time differential heat generation in the reaction system; and combinations of these techniques.

According to the first of these alternatives, the reaction solution can be periodically sampled and the sample passed through a chromatographic column, preferably a liquid chromatography column such as a high performance liquid chromatography (also known as a high pressure liquid chromatography or "HPLC") column, that is positioned in proximity to the reactor in which the conversion is concluded, i.e., either in a batch reactor, at the exit of a continuous plug flow reactor such as a reactor comprising a fixed catalyst bed, or in the final of a series of CSTRs. Although the internal pressure of the reactor is sufficient for withdrawal of a sample by operation of a sampling valve, in some instances it may be desired to use a metering pump to provide a specimen of defined volume for the HPLC. A filter is provided upstream of the HPLC (or metering pump) for removal of catalyst and any other solids. The sample may optionally be passed through a heat exchanger to cool it to a controlled temperature for passage through the chromatographic column and/or may be diluted to avoid crystallization in the sample or if called for in the chromatography protocol. Conventional detection means well known to the art may be used to determine the PMIDA content of the sample.

Figure 22:
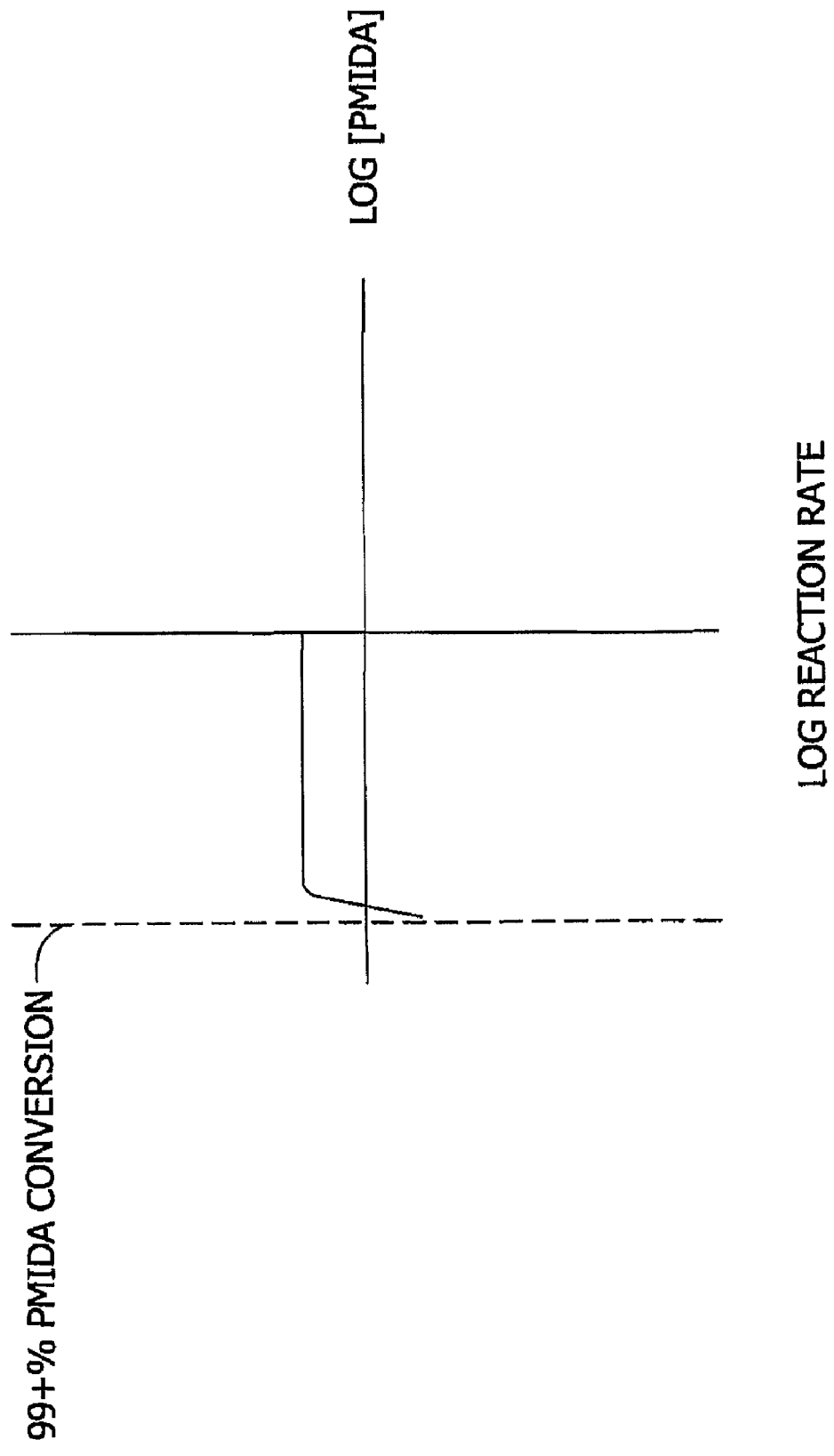
FIG. 22 is a typical plot of log (reaction rate) vs. log (residual PMIDA concentration) in the batch oxidation of PMIDA to glyphosate, showing that the reaction is pseudo zero order until high conversion has been achieved, thereafter substantially first order.

In a batch process, the reaction may be terminated as the desired PMIDA content is reached. In a continuous process, the residence time, oxygen flow rate and/or reaction temperature may be adjusted to achieve the desired conversion. In a continuous reaction system, the reaction rate is believed to be typically limited by gas/liquid mass transfer until a relatively high conversion has been attained, but after that becomes kinetics limited. Since reaction as such is non-zero order in PMIDA, the reaction progressively slows proportionately to residual PMIDA content as quantitative conversion is approached, irrespective of how much oxygen is supplied. Thus, the typical behavior of the reaction is exemplified in FIG. 22 which plots the log of the reaction rate vs. the log of the residual PMIDA concentration. Until high conversion is reached, the consumption of PMIDA is pseudo zero order. When a high concentration, e.g., in the 95-98% range is reached, the consumption of PMIDA becomes limited by the reaction kinetics, which are typically approximately first order with respect to PMIDA. Continuous reaction can be conducted, e.g., in a series of CSTRs as described above, or in a plug flow reactor such as a tubular reactor comprising a fixed or fluidized catalyst bed. In such systems, conversion rates may be most effectively increased by increasing oxygen supply along the flow path of the reaction medium in the oxidation reaction zone(s) prior to transition to non-zero order conditions. This increases the mass transfer rates and, thus, the reaction rate in the upstream space where mass transfer controls, and leaves additional reactor space and residence time for conversion under non-zero order kinetics-limiting conditions to a desired conversion and/or residual PMIDA content. Although FIG. 22 shows the PMIDA consumption rate as substantially constant until it becomes kinetics limiting, it will be understood that oxygen flow may be reduced toward the end of a batch reaction, or in the penultimate reactor of a series of CSTRs, which may potentially impact mass transfer coefficients and consequent PMIDA consumption rates, depending on the nature and intensity of mechanical agitation. Oxygen flow rate and temperature may also be adjusted in a batch process as desired to obtain the target PMIDA content in a prescribed batch reaction cycle.

Although even in-line HPLC involves some lag between sampling and analytical results, such lag may not significantly compromise control of the reaction end point, especially in a continuous process, or in a batch process operated using a noble metal on carbon catalyst. It has been observed that glyphosate is not as susceptible to being over-oxidized to AMPA where a noble metal on carbon rather than an activated carbon catalyst is used. It has further been observed that extended exposure to oxidation reaction conditions does not tend to generate as much NMG in the presence of a noble metal on carbon catalyst as it typically does in the presence of an activated carbon catalyst.

In fact, based on a progression of HPLC data on recently preceding batches, or taken during recently preceding continuous operations, it has been observed that the reaction end point, or the appropriate reactor residence time, can be controlled with reasonable accuracy based on either time alone, or time differential from the point at which the PMIDA conversion is determined by HPLC to have reached a certain level, e.g., 95% or 98%. Moreover, a desired conversion or reaction end point can be projected from a series of chromatographic analyses in the manner described below with respect to the use of FTIR for making such projection.

The use of in-line Fourier transform infra red ("FTIR") analysis for monitoring PMIDA conversion is described fully in U.S. Pat. No. 6,818,450 which is expressly incorporated herein by reference. As described therein, in-line FTIR spectroscopy may be used to quantitatively measure one or more of PMIDA, glyphosate, formaldehyde, formic acid, N-methyl-N-(phosphonomethyl)glycine ("NMG"), N-methylaminomethylphosphonic acid ("MAMPA") or aminomethylphosphonic acid ("AMPA") in aqueous mixtures thereof. More preferably, an internal reflectance FTIR method is used for "in-situ" measurement of the infrared spectrum absorbed by the aqueous reaction solution in or exiting one or more of the oxidation reaction zones or reactors. The internal reflectance FTIR method allows for the infrared spectrum absorbed by the reaction solution to be measured in place by locating a sensor probe in, on or in proximity to a process line or reaction vessel so that it is immersed in the reaction solution or positioned on a direct or reflected line of sight to the reaction solution thus allowing the reaction solution to be directly scanned in substantially real time without removing a sample of the solution from the vessel or process line in which it is contained. Advantageously in-situ measurements provide real time or substantially real time measurements of the reaction solution.

In general, internal reflectance relates to a process wherein an infrared light beam is modulated using an interferometer, and the modulated beam is reflected off a sample and returned to a detector wherein the spectral regions absorbed as well as the intensity of the absorbance within those regions is determined. One technique for practicing the internal reflectance method is attenuated total reflectance (ATR) spectrometry which measures the absorbance in a thin layer of the sample in contact with the sampling surface of a sensor device. That is, a sensor probe is placed in direct contact with the sample. A modulated infrared beam is transmitted from the FTIR spectrometer to the sensor probe wherein the beam is transmitted through a sampling surface on the probe such that the beam penetrates into a thin layer of the sample in contact with the sampling surface of the probe and is reflected back into the sensor probe. Significantly, the beam is modified by the sample due to the absorbance characteristics of the sample. The modified beam is then optically transmitted to the FTIR spectrometer's detector. Depending on the ATR probe selected (i.e., the optical characteristics and geometry of the sampling surface) the modulated infrared beam may reflect off of both the sample layer and the sampling surface a number of times before finally returning back into the sensor probe, providing additional data to the detector. Thus, ATR probes are typically described by the number of reflections that occur through the sample layer. Preferably, the ATR probe utilizes at least about 3, more preferably at least about 6 and still more preferably at least about 9 reflections or greater.

Preferably, the sampling surface of the ATR probe is comprised of diamond. ATR probes comprising a diamond sampling surface may further comprise an additional optical element which acts both as a support for the diamond, and for transmitting and focusing the modulated infrared beam to and from the diamond sampling surface. Since the second optical element is not in contact with the reaction solution, it is less important that the second optical element have the corrosion and abrasion resistance as the sampling surface. Zinc selenide crystals have similar optical qualities as diamond at a substantially reduced cost. Accordingly, zinc selenide may be used as an additional optical element.

The sampling surface of the ATR probes may be concave, convex or have a relatively flat surface curvature. Preferably, the sampling surface of the ATR probe is relatively flat. Without being held to a particular theory, it is believed that sampling surfaces having a significant degree of curvature tend to promote the adherence of particulates such as catalyst or undissolved product to the sampling surface thereby interfering with the sensor.

ATR probes having the characteristics described above, i.e., a relatively flat diamond sampling surface are commercially available, for example, from Axiom Analytical, Inc. (Irvine, Calif.). In a preferred embodiment, a 9 reflection, diamond-composite sensor probe having a relatively flat diamond sampling surface, such as a DICOMP™ SENTINAL™ ATR diamond-composite sensor probe which is commercially available from ASI Applied Systems (Annapolis, Md.), is used.

The FTIR spectrometer detects the intensity or amplitude of the modified beam across the infrared region and transforms the data into an absorbance spectrum, i.e., absorbance vs. wavenumber. FTIR spectrometers typically use two types of detectors, a mercury cadmium telluride (MCT) detector or a deuterated triglycine sulfate (DTGS) detector. Although MCT detectors tend to be faster than DTGS detectors and have a high sensitivity, MCT detectors typically require liquid nitrogen cooling. Therefore, it may be preferred to use a DTGS detector which does not require liquid nitrogen cooling. Either type of detector may be used.

The reaction solution is typically sampled over a spectral range of wavelengths from about 2 to about 50 microns, i.e., wavenumbers ranging from about 200 to about 5000 cm$^{-1}$, more preferably from about 650 to about 4000 cm$^{-1}$, with wavenumber being the reciprocal of wavelength and proportional to frequency. The infrared spectrum is a continuous spectrum, however for analytical reasons, discrete wavenumbers or groups of wavenumbers are typically measured. The wavenumber resolution, i.e., the range of wavenumbers that are grouped together for each discrete measurement may be increased or decreased to affect the signal to noise ratio of the FTIR spectrometer. That is, as the numerical value of the wavenumber resolution is decreased, more measurements are taken across the spectrum and the resolution of the spectrum increases. However, increases in the wavenumber resolution also typically results in a corresponding increase in the level of "noise". Generally, FTIR spectroscopy methods use wavenumber resolutions having a numerical value of 2, 4, 8 or 16, i.e., sample data are collected over discrete ranges of 2, 4, 8 or 16 wavenumbers with the resolution being inversely proportional to the numerical value of the wavenumber resolution. Typically, a wavenumber resolution of 8 appears to provide a spectrum with a fairly good resolution while minimizing the amount of "noise." Changes in the wavenumber resolution may be made, however, without departing from the scope of the present invention.

Additionally, FTIR spectroscopy generally utilizes a number of scans providing additional interferometric data, i.e., intensity vs. wavenumber data used in the Fourier transform to produce the spectral data, i.e., absorbance vs. wavenumber. If the number of scans is set at 180, for example, the spectrometer will scan the entire wavelength range specified 180 times and produce 180 interferograms, or 180 intensity measurements per wavenumber, or more precisely, per wavenumber grouping as determined by the wavenumber resolution. Fourier transforms then combine the intensity data and convert the 180 interferograms into a single absorbance spectrum. The number of spectra, i.e., scans can also affect the signal to noise ratio. Generally about 180 scans may be sampled with a new spectrum measurement being generated about every 145 seconds. More preferably, the number of scans is at least about 360, producing a new measurement every 5 minutes or greater in an effort to improve the signal to noise ratio.

Preferably, the number of scans performed is such that the frequency in which new spectrum measurements are taken is less than about the residence time of the oxidation reaction zone affecting the concentration being measured. That is, as described above, the oxidation process may utilize one, two or more reaction zones or reactors for converting PMIDA to a glyphosate product. Each reaction zone has a corresponding residence time in which the reaction takes place. In addition, if these reaction zones are placed in series, there will additionally be an overall residence time for the reaction system comprising the summation of the residence times for each reaction zone. The residence time considered for determining the sample frequency depends on whether PMIDA or other analyte is being measured to monitor the progress of the oxidation reaction in a particular reaction zone, or the progress of the overall reaction system.

Preferably at least one, more preferably at least two, and still more preferably at least three measurements are taken within a time period of no greater than the residence time for the oxidation reaction zone being monitored. Typically, the residence time for a particular reaction zone may vary from about 3 to about 120 minutes, more preferably from about 5 to about 90 minutes, still more preferably from about 5 to about 60 minutes, and still even more preferably from about 15 to about 60 minutes. The residence time for a particular reaction system may vary depending on the total throughput and the quantity of the reaction mixture in the reactor without departing from the scope of the present invention.

A single analyte will produce a spectrum having an absorbance profile characteristic of that analyte. That is, the spectrum contains absorbance features that may be associated with the analyte. Accordingly, the concentration of the analyte may be determined using a mathematical model representing the relationship between the concentration of the analyte and the absorbance profile. The mathematical model may be developed by measuring the spectrum for a number of standard samples having known concentrations and mathematically correlating the concentration as a function of the absorbance profile using a number of correlation methods. Unfortunately, the characteristic spectrum for a mixture of analytes such as the reaction solution resulting from oxidation of PMIDA is more complex in that the characteristic absorbance spectrum for the various analytes are broad and overlap significantly. This overlap precludes the use of simple univariate correlation methods for quantitation of the analytes in a reaction mixture. This problem may be overcome by applying more powerful multivariate mathematical correlation techniques to the analysis of the spectral data. These multivariate mathematical techniques when applied to process chemical analysis are collectively referred to as chemometrics. This technique uses complex mathematics such as matrix vector algebra and statistics to extract quantitative information (e.g., concentrations) from highly convoluted or statistically confounded data such as the spectrum obtained from a mixture of analytes to develop a mathematical model, also called a chemometric model representing the quantitative information as a function of the spectrum. A number of multivariate mathematical techniques have been developed such as; K-Nearest Neighbors analysis (KNN), Heirarchical Cluster Analysis (HCA), Principal Component Analysis (PCA), Partial Least Squares (PLS) analysis, and Principal Component Regression (PCR) analysis. Commercially available software packages are capable of performing many of the multivariate mathematical correlation techniques listed above. In fact, at least one commercially available software package called PIROUETTE (which can be obtained from Infometrics, Inc., P.O. Box 1528 Woodinville, Wash. 98072) is capable of performing all of the correlation techniques listed above.

Commercially available FTIR spectrometers often include chemometric analysis software. In particular, PLS and PCR are typically used for determining a chemometric model, and applying it to a FTIR spectral measurement to calculate a property of the sample measured. Of these two, PLS is most commonly applied to FTIR spectral data because it generally provides the most accurate chemometric models. PLS allows each analyte to be modeled separately, and only requires knowledge of the particular analyte being modeled. That is, it does not require that the concentration of each absorbing analyte be known as long as each absorbing analyte is represented in the standards used for developing the chemometric model. Advantageously, the standards can be taken directly from the process and need not be separately prepared, thus allowing consideration of the impurity profile of the reaction mixture when determining the chemometric model for each analyte to be measured. However, it should be noted that the absorbance of the spectral regions is generally nonlinear with respect to concentrations. Thus, the chemometric models correlating the concentration and the absorbance spectrum should be developed over particular ranges of concentration for the individual analytes of the reaction solution. That is, the standards used in the chemometric analysis should be representative of the matrix of concentrations for each analyte in the reaction solution.

In general, therefore, a number of standards are analyzed using the FTIR Spectrometer to measure the spectrum for each standard. The concentration of a particular analyte can then be mathematically modeled as a function of the spectra obtained i.e., an algorithm is developed that correlates the concentration and the spectrum. Although any of the multivariate mathematical calibration techniques may be used, a preferred embodiment uses the PLS method to model the spectra as a function of concentration. The number of standards used is preferably at least about 10 and more preferably at least about 20. In general, the accuracy of the model increases with increases in the number of standards used to generate the model. Therefore, the number of standards used to generate the model may be as high as 50 or greater. Such standards may be prepared mixtures, or alternatively, may be samples of the particular process mixture to be analyzed. However, as stated earlier, it is preferred that the process mixture is used such that the impurity profile is considered in the PLS analysis when generating the chemometric model. The concentration of the analyte being modeled in each standard may be measured off-line using standard analytical techniques such as high pressure liquid chromatography (HPLC). Accordingly, chemometric models may be generated using a partial least squares regression analysis for spectra obtained from reaction mixtures from either a batch or a continuous oxidation process based on-line spectral measurements and off-line HPLC concentration measurements.

As stated earlier, the FTIR scans the reaction solution over a spectral range of wavelengths corresponding to wavenumbers of from about 200 to 5000 $cm^{-1}$ and more preferably from about 650 to about 4000 $cm^{-1}$. Although the entire spectral region scanned may be used in the PLS analysis, generally, the spectral region considered in the PLS analysis is preferably from about 800 to about 1800 $cm^{-1}$ when modeling the PMIDA substrate, glyphosate product, formaldehyde or formic acid analytes. More preferably, however one or more spectral regions selected from the total spectrum are considered in the PLS analysis, with the regions being selected based on the analyte to be measured. For example, spectral regions to be considered in the PLS analysis may be selected by identifying spectral regions of characteristic peaks for each analyte in a solute such as water. Preferably however, the spectral region used in the PLS analysis to develop a chemometric model for PMIDA is from about 800 to about 1450 $cm^{-1}$, and more preferably from about 1065 to about 1400 $cm^{-1}$. The spectral region or regions used in the PLS analysis to develop a chemometric model for glyphosate in the reaction solution are preferably from about 800 to about 1450 $cm^{-1}$, and more preferably both the region from about 865 to about 945 $cm^{-1}$ and the region from about 1280 to about 1460 $cm^{-1}$. The spectral region used in the PLS analysis to develop a chemometric model for formaldehyde is preferably from about 800 to about 1450 $cm^{-1}$, more preferably from about 945 to about 1150 $cm^{-1}$, still more preferably from about 945 to about 1115 $cm^{-1}$, and still more preferably from about 1000 to about 1075 $cm^{-1}$. Finally, spectral region or regions used in the PLS analysis to develop a chemometric model for formic acid is preferably from about 800 to about 1450 $cm^{-1}$, more preferably the region(s) from about 1150 to about 1300 $cm^{-1}$ and/or from about 1650 to about 1800 $cm^{-1}$. While the preferred spectral regions for formic acid provide reasonable accuracy at higher concentrations of formic acid, i.e., around from about 2,000 to about 5,000 ppm formic acid, the accuracy of the model decreased significantly at lower concentrations, i.e., less than about 1,000 ppm or even less than about 600 ppm. Significantly, a strong absorption band exists within the formic acid spectral region at around 1721 $cm^{-1}$. This band is close to the 1600 $cm^{-1}$ water region which, for aqueous mixtures, is subtracted out as a background and thus can be inconsistent and difficult to quantify. Thus, to minimize the effects of the water subtraction, the preferred spectral region used in the PLS analysis to develop a chemometric model for low concentrations of formic acid is preferably from about 1710 to about 1790 $cm^{-1}$. Surprisingly, by avoiding the spectral region which overlaps the water region, the present invention provides quantitative measurement of formic acid at concentrations less than about 1,000 ppm, less that about 600 ppm and even less than about 300 ppm.

Using the PLS analysis techniques therefore, chemometric models used to determine the concentration of PMIDA, glyphosate, formaldehyde, and/or formic acid analytes as a function of the absorption spectrum may be developed and used in combination with the FTIR spectrometer to provide real-time concentration data for process mixtures from either a batch or a continuous process thus allowing for improved studies of the reaction kinetics, improved reaction control, and in the case of the batch processes, a more accurate and timely reaction end point determination to be made.

For example, using the techniques described above, chemometric models have been developed using an FTIR spectrometer and a diamond-composite ATR probe such that the concentration of PMIDA in a reaction solution may be measured over a range of concentrations of from about the detection limit, currently about 50 ppm, to about 4% with a PLS mean error of less than about 0.2% for a batch oxidation process and may be measured over a range of concentrations of from about 200 ppm to about 4,500 ppm with a mean error of about 200 ppm for a continuous oxidation process. The concentration of glyphosate product in a reaction solution may be measured over a range of concentrations of from about 5% to about 10% with a mean error of less than about 0.2% for batch oxidation processes and may be measured over a range of concentrations of from about 4% to about 8% with a mean error of about less than about 0.2%, more preferably less than about 0.07% for continuous processes. The concentration of formaldehyde in a reaction solution may be measured over a range of concentrations of from about 130 ppm to about 6,000 ppm with a mean error of less than about 150 ppm for batch processes and may be measured over a range of concentrations of from about 250 ppm to about 4,500 ppm with a mean error of about less than about 55 ppm and even over a range of concentrations of from about 100 ppm to about 400 ppm with a mean error of less than about 50 ppm and preferably less than about 30 ppm for continuous processes. Finally, the concentration of formic acid may be measured over a range of concentrations of from about 0.3% to about 1.3% with a mean error of less than about 0.03%, preferably less than about 0.02% for batch processes and may be measured over a range of from about 0.1% to about 0.4% with a mean error of about less than about 0.02%, more preferably less than about 0.01% for continuous processes.

As described in U.S. Pat. No. 6,818,450, in response to the measurements made by in-line FTIR analysis, various adjustments may be made to either a batch or continuous oxidation reaction system as are discussed above with respect to in-line HPLC. More particularly, the FTIR analytical methods described above may be used to measure the progress or condition of the reaction solution resulting from the oxidation of a PMIDA substrate to form a glyphosate product by providing substantially real time concentration analysis for PMIDA or one or more other analytes. In response to the substantially real time measurement, one or more process effects may be controlled by adjusting or maintaining the value of one or more independent process variables affecting the rate of oxidation of the PMIDA substrate, the rate of oxidation of formaldehyde, the rate of oxidation of formic acid, the rate of oxidation of glyphosate product to aminomethylphosphonic acid or salt or ester thereof. Independent process variables affecting the rate of oxidation of the PMIDA substrate, the rate of oxidation of formaldehyde, the rate of oxidation of formic acid, the rate of oxidation of glyphosate product to aminomethylphosphonic acid (or salt or ester thereof) include but are not necessarily limited to: the rate of introduction of molecular oxygen into the continuous reaction zone, the rate of withdrawal of gas from the reaction zone, the oxygen partial pressure at a select location within the reaction zone or in contact with the liquid reaction medium, the temperature of the reaction mixture, the rate of introduction of the aqueous feed mixture to the reaction zone, the rate of withdrawal of the reaction solution from the reaction zone, the amount of catalyst added to the reaction zone, the amount of catalyst removed from the reaction zone, the amount of a supplemental catalyst promoter added to the reaction zone and the intensity of agitation of the reaction mixture.

For example, the oxidation reaction may be carried out in a batch process. An internal reflectance sensor, preferably an ATR probe is inserted directly into the reactor, or alternatively is placed in-line with a recycle loop to enable in-situ real time or substantially real time measurements of the concentration of at least one of the analytes in the reaction mixture. The progress of the reaction can be determined by monitoring the decrease in the concentration of the PMIDA substrate, for example, or alternatively by monitoring the increase in the concentration of the glyphosate product, thus enabling real time or substantially real time determinations of the reaction endpoint. In addition, the data from the FTIR may be electronically communicated to a conventional process control apparatus. Preferably, the process controller is configured such that in response to the data showing the end point of the reaction had been reached, the process controller instructs a control device such as a control valve to terminate the introduction of the oxygen-containing gas into the reaction zone(s) such that the oxidation reaction is terminated. It should be noted that the above example is for illustrative purposes only and in no way is intended to limit the manner in which the progress of the batch oxidation process or the condition of the reaction mixture therein is controlled in response to the analyte concentration measurement provided by the FTIR analytical method.

In another embodiment, FTIR analysis is used to monitor a PMIDA oxidation process conducted in a continuous fashion in two or more CSTRs in series as described above and, for example, in U.S. Pat. No. 7,015,351, the entire contents of which are incorporated herein by reference. For example, the concentration of unreacted PMIDA, glyphosate product and/or oxidation by-products in the reaction mixture effluent are measured using the analytical method described above. In a particularly preferred embodiment of the present invention, the concentration of unreacted PMIDA, glyphosate product and/or oxidation by-products in the intermediate aqueous reaction mixture withdrawn from the first stirred tank reactor and/or in the final reaction mixture effluent withdrawn from the second or subsequent stirred tank reactor may be measured using the analytical method described above. Based on these and other process measurements, control adjustments can be made, thus the conversion of the PMIDA substrate and condition of the reaction mixture may be controlled by controlling the total oxygen feed to the continuous oxidation reactor system, i.e., each of the stirred tank reactors and/or the apportionment of the total oxygen feed between the two or more CSTRs and may be adjusted to beneficially affect the yield and quality of the glyphosate product. Alternatively, other variables may be controlled such as the partial pressure of oxygen at a select location within one or more of the reaction zones or in contact with the liquid reaction medium of each reaction zone, the rate of withdrawal of gas from one or more of the reaction zones, the temperature of the liquid reaction medium within one or more of the reaction zones or exiting one or more of the reaction zones, the rate of withdrawal of reaction product solution from one or more of the reaction zones, the liquid level of reaction mixture in one or more of the reaction zones, the weight of reaction medium in one or more of the reaction zones, addition or removal of catalyst to the oxidation reaction system via one or more of the reaction zones, shifting the relative proportions of the total catalyst mass in one or more of the reaction zones as well as a catalyst holding tank, the addition of a supplemental catalyst promoter to one or more of the reaction zones and the intensity of mixing in one or more of the reaction zones.

Moreover, in making adjustments of control variables in response to FTIR analysis, other process effects may be taken into account, e.g., the oxygen content of the gas withdrawn from the reaction zone(s), dissolved oxygen in the liquid medium in the reaction zone(s), the response of an oxygen electrode or voltage of an oxidation/reduction potential electrode, and the noble metal content of the liquid phase of the reaction mixture withdrawn from the reaction zone. By considering these together with current values for control variables and real time FTIR analysis of the concentrations of one or more analytes in the reaction mixture(s), one or more control variables may be adjusted to conform the process to established process constraints and/or to optimize economically significant outputs such as yield, conversion, selectivity, by-product content and process emissions. With the benefit of substantially real time analysis of reaction mixture composition, optimization can be determined either ad hoc based on known process performance relationships, or in accordance with protocols that have been established based on such relationships. As appropriate, material balance, energy balance, kinetic, mass transfer, heat transfer, thermal stability, catalyst deactivation profiles, and other conventional considerations can form the basis for establishing protocols. As may be convenient, such protocols may optionally be reduced to algorithms which can be programmed onto a processor. Assimilating additional information, including both control variables and performance measurements such as those described above, the processor may then determine optimum settings for one or more of the aforesaid independent variables in accordance with the protocol for obtaining a desired or optimal value for the concentration of one or more of the analytes with respect to an economic or process criterion selected from the group consisting of conversion of substrate, yield of said product on said substrate, selectivity of the oxidation reaction for the glyphosate product, quality of product recoverable from the reaction mixture, productivity, emissions in process effluents, stability of catalyst activity, and manufacturing cost.

To improve determination of residual PMIDA at the conclusion of a batch cycle, or under terminal conditions in a continuous back mixed reaction system, the chemometric models for refining the FTIR analysis of the various components of the reaction solution may be integrated with material balance computations, energy balance computations and other measured process data to further enhance the precision and accuracy of PMIDA determination.

In a particularly advantageous application of FTIR, the instantaneous rate of depletion of PMIDA during non-zero order reaction conditions may be used to aid in determining the instantaneous PMIDA concentration. As discussed in more detail below in connection with methods based on oxygen consumption, carbon dioxide generation and heat generation, the order of the PMIDA oxidation reaction, the order of reactions by which formaldehyde is oxidized to formic acid and formic acid is oxidized to $CO_2$ and water, and the kinetic rate constants for the depletion of PMIDA and oxidation of by-products such as formaldehyde and formic acid, may be estimated from historical analytical data, or historical operational data as obtained from laboratory and/or industrial oxidation reactions. As further explained below, the estimate of the kinetic rate constants may also be refined by reference to current operational data, including the observed rate of decline in the rate of reaction. Whereas the measure of reaction rate and decline thereof is indirect in the case of oxygen consumption, carbon dioxide generation or heat generation, FTIR provides a direct measurement of residual PMIDA, formaldehyde and formic acid concentrations. Thus, a chemometric model based on FTIR allows reaction material balance, energy balance and kinetic reaction rate computations to be integrated with direct quantitative measurement of residual PMIDA in projecting an end point of the reaction. During non-zero order reaction when the rate of reaction is declining, a sequence of two or more FTIR measurements may provide a reliable basis for projecting the time at which an end point corresponding to a desired degree of PMIDA conversion (and residual PMIDA concentration) may be achieved. In a batch reaction, the separate analyses of the series are taken at different times during the course of the reaction, with preferably at least two of these being taken during the non-zero order reaction period approaching the end of the batch. In a continuous reaction system, the samples may be taken at differing residence times, again preferably in a non-zero order regime. In these circumstances, the rate of the reaction declines from analysis to analysis as a function of residual PMIDA content which is defined by the order of the reaction, affording a basis for projecting the time by which a desired end point concentration of PMIDA will be attained. To the extent that the reaction approximates first order in PMIDA, the projection may be made by straight line extrapolation on a plot of the logarithm of concentration vs. time.

Figure 5:
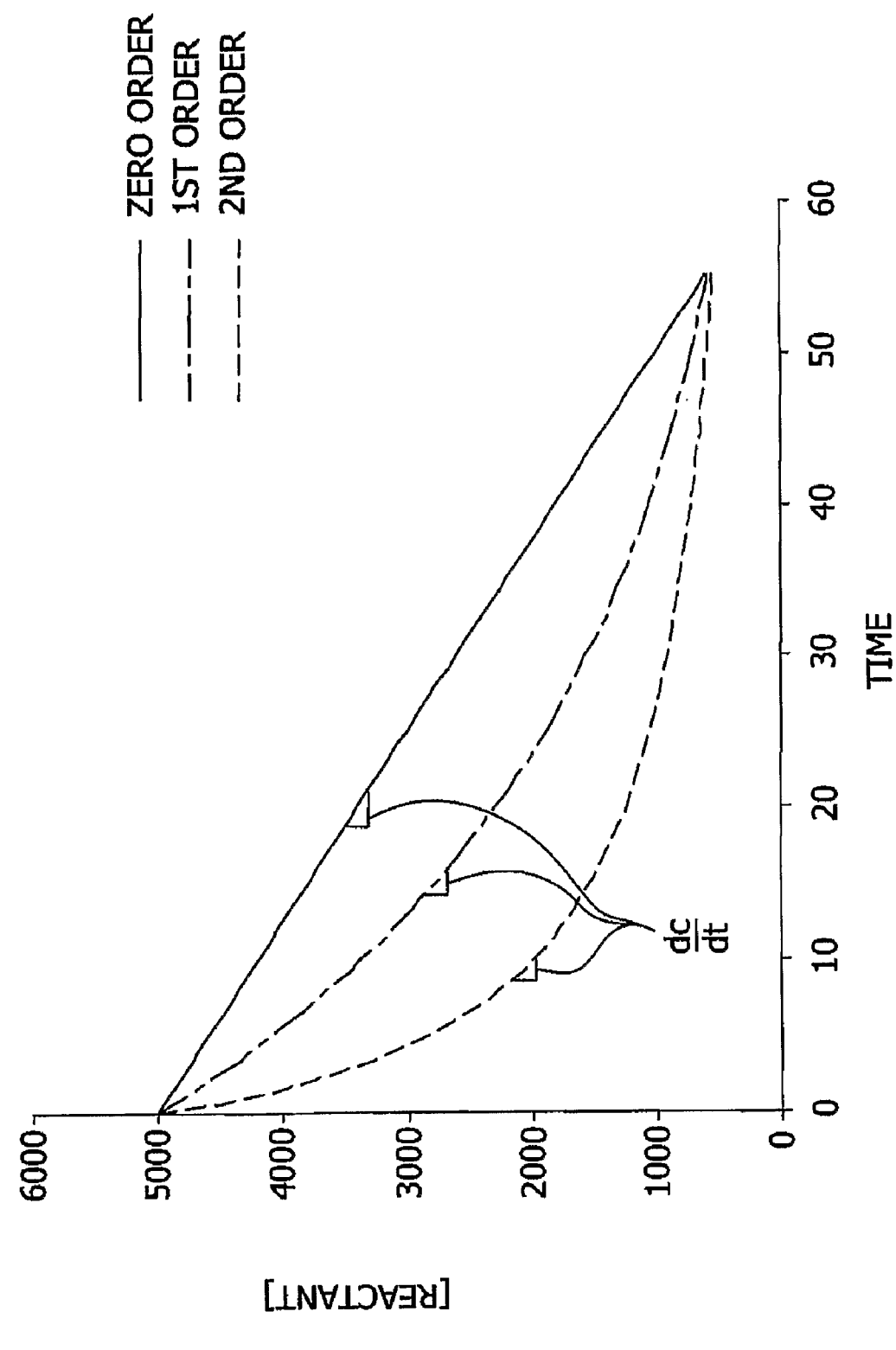
FIG. 5 is a family of plots of residual reactant concentration vs. time in a batch reactor (or vs. distance in a plug flow reactor), with separate curves respectively representing zero order, first order, and second order kinetics, wherein the first derivative of each curve at any given time or location represents instantaneous reaction rate at that time or location.
Figure 6:
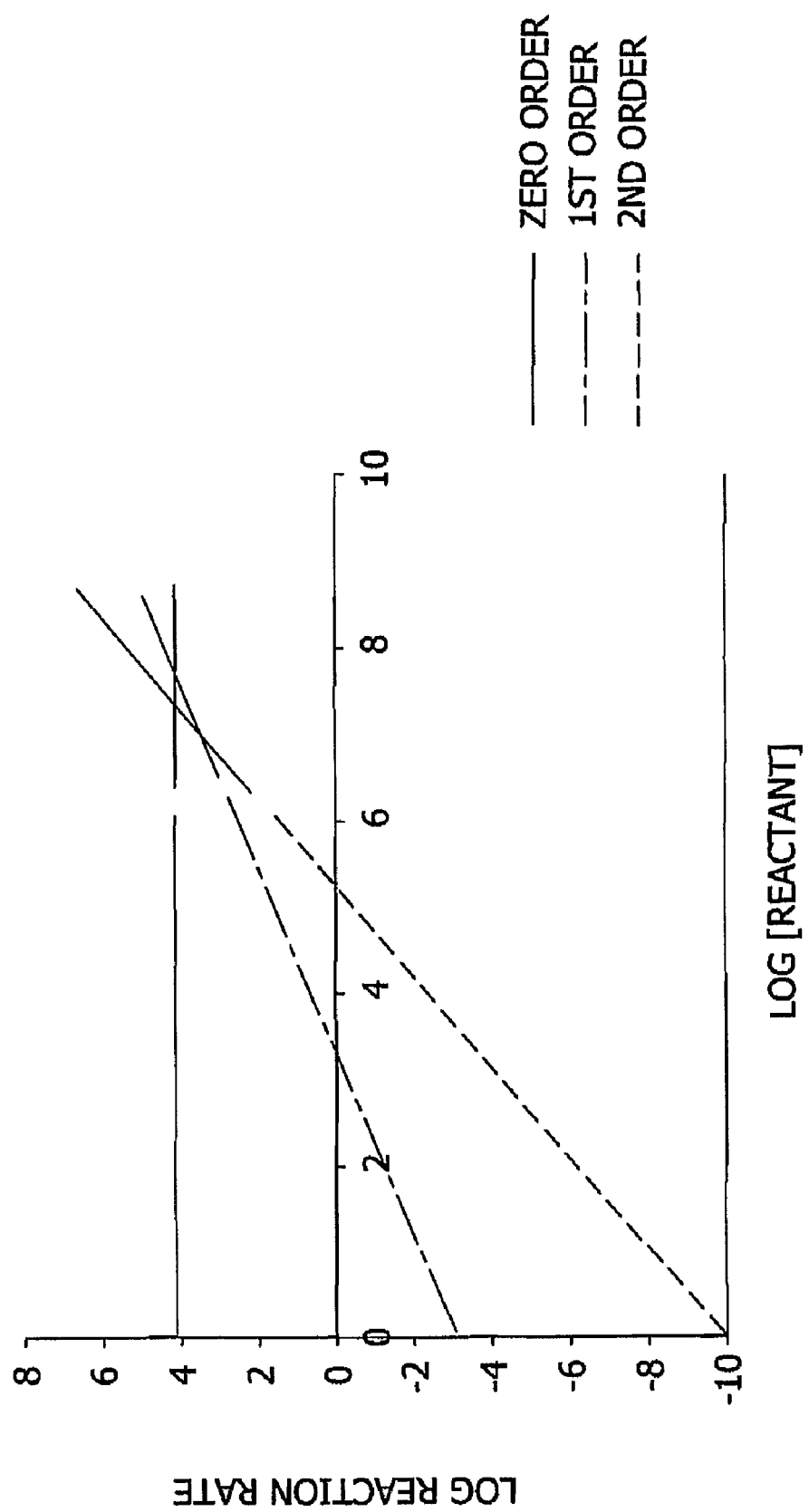
FIG. 6 is a family of plots of the log (reaction rate) vs. log (residual reactant concentration) in a batch reactor (or vs. distance in a plug flow reactor), with separate curves again representing zero order, first order, and second order kinetics.

The order of the reaction and the kinetic rate constant may be determined from a plurality of analyses sufficient to define the contour of the relationship between reaction rate and residual PMIDA concentration. In a plot of residual PMIDA (reactant) concentration vs. time (or vs. distance in a plug flow reactor), as illustrated in FIG. 5, the first derivative at any given time or location represents instantaneous reaction rate at that time or location. In a plot of the log of the reaction rate vs. the log of the residual PMIDA (reactant) concentration, as illustrated in FIG. 6, the slope indicates the order of reaction and the appropriate intercept indicates the rate constant (or, more directly, a pseudo rate constant combining the kinetic rate constant, a dissolved oxygen term and appropriate mass transfer effects).

In a continuous reaction system, FTIR is applied directly for determining conversion, but control can be refined by projecting conversion from FTIR analyses of the reaction medium at a plurality of different residence times. In a flow reactor (e.g., plug flow reactor), analyses at differing residence times may be obtained by applying FTIR to the reaction medium at separate points along the flow path of the reaction medium. Preferably, at least two of such analyses are at points within the zero order regime. Based on a known or determined order of reaction, this allows conversion and residual PMIDA content to be projected, and to be controlled in a predictable manner by adjustment of feed rate, oxygen flow, and/or reaction temperature. In a series of CSTRs, the last reactor operates under terminal conditions, which typically reflect a conversion >95% and are, therefore, ordinarily non-zero order with respect to PMIDA. By comparison of the FTIR analysis of the reaction medium at two different residence times, e.g., where one analysis is made at the exit of the final reactor and another at the exit of the penultimate reactor at steady state, the reaction rate constant can be inferred based on a known or determined order of reaction. The estimate of the rate constant can be refined by separate analyses of samples from the two reactors by laboratory or in-line HPLC. Conversion may thereafter be projected based on continual or repetitive FTIR analyses of the reaction medium exiting the penultimate reactor.

Although FTIR data obtainable during non-zero order reaction conditions are particularly useful in estimating the order and rate of the oxidation reactions, the methods of the invention encompass application of algorithms by which end points are projected from data taken under the zero order or pseudo zero order conditions that typically prevail during more than 95% of a typical batch reaction cycle, or in CSTRs other than the last of a series thereof, or in most of the length or height of a plug flow reactor. As further discussed below, laboratory and plant data may be combined to provide a general algorithm for prediction of end point from data taken at various points in the batch reaction cycle or various positions in a continuous reaction train.

As also discussed below, FTIR analysis can be combined with other methods for monitoring the oxidation reaction to refine the estimate of conversion, e.g., by providing data by which the estimate provided by other methods can be compensated for oxidation of $C_1$ by-products.

Cumulative oxygen consumption may provide a further basis for estimating the extent of conversion of PMIDA. As noted above, the oxidation reactor is preferably operated under pressure control, with the head space of the reactor being vented in response to a pressure sensor to maintain a substantially constant pressure. By measuring the rate of introduction of an oxygen-containing gas of known $O_2$ content, measuring the rate at which the vent gas is removed from the oxidation reaction zone, and analyzing the vent gas for oxygen, the instantaneous rate of oxygen consumption can be determined. By integrating the oxygen consumption rate over time, cumulative oxygen consumption can be determined; and the cumulative oxygen consumption is substantially proportional to PMIDA conversion, as adjusted for formaldehyde and formic acid formation and oxidation, i.e., oxygen consumption is stoichiometrically equivalent to PMIDA conversion and formaldehyde and formic acid formation, according to the relationship:

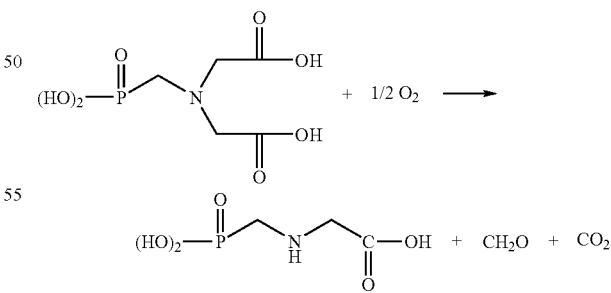

Cumulative oxygen consumption can be compared to the initial PMIDA charge to a batch reactor or to the time integrated rate of PMIDA introduction of a continuous reactor. Adjustment for the generation and oxidation of formaldehyde and formic acid can be made on the basis of on-line analysis for these compounds, or on the basis of historical data. The historical value may be either a fixed figure based on long term statistical analysis of analytical data on the product reaction solution, or an evolutionary value based on statistical analysis of recent historical data, either of recent batches in a batch oxidation process or recent analyses at comparable residence time in a continuous process, in each case under temperature, oxygen flow, oxygen pressure, catalyst charge, etc., which are the same as the batch for which conversion is being estimated. Where a carbon catalyst is used, the formaldehyde and formic acid values are relatively consistent irrespective of catalyst activity, in part because carbon by itself is significantly less effective than a noble metal on carbon catalyst for oxidation of these by-products. A noble metal on carbon catalyst is much more effective for oxidation of $C_1$s, so that the condensed phase $C_1$ content is more dependent on catalyst activity as affected, e.g., by catalyst age and replenishment.

A continuous reactor may also be controlled to maintain a targeted instantaneous ratio of oxygen consumption to PMIDA introduction. The conversion as estimated from cumulative oxygen consumption over a defined period of operation may further be adjusted by any difference in the molar rate at which PMIDA is introduced into the reaction system vs. the molar rate at which the sum of glyphosate and unreacted PMIDA are withdrawn therefrom. Preferably, however, steady state operation is maintained both to preserve process stability generally, and to eliminate any accumulation or decline in working reaction volume as a variable affecting the estimate of conversion.

Where conversion is monitored by oxygen consumption, estimated conversion can be refined on a continuous or repetitive basis by use of an oxygen electrode, which effectively measures the dissolved oxygen content of the aqueous reaction medium, and/or by an oxidation/reduction potential probe, which measures the potential of the catalyst in the medium. Typical traces for $O_2$ flow and dissolved oxygen content of the aqueous medium as a function of time are shown for a typical batch cycle in FIG. 18. Where the rate of oxygen introduction is controlled in response to the oxygen electrode to maintain a constant dissolved oxygen level, it may contribute to the precision of the correlation between oxygen consumption and conversion.

The accuracy with which oxygen consumption is used to estimate conversion and/or residual PMIDA content can be enhanced by combining measurement of oxygen consumption with other methods for determining conversion. For example, a base point PMIDA content can be determined analytically from a sample taken at a relatively high conversion, e.g., in the neighborhood of 95%, and the oxygen consumption measured from the time at which the base point sample is taken. In this manner, error in measurement of cumulative oxygen flow, or arising from consumption of oxygen other than for oxidation of PMIDA, or PMIDA and $C_1$ by-products, is a fraction only of the incremental oxygen requirement for the final stage of conversion rather than a fraction of the total oxygen required for conversion of all PMIDA charged to the reactor. Thus, for example, if the target conversion is 99.0%, and an FTIR or HPLC analysis of sample taken to establish a base point late in the batch indicates a conversion of 94.7%, a 3% error in correlating measured cumulative oxygen consumption with conversion from the base point forward equates to only a ~0.13% error in overall conversion in addition to whatever the error may be in the base point sample analysis.

Such combination of measurements is particularly advantageous because it proceeds from a base point at which residual PMIDA content remains appreciable. Up to this point, the PMIDA analysis remains quite reliable, but cumulative oxygen consumption is subject to significant error. The method then combines a chemical analysis at the base point with determination of oxygen consumption during the final stage of the reaction subsequent to that base point, during which accuracy of residual PMIDA content may typically begin to deteriorate but error in determination of oxygen consumption contributes minimal error to the overall determination. Stated another way, the method is governed by analytical results during the major portion of the reaction in which chemical analysis is the most reliable measure, but switches to oxygen consumption during the closing stages of the reaction wherein oxygen consumption reliability not only is relatively enhanced, but typically also becomes superior to the reliability of chemical analyses.

The method can further be refined by analytical measurement of residual formaldehyde and formic acid throughout the reaction, and particularly subsequent to the high conversion base point. Measurement of any changes in formaldehyde and formic acid content between the base point and an actual or test end point allows the relationship between oxygen consumption and residual PMIDA content to be refined by compensating for the oxygen that may be consumed in the oxidation of the $C_1$ by-products. Although the accuracy of analytical methods such as FTIR for PMIDA deteriorates at high conversions, the accuracy of analyses of formaldehyde and formic acid remains quite high. Moreover, because formaldehyde and formic acid are being both consumed and generated during the reaction, including the final stage subsequent to the base point, the residual level of residual $C_1$ compounds is typically greater than that of residual PMIDA at the desired end point, further contributing to the accuracy of analyses for these by-products by FTIR, HPLC or other appropriate technique.

Practice of the combined method with $C_1$ compensation is further elaborated below with respect to the heat generation method for assessing conversion and estimated reaction end point. The reaction can be monitored after the high conversion base point by either oxygen consumption, heat generation or $CO_2$ generation. $C_1$ compensation after the base point operates on substantially the same principle in all of these methods, with further particulars being provided below in connection with heat generation.

The declining rate of oxygen consumption at low PMIDA concentrations may provide another or further basis for refining the estimate based on cumulative oxygen consumption, and/or afford an independent basis for estimating the residual PMIDA content toward the end of a batch reaction cycle or in the last of a series of CSTRs. The oxidation of PMIDA to glyphosate is fundamentally first order in PMIDA, or approximately so. During the bulk of the reaction, where PMIDA content is high, the reaction rate is limited by mass transfer of oxygen to the aqueous phase. However, towards the end of the reaction, typically at PMIDA conversions in excess of 98%, kinetics become limiting and first order behavior is observed. The oxidations of formaldehyde to formic acid and formic acid to carbon dioxide are also non-zero order reactions. The proper exponents for a particular reaction system in a given range of conversion can be derived for each substrate, i.e., PMIDA, formaldehyde and formic acid by empirical observation, kinetic studies and statistical analysis. The kinetic rate constants for each reaction can be derived from a combination of laboratory data and industrial reactor data comparing oxygen consumption with PMIDA, formaldehyde and formic acid analyses of a series of samples taken during non-zero order operations, i.e., under conditions in which the reaction rate is declining. From data establishing the order of the respective reactions and applicable rate constants, the residual PMIDA content may be inferred from a comparison of the initial batch PMIDA charge, or rate of introduction of PMIDA into a continuous reaction system, vs. the residual rate of oxygen consumption at substantially constant dissolved oxygen concentration during non-zero order reaction, either at the end of a batch reaction cycle or in the final of a series of CSTRs. To the extent that the behavior of the several oxidation reactions approximates first order, a component of the instantaneous oxygen consumption rate is directly proportional to the residual PMIDA content, a further component is directly proportional to residual formaldehyde, and a still further component is directly proportional to residual formic acid. If the reactions are essentially first order and the respective rate constants are known, a relatively simple algorithm may be developed for determining residual PMIDA content as a function of instantaneous oxygen consumption. To the extent that the order of any of the various reactions differs from first order, the determination of residual PMIDA content from instantaneous oxidation rate becomes more complex. However, where the orders of the reactions are reasonably established from historical laboratory and/or industrial scale data, rigorous equations and/or statistical correlations can be developed by which to sort out residual PMIDA from the instantaneous oxygen consumption rate. In the case of a series of CSTRs, the differential oxygen consumption rate method may be calibrated by estimating the kinetic rate constant or function thereof from PMIDA analysis of samples of the aqueous medium entering and exiting the final reaction zone. At either conventional conversions or in the production of a product reaction mixture of exceptionally low PMIDA content, the reaction occurring in the final stage reaction zone of a continuous oxidation process is ordinarily non-zero order. As in the case of $C_1$ compensation as discussed above, the historical data may be based either on long term statistical analysis, or reflect evolutionary values based on analysis of recent performance. Sampling may also provide the basis for estimating the kinetic rate constants for the oxidation of formaldehyde and formic acid. Based on data defining the orders of the various reactions and the respective rate constants, oxygen consumption associated with $C_1$ oxidation can also be estimated in a continuous system, allowing residual PMIDA to be determined from the balance of the oxygen consumption.

Once a base line has been established, the value of the rate constant can be adjusted based on variation in the rate of decline of oxygen consumption from the point at which non-zero order behavior is observed, i.e., from the (negative) first derivative of oxygen consumption rate, the absolute value of which is inversely related to the rate constant. Also, as the catalyst ages and its activity significantly declines, the effect on first order rate constants can be periodically re-calibrated by renewed sampling of the final reaction zone, or near the end of the batch. See the derivation set forth below for determination of the rate constant by analysis of declining reaction rate as measured by heat generation. The same analysis is applicable to oxygen consumption, substituting this term for heat generation in the derivation.

In a batch reaction, a function of the rate constant and the order of the reaction may also be established from a plurality of measurements of instantaneous oxygen consumption, substantially as described above with respect to FTIR. If instantaneous oxygen consumption is monitored in combination with analyses of the reaction solution, e.g., using FTIR or HPLC, and the actual residual PMIDA content determined as a function of instantaneous oxygen consumption at one or more points during the non-zero order oxidation stage, plural measurements of instantaneous oxygen consumption during this stage may be used to project a desired end point of a batch reaction, also as described above with respect to FTIR. Conversion in the final CSTR of a series thereof can be projected based on measurement of instantaneous oxygen consumption relative to PMIDA feed rate in the reactors upstream of the final reactor, and residence time in the final reactor. In this instance, the order of the reaction may be separately determined from historical analytical or operational data obtained from a laboratory or industrial batch reactor.

As further discussed below, oxygen consumption can be combined with other methods for monitoring the reaction to refine the estimate of conversion. For example, HPLC, FTIR, or electrochemical oxidation analyses can be used to compensate for consumption of oxygen for $C_1$ oxidation.

A further alternative for estimation of PMIDA conversion comprises measurement of cumulative carbon dioxide generation. In the oxidation reaction, one carboxymethyl group is removed and converted to carbon dioxide or a combination of carbon dioxide and other $C_1$ compounds, i.e., formaldehyde and formic acid. Thus, PMIDA conversion is directly proportional to the molar sum of cumulative $CO_2$ generation plus formaldehyde and formic acid generation and oxidation. By measurement of cumulative $CO_2$ generation and adjustment for other $C_1$ compounds, an estimate can be made of the conversion of PMIDA. Adjustment for formaldehyde and formic acid obtained in the reaction can be determined on essentially the basis described above for estimation of PMIDA conversion by oxygen consumption. Also as in the case of oxygen consumption, the conversions estimated from cumulative heat generation in a continuous reaction system may be adjusted by any difference in the molar rate at which PMIDA is introduced into the reaction system vs. the molar rate at which the sum of glyphosate and unreacted PMIDA are withdrawn therefrom.

Further as described above with respect to cumulative oxygen consumption, the accuracy with which cumulative carbon dioxide generation is used to estimate conversion and/or residual PMIDA content can be enhanced by combining measurement of $CO_2$ generation with other methods for determining conversion. For example, a base point PMIDA content can be determined analytically from a sample taken at a relatively high conversion, and $CO_2$ generation measured from the time at which the base point sample is taken. As in the case of determining conversion and/or end point from oxygen consumption, error in measurement of cumulative $CO_2$ release, or arising from $CO_2$ generation other than from oxidation of PMIDA, or PMIDA and $C_1$ by-products, is a fraction only of the incremental $CO_2$ generation during the final stage of conversion subsequent to the base point rather than a fraction of the total $CO_2$ generated in the conversion of all PMIDA charged to the reactor.

This combined method enjoys the same advantages as the combined analytical and oxygen consumption method as described above. Thus, it is governed by chemical analysis up to the high conversion base point during which such analysis is the most reliable, then switches at the base point to cumulative $CO_2$ over the final stage of the reaction, during which the latter method typically provides accuracy superior to that of chemical analysis.

In this combined method, compensation for formation and consumption of formaldehyde and formic acid can be accomplished in the same manner as generally described above with respect to the oxygen consumption method, and elaborated below with respect to the heat generation method.

Figure 20:
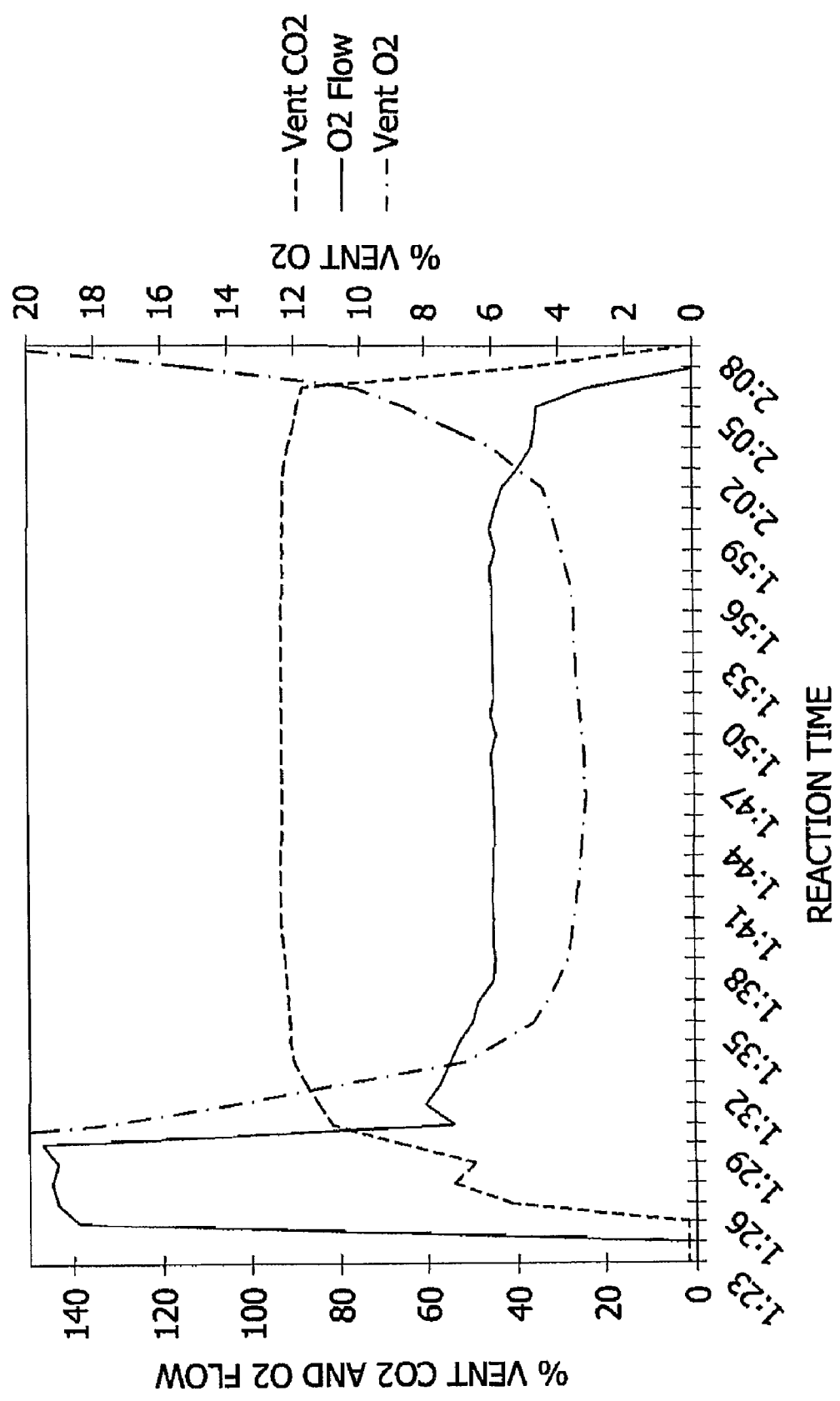
FIG. 20 shows the profile of $O_2$ and $CO_2$ content of the reactor vent gas vs. time during batch oxidation of PMIDA to glyphosate.
Figure 21:
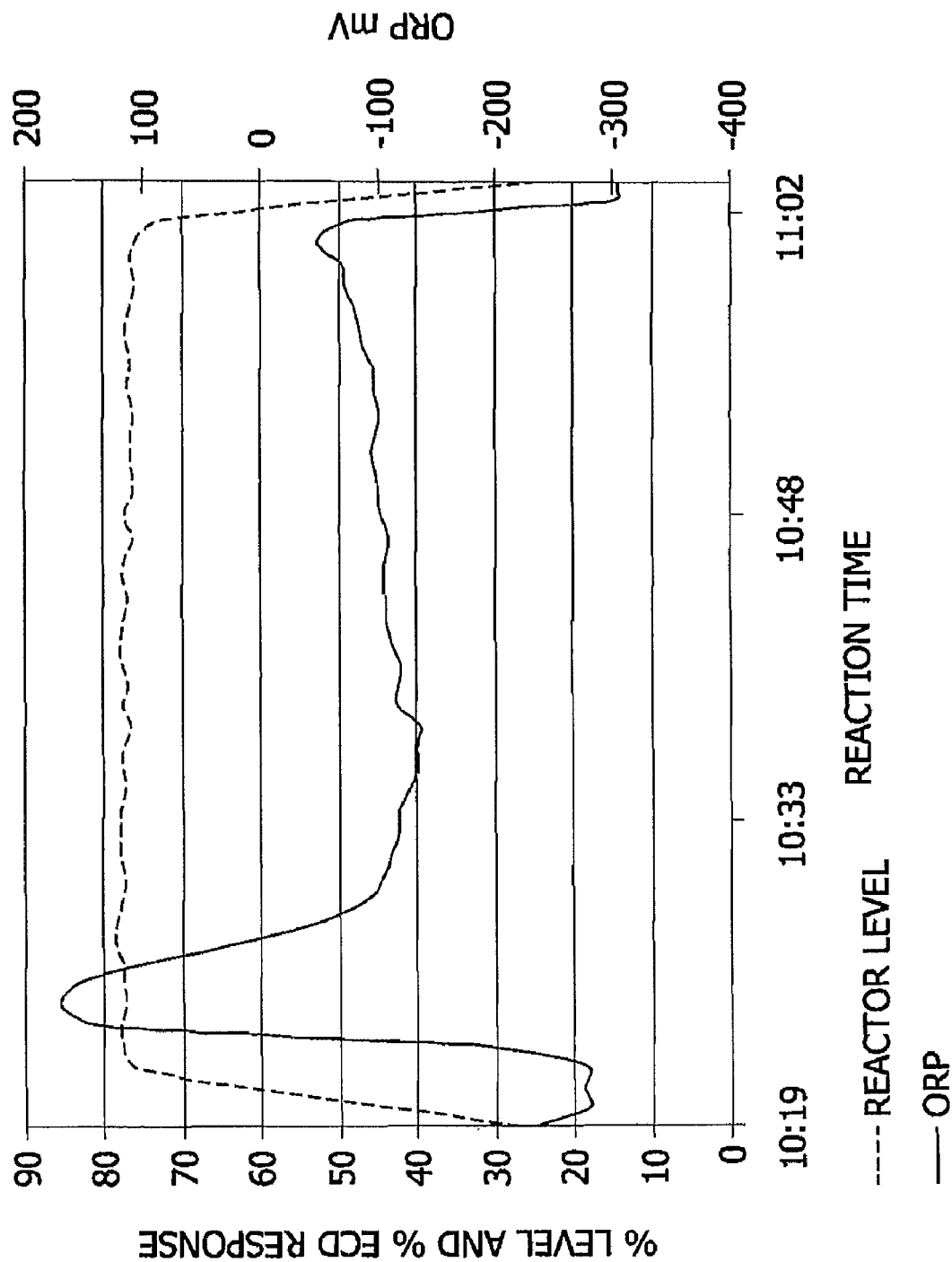
FIG. 21 shows the oxidation/reduction potential profile during batch oxidation of PMIDA to glyphosate.

Also, as in the case wherein conversion is estimated from cumulative oxygen consumption, the estimate based on cumulative $CO_2$ generation may be refined, or the residual PMIDA content independently monitored, by measuring the declining $CO_2$ generation rate during the closing portion of a batch reactor, or under the terminal conditions prevailing in the last of a series of CSTRs. If the rate of oxygen addition is controlled to maintain a constant oxygen potential in response to an ORP electrode, and/or a constant dissolved oxygen content in response to an oxygen electrode, the accuracy of the estimate based on $CO_2$ generation is enhanced in essentially the same way that the accuracy of an estimate based on oxygen consumption is enhanced. FIG. 20 illustrates typical profiles of oxygen content and carbon dioxide content in the vent gas as a function of time during the batch catalytic oxidation of PMIDA to glyphosate; and FIG. 21 shows similar profile for oxidation/reduction potential during the batch.

Since the reaction is first order in PMIDA, the residual PMIDA content may also be inferred from a comparison of the initial batch PMIDA charge, or rate of introduction of PMIDA into a continuous reaction system, vs. the residual instantaneous rate of carbon dioxide generation, especially at constant dissolved oxygen concentration, either at the end of a batch reaction cycle or in the final of a series of CSTRs. For purposes of this alternative, the kinetic rate constant or a function thereof may be estimated and updated in essential the same manner as is described above for the estimation of PMIDA conversion from the rate of decline in the consumption of oxygen. More particularly, the rate constant can be determined according to the derivation set forth below with respect to heat generation, but substituting carbon dioxide generation for heat generation.

In a batch reaction, a function of the rate constant and the order of the reaction may also be established from a plurality of measurements of instantaneous $CO_2$ generation, substantially as described above with respect to oxygen consumption and FTIR. If $CO_2$ generation is monitored in combination with analyses of the reaction medium, e.g., using FTIR or HPLC, and the actual residual PMIDA content determined as a function of instantaneous $CO_2$ generation at one or more points during the non-zero order oxidation stage, plural measurements of instantaneous $CO_2$ generation during this stage may be used to project a desired end point of a batch reaction, also as described above with respect to FTIR. Conversion in the final CSTR of a series thereof can be projected based on measurement of instantaneous $CO_2$ generation relative to PMIDA feed rate in the upstream reactors and residence time in the final reactor. In this instance, the order of the reaction may be separately determined from historical analytical or operational data obtained from a laboratory or industrial batch reactor.

As further discussed below, carbon dioxide generation can be combined with other methods for monitoring the reaction to refine the estimate of conversion. For example, HPLC and FTIR analyses can be used to compensate for generation of $CO_2$ from $C_1$ oxidation.

In a further alternative embodiment, PMIDA conversion can be estimated from a combination of the oxygen consumption and carbon dioxide generation. Although each independently provides a basis for estimation, each may also be used as a check against the other. Moreover, observations of oxygen consumption, carbon dioxide generation, FTIR analysis, and other parameters may be integrated into a chemometric model which also integrates other data relationships such as, for example, material and energy balance computations for the reaction step. Such a model can also optionally integrate data yielded by other methods of end point detection as described hereinbelow, including cumulative heat generation, differential heat generation, and electrochemical oxidation.

As illustrated in FIG. 20, the oxygen content of the reactor vent gas typically increases rather sharply as the end point of a batch oxidation reaction cycle is approached. Data underlying the profiles illustrated in FIG. 20 provide the basis for determining both cumulative and differential oxygen consumption in the oxygen consumption methods of the invention for estimating end point. In addition, given the strong response of vent gas $O_2$ content to conversion as the reaction nears its end point, the instantaneous vent gas $O_2$ content as such, or the rate of change therein, provides a reasonably precise basis for projecting a reaction end point, or estimating the extent of conversion, irrespective of whether the measured $O_2$ content is converted to a cumulative oxygen consumption or an instantaneous rate thereof. Historical analytical or operational data obtained from laboratory or industrial oxidation reactors may be used to calibrate detection of the reaction end point by measuring vent gas $O_2$ content. Conversions and end points as estimated from vent gas oxygen profiles can provide a basis for adjusting reaction parameters such as PMIDA residence time, reaction temperature, and agitation intensity in establishing and maintaining a target residual PMIDA content in the product reaction solution exiting a continuous back mixed or continuous plug flow reactor.

As illustrated in FIG. 20, vent gas $O_2$ may be relatively high early in the course of a batch reaction, typically before the aqueous reaction medium has become heated to the target reaction temperature. In such instance, the target end point or conversion is indicated by vent gas $O_2$ content as attained after an appropriate minimum batch reaction time or minimum continuous reactor residence time. The requisite minimum time is that which is sufficient so that, under the conditions prevailing in the reaction zone, there is a unique correlation between $O_2$ content of the vent gas vs. conversion and/or residual PMIDA content in the course of further reaction subsequent to such minimum reaction time or residence time. For example, the vent gas can be monitored after the reaction has entered the non-zero order stage with respect to consumption of PMIDA, typically at a conversion above about 95%, or even above 98%. However, the "minimum time" requirement can often be met earlier. Under typical reaction conditions, the vent gas $O_2$ content may become a unique function of conversion after a minimum reaction or residence time that provides a conversion somewhat below 95%, in which case it may be convenient to begin following vent gas $O_2$ content at a such lower conversion.

In a typical tank reactor, whether batch or CSTR, the head space is substantially back mixed, and the volume and residence time in the head space can be substantial, thus potentially damping the response of the vent gas $O_2$ content to conversion if measured by sampling the bulk gas phase, and consequently tending to mask the end point. Thus, in certain preferred embodiments, the response is enhanced by monitoring the $O_2$ content of gas phase instantaneously as it exits or evolves from the liquid phase. This may typically be accomplished, e.g., by segregating a representative sample of the aqueous liquid reaction medium, and directing the sample to a gas/liquid separator operating at the same pressure as the reactor, whence the separating gas phase is analyzed for $O_2$ content. The sample is withdrawn from below the liquid level and the gas/liquid separator may be vented back into the head space of the reactor. Alternatively, an analytical probe may be immersed in the liquid phase which is effective for sensing nascent gas released from the liquid phase. In yet another alternative, a sampling device may be positioned to capture bubbles forming in the liquid phase and direct it to a gas chromatograph or other analytical device for determining the oxygen content.

Where a noble metal catalyst is used for the reaction, the oxygen flow rate may in some cases be stepped down significantly as the reaction approaches its end point, e.g., toward the end of a batch reaction cycle or in the final reactor in a series of CSTRs. This creates conditions that are conducive to the oxidation of $C_1$ by-products such as formaldehyde and formic acid, helps prevent oxidation of glyphosate to AMPA, and inhibits oxidative degradation of the catalyst. Where such measures are taken, the instantaneous $O_2$ content of the vent gas may not increase as sharply as may be desired for precise end point identification. However, even at reduced oxygen flow, the oxygen utilization may drop relatively sharply as the batch approaches its end. Thus, end point can also be detected by the instantaneous oxygen utilization, or the rate of change therein, in a manner that is otherwise substantially similar to detection by vent gas $O_2$ per se.

Oxygen utilization is preferably determined by comparing the oxygen flow rate to the reactor with the product of the vent gas flow rate and the vent gas $O_2$ content as determined in the gas phase exiting the liquid phase. For the latter determination, a segregated sample is preferably used to produce a segregated vent gas sample that is analyzed for $O_2$. Alternatively, a probe immersed in the liquid phase can be used as described above.

Similarly, as further demonstrated in FIG. 20, the $CO_2$ content of the vent gas falls sharply in the last few minutes before the typical end point. Thus, as an alternative to using the data reflected by the $CO_2$ vent gas profile in the aforesaid cumulative and instantaneous $CO_2$ generation methods (or in combination therewith), the instantaneous $CO_2$ content of the vent gas, and/or the rate of change thereof, may itself provide a useful end point indication for the reaction system. Historical analytical data may be used in the same manner to calibrate end point detection by vent gas $CO_2$ content as described above for vent gas $O_2$ content. Application of $CO_2$ content end point detection to batch, continuous back mixed and continuous plug flow systems is also the same as for vent gas $O_2$ content as described above, including the methods described for isolating a sample of the vent gas evolving from the liquid phase or use of a probe immersed in the aqueous liquid. Further refinement of end point may be realized by following both vent gas $O_2$ content and vent gas $CO_2$ content. Either may be used to cross check and/or adjust the other.

Figure 18:
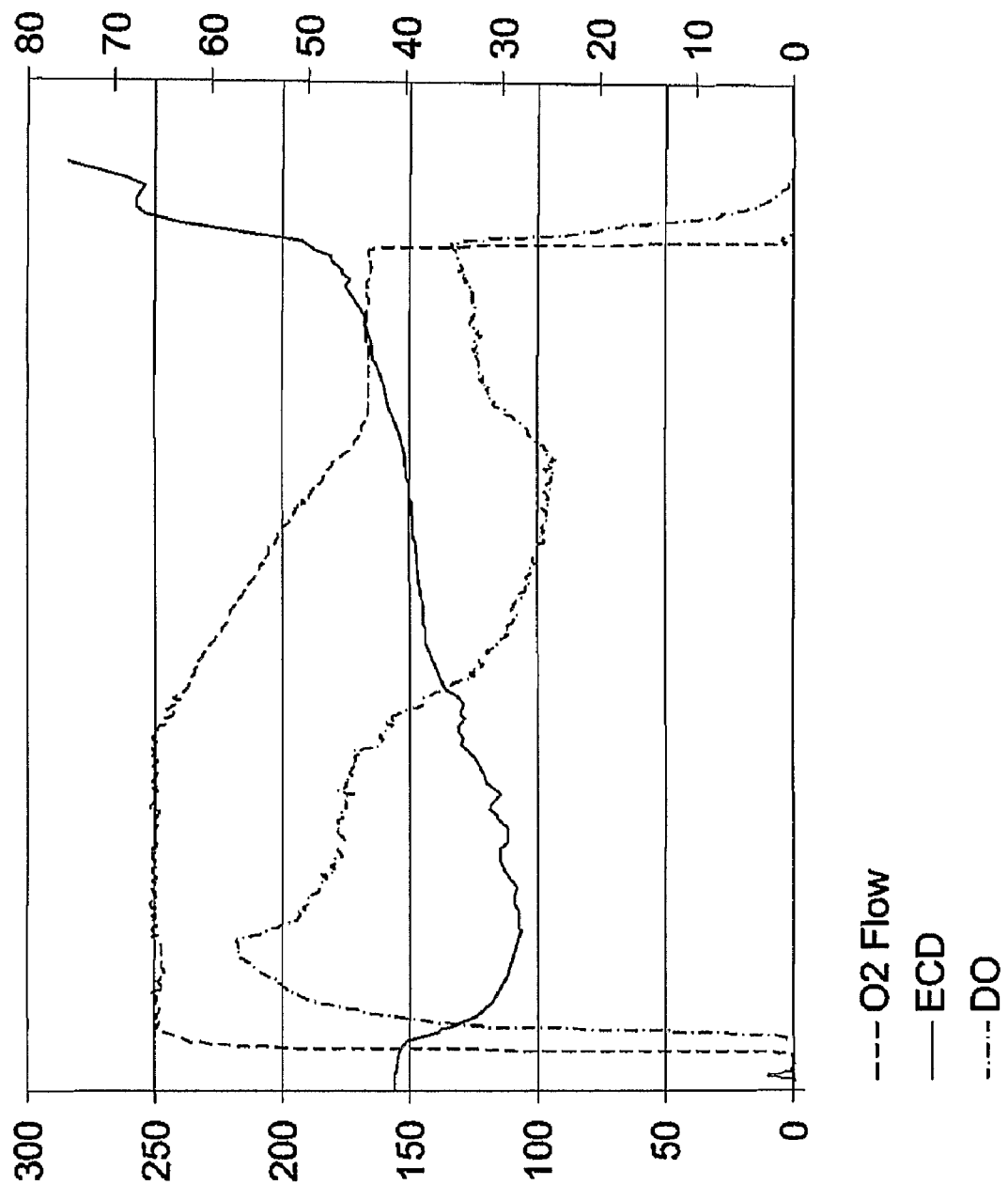
FIG. 18 shows profiles of dissolved oxygen content, oxygen flow and voltage required to maintain a constant current in a select current method of electrochemical end point detection during a batch oxidation of PMIDA to glyphosate.

As further illustrated in FIG. 18, dissolved oxygen content of the aqueous reaction medium may also be used in the manner immediately described above for vent gas $O_2$ and/or $CO_2$ content in identifying end points at which residual PMIDA concentration has been reduced to a desired level. In the particular operations illustrated, a sharper response may be observed in the vent gas $O_2$ and $CO_2$ content, as compared to dissolved oxygen. As noted, oxygen flow rate is typically reduced during the final minutes of reaction to minimize AMPA formation and avoid oxygen poisoning of a noble metal catalyst, and this can damp the effect of declining reaction rate on dissolved oxygen. However, depending on the selection of catalyst and other conditions imposed on the process, a reasonably sharp end point identification may be obtained by monitoring this variable. Like the other methods, end point detection by dissolved oxygen level may be calibrated by comparison to historical FTIR or HPLC analytical data obtained in a laboratory or industrial oxidation reactor.

In accordance with a further alternative method of the invention, the conversion of PMIDA can be monitored and/or an end point defined by a target residual PMIDA concentration can be projected based on in-line FTIR or HPLC analysis for one or more products of over-oxidation such as, for example, aminomethylphosphonic acid ("AMPA"). Based on synthesis of historical analytical data obtained from operation of a laboratory or industrial scale oxidation reactor, a fundamental or empirical correlation can be developed between AMPA accumulation and conversion. Such correlation may vary depending on whether the reaction system comprises a batch reactor, a series of continuous back mixed reactors, or a plug flow reactor. Based on the same or similar data, a correlation may also be developed between AMPA accumulation and reaction time for a batch reactor, especially toward the end of the reaction cycle; or AMPA accumulation as function of residence time in the last of a series for a continuous back mixed reactors or at the exit of a plug flow reactor. Combining a correlation of PMIDA content vs. AMPA content with a correlation of AMPA content vs. time, an end point projection algorithm may be developed based on measured AMPA content. If AMPA response is sharper than PMIDA response, the precision of end point detection may be enhanced vs. a method based on direct analysis for PMIDA alone. Conversion and end point projections based on accumulation of AMPA, or other over-oxidation products, can be compared with data from other methods for conversion monitoring as discussed herein, and the comparison integrated into a general program for estimating and cross checking such projections.

According to a further alternative, the PMIDA conversion and/or reaction end point can be monitored or determined by the electrochemical response of the aqueous reaction medium to an imposed current or imposed voltage. In such methods, a potential is imposed between a working electrode and counterelectrode, both electrodes being immersed in the aqueous reaction medium or a sample thereof. An estimate of the extent of conversion and of residual PMIDA content can be determined from a function of the power that is consumed in maintaining a select current density or select potential difference between the electrodes. The methods are based on the difference in the potential required for the electrochemical oxidation of PMIDA, which is relatively low, vs. the potential required for oxidation of glyphosate, which is relatively high. At low to moderate conversions, the current flows between the electrodes at a voltage effective for the electrochemical oxidation of PMIDA, but insufficient for the electrochemical oxidation of glyphosate. When PMIDA is sufficiently depleted, the current flow either sharply declines, or is substantially shifted to electrochemical oxidation of glyphosate. In either case, the current/voltage relationship changes so that greater power consumption is required to maintain a given current density.

In one alternative for electrochemical detection or monitoring of the conversion of PMIDA, a select current density is maintained between the electrodes, and the voltage required to maintain that current density is continuously or intermittently measured. The select current density maintained between the electrodes immersed in the aqueous reaction medium or a sample thereof is preferably held substantially constant, but optionally may be a programmed current density, e.g., a series of discrete current densities or a current scan. Extinction of PMIDA to a target residual level is detected by a rise in voltage necessary to maintain the select current density. The voltage that is necessary to maintain the select current density at the target PMIDA content is essentially the potential required for oxidation of PMIDA, plus an increment necessary to overcome the resistivity of the solution between the electrodes and any fouling or other source of polarization at the electrodes. Because the $C_1$ by-product compounds formaldehyde and formic acid are subject to electrochemical oxidation at a potential lower than that required for oxidation of PMIDA, the imposed or select current density is the sum of that sufficient for oxidation of the $C_1$s and possibly other readily oxidizable impurities, plus an increment that provides the Faradaic equivalent of a target PMIDA concentration. During operation at high to modest PMIDA concentration, the current density is carried entirely by the oxidation of $C_1$s, other readily oxidizable impurities and PMIDA; and the voltage stays relatively constant at a level slightly above the potential required for PMIDA oxidation. As the PMIDA concentration drops below the target threshold, the sum of the oxidation products of $C_1$, other readily oxidizable impurities and PMIDA is no longer sufficient to carry the select current density, and the voltage increases to the potential required for oxidation of glyphosate. In a batch reaction, this end point may be identified by a sharp inflection in a plot of voltage vs. time, e.g., as presented on a process operations control chart.

As further discussed herein, "select current density" and "current density" are sometimes referred to as "select current" and "current," respectively. At a voltage sufficient for electrooxidation of PMIDA but not glyphosate, the sum of the PMIDA and $C_1$ content is a function of current density rather than absolute current, because the current density is a function of the absolute current and the scale and geometry of the electrolytic circuit. The circuit, it depends on the area and orientation of the electrodes presented to the solution in the electrolytic circuit. Those skilled in the art will recognize that, in the practical application of the method of the invention in a manufacturing facility, once the structure of the circuit and circuit elements, including electrodes, is fixed, the variable actually imposed and controlled, and against which the requisite voltage is measured and displayed, may be the current rather than current density. But for the same reasons, once the scale, structure and geometry of the system is fixed, selection of current is tantamount to selection of current density.

Figure 7:
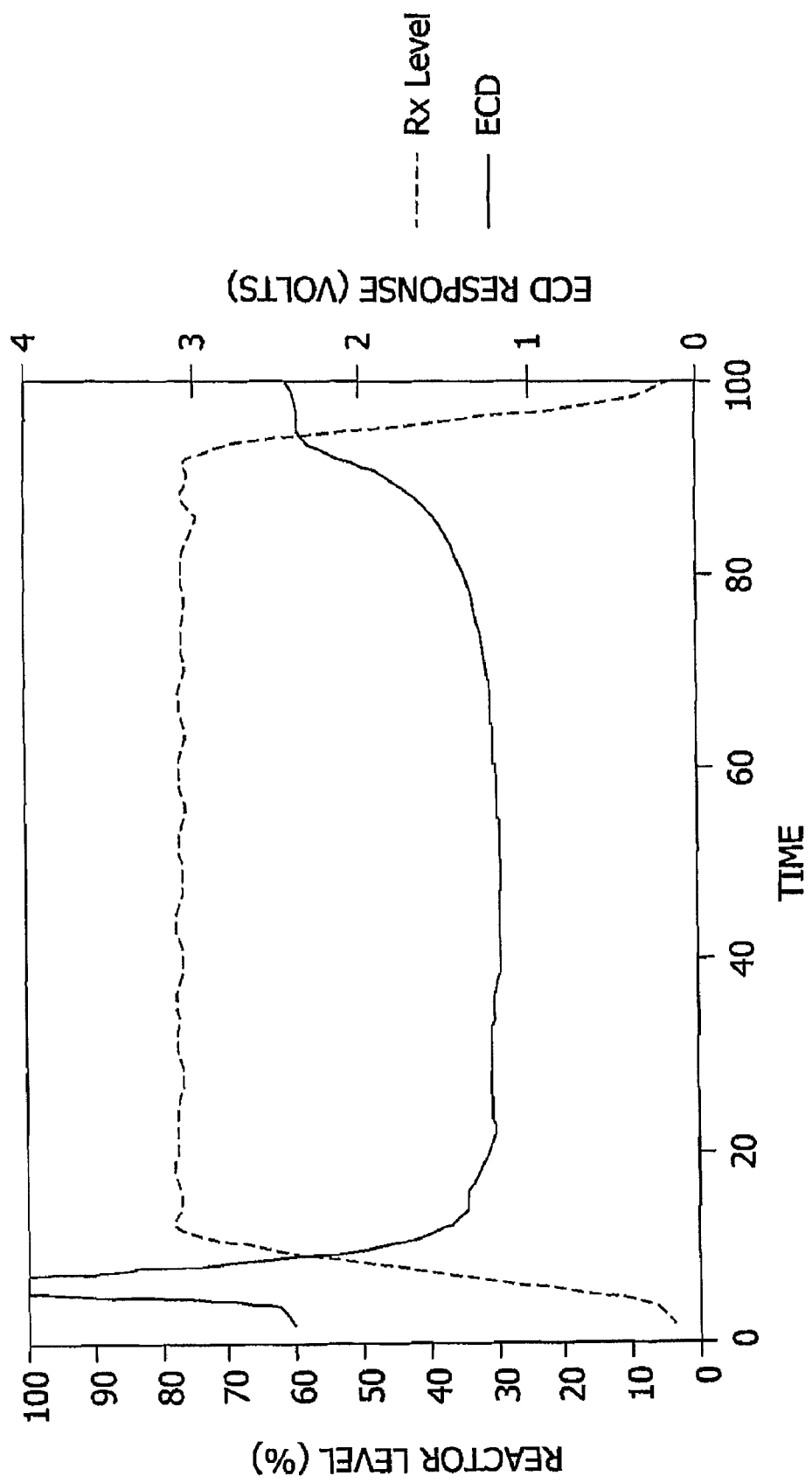
FIG. 7 is a trace from a process control chart comprising a plot of voltage vs. time at a constant current in an electrochemical oxidation method for estimating the residual PMIDA content during the catalytic oxidation of PMIDA to glyphosate, and/or the end point of the catalytic oxidation reaction.
Figure 8:
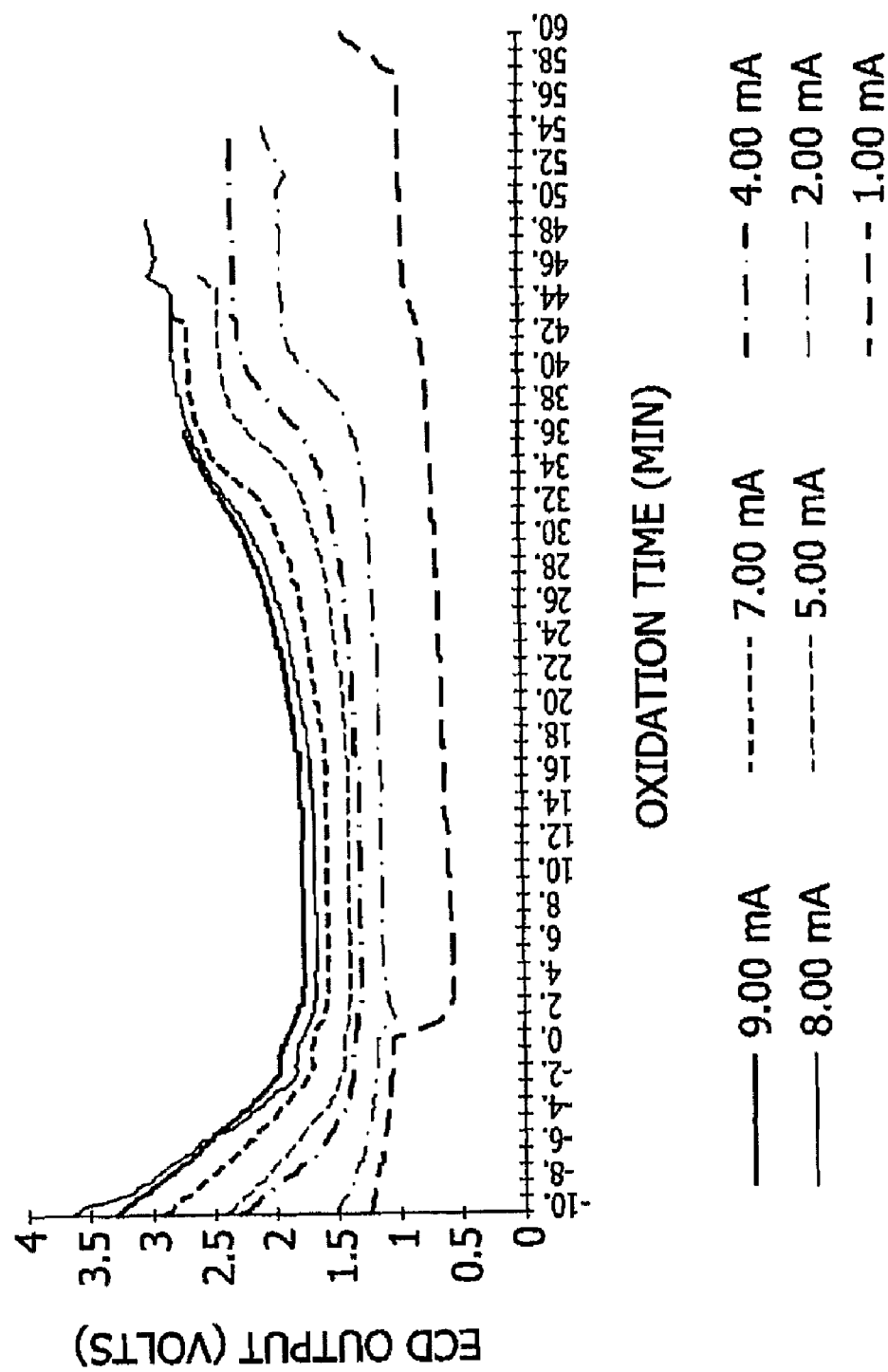
FIG. 8 comprises voltage vs. time plots similar to FIG. 7, but shows a series of voltage vs. time curves for different select currents.

A plot of voltage vs. time (and conversion) at constant current density is illustrated in FIG. 7. This is illustrative of the readout obtained from a process instrument used for monitoring PMIDA conversion and/or estimating or identifying a desired end point. FIG. 8 comprises a series of voltage vs. time and conversion plots of the type that may be used in selection of programmed current that is most effective for detecting the desired end point/degree of conversion. In FIG. 8, voltage is recorded as a function of time at a variety of different select current densities. It will be seen that if the select current density is too high, solution impedance obscures the effect of electrochemical oxidation, and a sharp inflection is not observed when the PMIDA concentration drops to a target value. A lower current, on the other hand, is potentially effective for identifying a very low target residual PMIDA content, and thus a high conversion. However, if the current is too low, the end point may be obscured by the background current or be carried entirely by oxidation of formaldehyde, formic acid and various readily oxidizable impurities. Thus, if too low a current is used in end point detection, it may result in the catalytic oxidation reaction cycle being prolonged to the extent that a risk of overreaction is incurred, i.e., oxidation of product glyphosate to AMPA. In the plot in question, the optimal current is between about 4 and about 7 milliamps.

More generally, it is preferred that the select current density be in the range between about 0.1 and about 0.7 mA/mm², preferably between about 0.2 and about 0.5 mA/mm² at the working electrode, i.e., the anode. Thus, for example, where the electrodes comprise parallel pins of about 1.5 mm diameter×3-5 mm in length, the preferred current may typically fall in the 4 to 7 mA range indicated as optimal in FIG. 8. In order to minimize the effect of solution resistivity, the electrodes are preferably spaced between about 1 mm and about 4 mm apart, preferably about 2 to about 3 mm apart. Advantageously, the flow rate of reaction solution between the electrodes is maintained at a least about 100 cm/sec, more typically between about 30 and about 300 cm/sec to minimize fouling and polarization and to maintain a representative solution around the electrodes.

Subject to the sensitivity limitations indicated in FIG. 8, to variability in the $C_1$ concentration at the end of the batch, and to the predictability of $C_1$ variations, the select current method may be tuned to identify essentially any target end point for a batch reaction. For example, a constant current electrochemical detection system may be set to identify an end point of 450 to 600 ppm PMIDA for standard operations or in the range of 45 to 60 ppm where an exceptionally low PMIDA product is desired. Where the process comprises recycle of the PMIDA from the glyphosate product recovery area to the reaction system, the target end point may be increased by an increment corresponding to the extent of the recycle. For example in a continuous process of the type illustrated in FIGS. 1 and 2, the target end point may typically be from about 500 to about 2500 ppm PMIDA for standard operations, or in the range of about 250 ppm PMIDA under conditions where an exceptionally low PMIDA product is desired.

In a continuous process, select current may be established in a stream of sample of the product reaction solution in or exiting the final reactor. If the voltage required to maintain the imposed current approaches or exceeds the potential required for electrochemical oxidation of glyphosate, the target PMIDA has been reached; if not, there may still be too much unreacted PMIDA. A more specific determination of actual PMIDA content can be obtained by scanning the current and observing the voltage, subtracting the component attributable to $C_1$s as achieved at voltages below the threshold potential for electrochemical oxidation of PMIDA, and estimating residual PMIDA from the Faraday equivalent of the current increment in excess of that required for $C_1$s.

Figure 17:
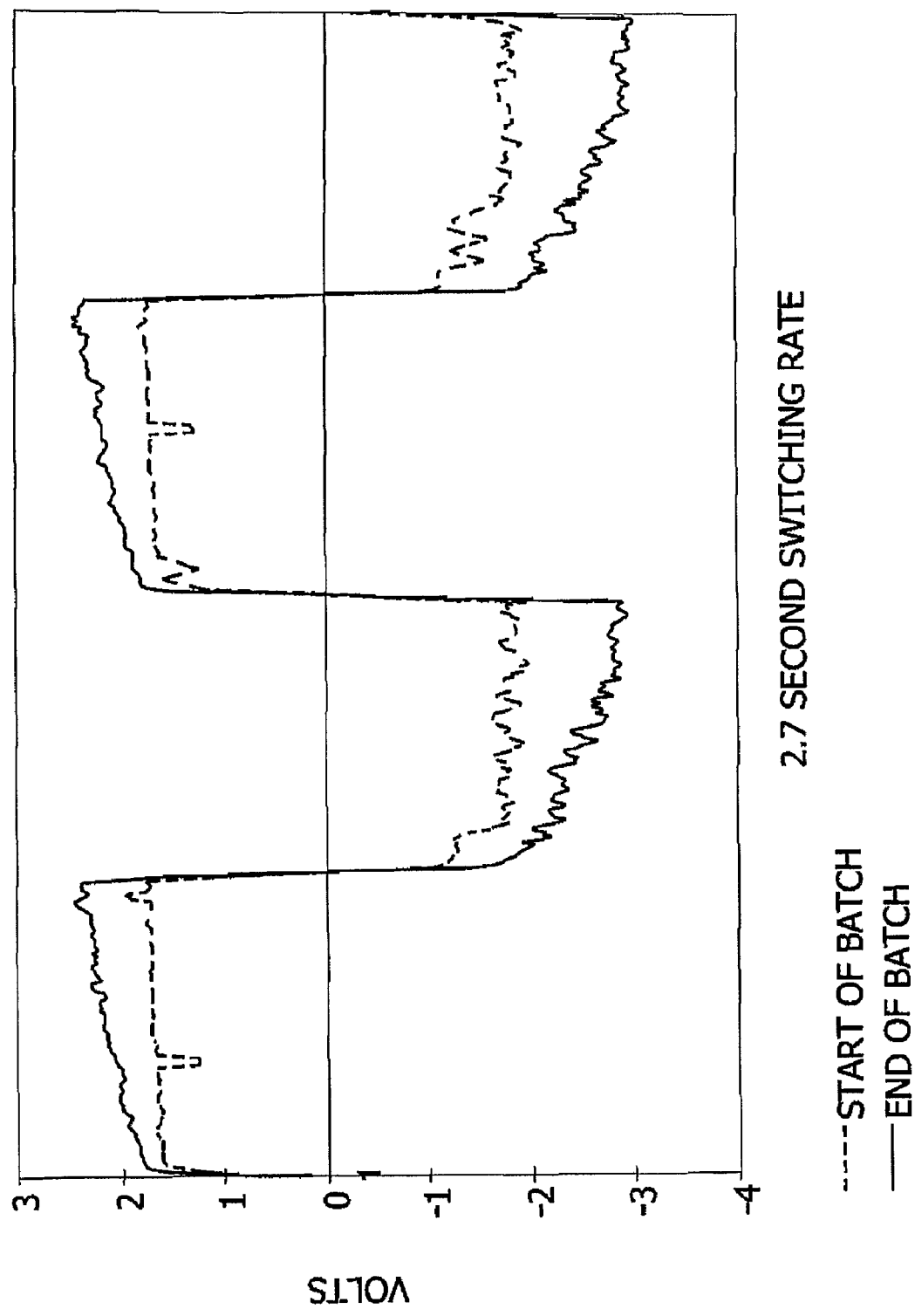
FIG. 17 is an overlay of control chart traces of voltage vs. time at constant current showing cyclic reversal of polarity and characteristic traces at both low conversion and high conversion in a batch oxidation of PMIDA to glyphosate.

To minimize effects of fouling and polarization, the polarity of the electrodes is repetitively reversed, so that what had been the working electrode becomes the counterelectrode and vice versa. Reversal is preferably effected at intervals of not more than about 10 minutes, more typically not more than about one minute, preferably not greater than about 30 seconds, most typically between about one second and about 20 seconds, preferably between about 5 seconds and about 15 seconds. A bipolar power source is provided for this purpose. FIG. 17 illustrates the typical voltage vs. time chart that is recorded using a select current electrochemical oxidation detection method with polarity reversal at 2.7 second intervals. The dashed trace is recorded early in the batch and shows that no increase in voltage is required to maintain a select current density, indicating that the current is all being carried by oxidation of $C_1$s and PMIDA, with no participation by glyphosate. The solid trace is taken later in the batch and shows that each of the alternating current pulses requires a ramp in voltage, reflecting the requirement for oxidation of glyphosate in order to carry the full select current density.

FIG. 18, which is discussed above with respect to oxygen flow and dissolved oxygen profiles, also comprises a trace of the voltage response observed in practice of a select current electrochemical oxidation end point detection method. It may be seen that the voltage declines as the aqueous reaction medium is brought to reaction temperature, goes through a trough early in the batch and then climbs along a modest slope until shortly before the end point is approached. In the last few minutes of the reaction cycle, the voltage response climbs relatively steeply (typically though not necessarily exponentially) to a level which indicates sufficient conversion for the oxygen flow to be terminated. Upon termination of oxygen supply, the dissolved oxygen content drops precipitously to essentially zero, and the voltage increases nearly instantaneously to the level at which electrochemical oxidation of PMIDA can occur in the absence of dissolved oxygen. As discussed elsewhere herein, purely electrochemical oxidation, unaided by dissolved oxygen, typically requires a potential in excess of 3 volts, more typically more than 3.5 volts.

According to an alternative method for electrochemical detection or monitoring of the conversion of PMIDA, a select voltage may be applied which is sufficient to effect electrochemical oxidation of PMIDA, but not glyphosate, and measurement made of the current response to the applied voltage. The result may be adjusted for $C_1$s, which are also oxidized at a voltage effective for the oxidation of PMIDA. The $C_1$ content at high PMIDA conversion can be estimated based on long term or short term historical analytical data, as described above with respect to the oxygen consumption and carbon dioxide generation methods, and the current equivalent thereto estimated according to Faraday's Law. After a current component equivalent to the $C_1$s is subtracted, the remaining current increment is substantially proportional to the residual PMIDA content of the aqueous reaction medium. Reduction of the residual PMIDA content to the target value is indicated by a decline in the current response as compared to that obtained at a higher PMIDA concentration.

According to a refined alternative, the select voltage method allows the $C_1$ content to be repetitively determined, and thus a zero value for the PMIDA determination to be provided, by applying two discrete voltages in sequence. The first, relatively lower voltage, is effective for the electrochemical oxidation of formaldehyde and formic acid, but not for the electrochemical oxidation of PMIDA. The second, relatively higher voltage, is sufficient for the electrochemical oxidation of PMIDA but not for the oxidation of glyphosate. The current response to the first applied voltage reflects oxidation only of the $C_1$s, while the current response to the second applied voltage reflects the oxidation of both the $C_1$s and PMIDA. The PMIDA content is indicated by the difference between the two current responses.

The various species within the oxidation reaction mixture, including formaldehyde, formic acid, PMIDA and glyphosate are all subject to entirely electrolytic oxidation in aqueous media at voltages that are relatively high. For example, it is known that glyphosate may be produced by the electrolytic oxidation of PMIDA at potentials in the range of 3.3 volts or greater. However, in the methods of the invention, PMIDA conversions are typically estimated in a reaction medium through which molecular oxygen is being constantly sparged. Thus, the medium has a dissolved oxygen content, and consequently an oxidation potential, that are substantial fractions of the values prevailing at oxygen saturation. In the presence of an adequate supply of molecular oxygen, the various electrolytic reactions proceed via the reduction of molecular oxygen at net voltages that are substantially lower than those required for electrolytic oxidation alone.

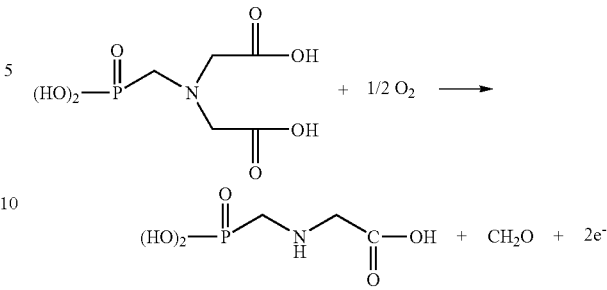

For example, oxidation of PMIDA to glypnosare proceeds typically at a voltage of about 0.7 or greater relative to a Ag/AgCl electrode. By comparison, oxidation of formaldehyde and formic acid to carbon dioxide and water proceeds at a voltage in the range of about 0.4 relative to a Ag/AgCl electrode, while oxidation of PMIDA to glyphosate requires a voltage in the range of 1.2 to 1.3.

In operation of the select voltage method, pulses are alternately and repetitively applied at a plurality of different voltages. One voltage, a relatively lower voltage, is sufficient for oxidation of $C_1$ compounds but not PMIDA. Another voltage, a relatively higher voltage, is sufficient for oxidation of both $C_1$s and PMIDA. The current or current density responses and difference between such responses are determined for each successive combination of low voltage and high voltage pulse pairs. The current difference is continually tracked. In a batch reaction, the end point is reflected by a sharp drop in the current obtained at the higher voltage, and more particularly by a sharp drop in the difference between high voltage and low voltage current as computed from pulse cycle to pulse cycle.

Figure 9:
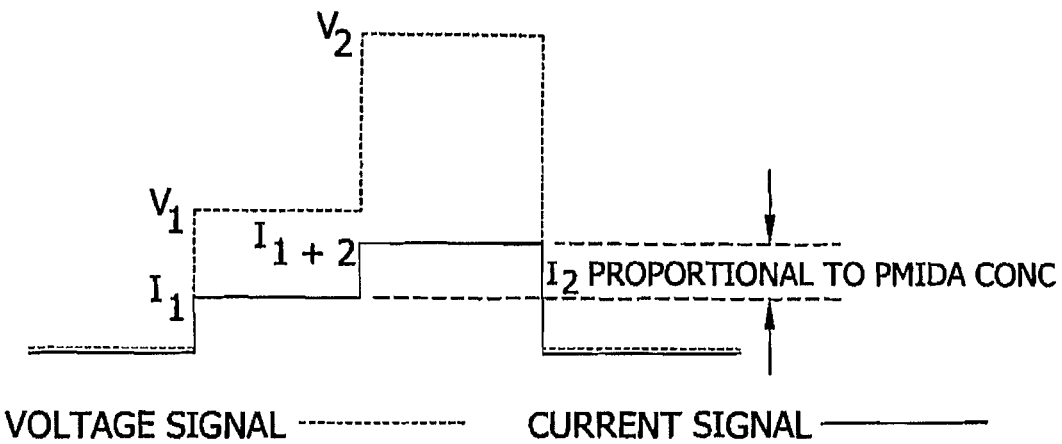
FIG. 9 is a plot of current and voltage vs. time illustrating the principles of a select voltage method for estimating the residual PMIDA content during the catalytic oxidation of PMIDA to glyphosate, and/or the end point of the catalytic oxidation reaction.

The principles and mode of operation of the select voltage method are shown in FIG. 9. At periodic intervals, a first voltage $V_1$ is applied which is sufficient for the electrochemical oxidation of by-product $C_1$ compounds, i.e., formaldehyde and formic acid, but not sufficient for the electrochemical oxidation of either PMIDA or glyphosate. The current $I_1$ generated in response to $V_1$ reflects only the concentration of the aforesaid $C_1$ compounds (and possibly other minor background contaminants) and not the concentration of either PMIDA or glyphosate. At a different point in the select voltage method cycle, a higher voltage $V_2$ is applied which is sufficient to oxidize the $C_1$ compounds (and any background contaminants) and PMIDA, but not sufficient to oxidize glyphosate. The current response to $V_2$ is $I_{1+2}$. The difference between the two observed current responses is $I_2$, the current that is attributable to the oxidation of PMIDA. As the reaction progresses, $I_1$ may continually increase, or may increase to a maximum and then remain level or decline; but a significant residual $C_1$ content typically remains in the reaction mixture even as the PMIDA end point is reached, especially in the case where the catalyst comprises carbon only. Regardless of the profile of $I_1$ across the reaction, $I_2$ declines progressively as the reaction proceeds until the target PMIDA concentration is reached.

Figure 19:
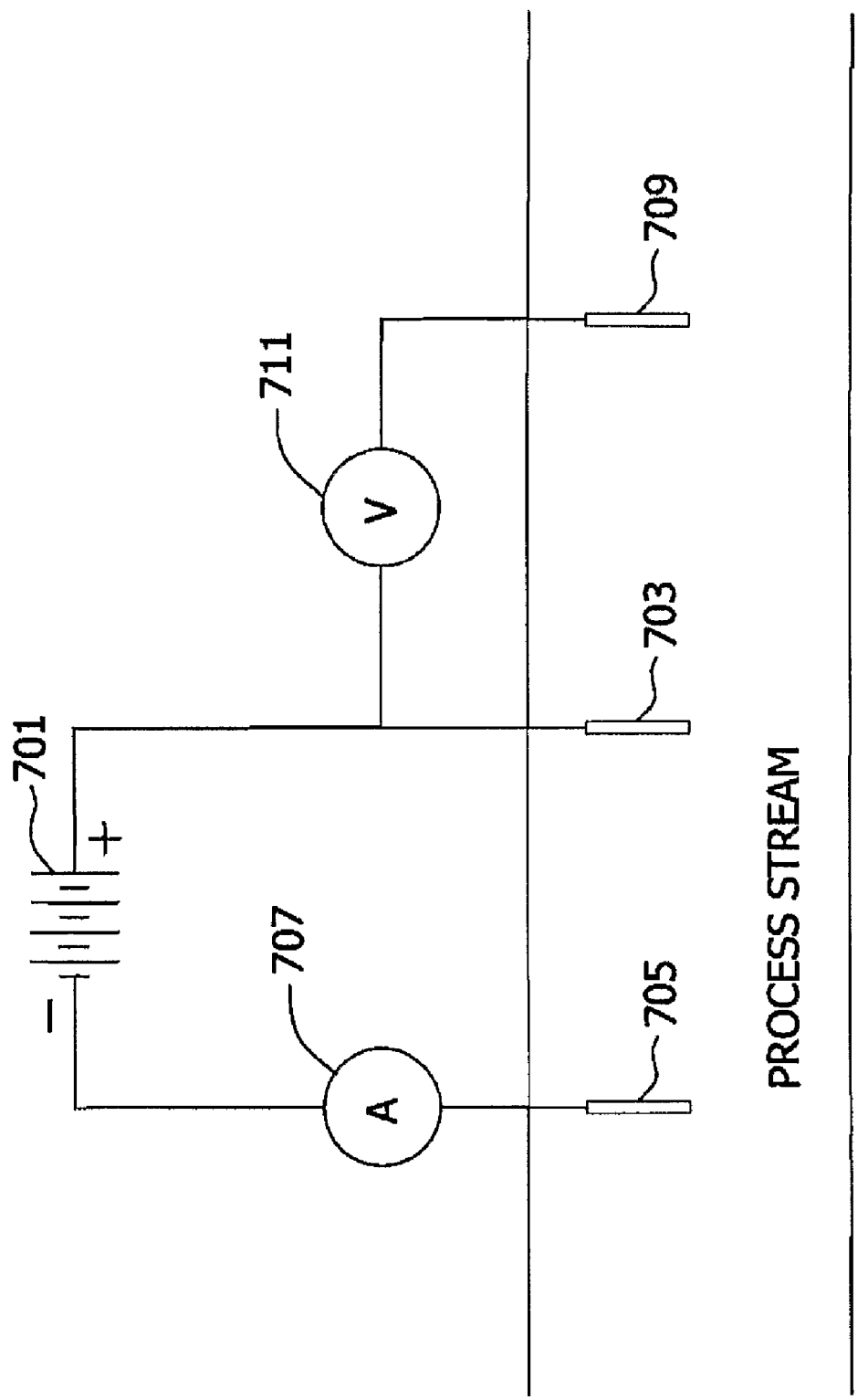
FIG. 19 schematically illustrates the stepped voltage electrochemical monitoring and detection method for PMIDA concentration and reaction end point during batch oxidation of PMIDA to glyphosate.

In implementation of both the select current and select voltage methods, the electrodes may be constructed of any convenient material that has a low oxidation potential and is chemically inert in the system. As a practical matter, these considerations tend to narrow the options. Platinum is preferred for its chemical and electrochemical inertness. A Pt/Ir electrode combines inertness with mechanical strength. In various preferred embodiments of the select voltage method, as illustrated in FIG. 19, a reference electrode, e.g., a pseudo Ag/AgCl electrode is provided in proximity to the working electrode (anode) at which the oxidation reaction takes place. Because no current flows at the reference electrode, it functions reliably to sense the voltage prevailing at the working electrode so as to assist in controlling the latter at a target voltage such as $V_1$, for oxidation only of $C_1$ compounds to generate current $I_1$, or $V_2$, for oxidation of both $C_1$ compounds and PMIDA without oxidation of glyphosate to generate current $I_{1+2}$. By sensing the voltage at the working electrode, the reference electrode provides the basis for controlling that voltage value at a desired level. In the absence of the reference electrode, control of the working electrode at a proper voltage for the desired electrochemical oxidation reaction may be compromised by the resistivity of the solution and other vagaries of the environment in which the electrolytic circuit must function.

Alternatively, the reference electrode may be used merely to sense the voltage at the working electrode, without being part of any control circuit for maintaining that voltage at a target level. Instead, as further discussed hereinbelow, the voltage as sensed may be used as a term in a regression equation for computing PMIDA content from this and other measured parameters of the reaction system. FIG. 19 illustrates such a system in which a voltage is applied from a power source 701 across a working electrode 703 and a counterelectrode (auxiliary electrode) 705 that are immersed in the process stream, and the resulting current measured by means of an ammeter 707. Via a potentiometer 711, the voltage across reference electrode 709 and working electrode 703 is sensed.

In some instances, it may be desirable for the reference electrode to be based on a redox couple of known oxidation potential, e.g., Ag/AgCl.

However, in some applications, especially where the aqueous medium flowing past the electrode contains a particulate catalyst, a Ag electrode may rapidly erode or corrode. In such applications, it may be preferable for the reference electrode to also be formed of Pt or a Pt/Ir alloy. In the latter instance, the reference electrode may not have a known potential, but since no current flows at this electrode it facilitates the means by which the working electrode voltage may be sensed and controlled.

Even where a reference electrode is used to assist in measurement of the working electrode voltage at a value effective for the desired electrochemical reactions, variables other than the power consumption response to the select current or select voltage have been found to affect the precision of the electrochemical methods for PMIDA conversion. These include for example, the absolute voltages (as contrasted with the voltage difference), the rest potential between pulses, i.e., the oxidation potential of the medium, and the temperature. Rest potential may be determined with an ORP electrode, as discussed hereinabove. In the select voltage method, the effect of such other variables may be taken into account using an algorithm that may be developed for the purpose. Advantageously, compensation for these various effects may be accounted for on-line by transmitting signals for current, current difference, temperature, absolute voltage and rest potential to a processor which is programmed with the algorithm.

Although the electrochemical methods for estimating PMIDA concentration operate on known principles, it has been found that the vagaries of an operating environment are not always susceptible to evaluation by purely scientific calculation, especially at relatively low PMIDA concentration. Instead it has been found that estimation of the PMIDA content may be best achieved by development and application of an empirical algorithm that is generated by regression analysis of extensive operating data. Thus, a typical empirical relationship is as set forth below:

$$PMIDA(\text{ppm}) = C_1(P1OV) + C_2(P1OC) + C_3(P2OV) + C_4(P2OC) + C_5(RV) + C_6(PT) + C_7 \quad \text{(Eq. 1-1)}$$

Where:
P1OV=pulse 1 observed voltage
P1OC=pulse 1 observed current
P2OV=pulse 2 observed voltage
P2OC=pulse 2 observed current
RV=rest voltage
PT=process temperature
$C_1, C_2, C_3, C_4, C_5$=regression equation coefficients
$C_7$=a constant The values of the coefficients may vary significantly between batch vs. continuous mode oxidation, filtered vs. unfiltered aqueous medium, type and age of catalyst, and numerous other variables of the process, equipment and control system in the manufacturing facility in which the method is used. Moreover, because the coefficients are empirical as determined by regression analysis, they are typically sensitive to modest variations in system parameters, and can shift by orders of magnitude. In such instances, an order of magnitude change in one coefficient may be offset by an order of magnitude change in other coefficients of opposite sign. Typically, it may also be necessary to apply an offset or correction factor to the value as calculated by an equation of the nature set forth above. It will be understood that during any particular period of operation, the range of the aforesaid coefficients and correction factor may vary significantly. In this regard, an empirical regression equation for residual PMIDA content is generally valid over a PMIDA range of no more than about two orders of magnitude. For example, separate algorithms may be necessary for computation in a range of 200 to 2000 ppm vs. a range of 2000 to 8000 ppm. It has been found that a logarithmic model may reconcile data from these separate ranges, but more accurate operating information is provided by applying separate linear equations to separate ranges of PMIDA content.

Electrodes for electrochemical estimation of conversion are preferably positioned in a location where temperature is substantially constant and either equal to or consistently reflective of the bulk temperature in the catalytic oxidation reaction zone. It may also be advantageous to position the electrodes in an area of relatively high flow in order to minimize fouling and polarization of the electrodes. In the select current method, it is also preferable to maintain the flow rate and other measurement variables as nearly constant as is practicable, including oxygen potential of the solution, solution conductivity, and electrode disposition and dimensions. Where the reaction zone comprises a stirred tank reactor having an external heat exchanger for removing the exothermic heat of reaction, the electrodes are advantageously positioned in the circulating line immediately upstream of the heat exchanger; or in a slip stream parallel to the main circulating stream, but also preferably just upstream of the heat exchanger. This position affords both constant temperature (bulk temperature of the aqueous medium) and flow.

In certain applications, it may be desirable to periodically reverse the polarity of a select voltage electrochemical oxidation circuit. For example, in a continuous process comprising CSTRs in series, remaining PMIDA content may advantageously be estimated for a stream exiting a CSTR other than the final reactor in the series, e.g., either the penultimate reactor or the third last reactor. In such instance, the residual PMIDA content may be high enough to cause polarization by accumulation of a high concentration of glyphosate in a boundary layer along the surface of the electrode and/or fouling of the electrode by deposit of solid glyphosate. The solubility of glyphosate in the aqueous medium is limited. If glyphosate accumulates to a high enough concentration in the boundary layer, it can precipitate on the electrode surface. This may be manifested by drift in the response at different voltages and residual current when the circuit is otherwise at rest. Periodic reversal of polarity helps to prevent concentration polarization and fouling. The frequency of reversal depends on the environment in which the select voltage system is applied. Typically, reversal may be effected every 15 seconds to several minutes, more typically between about 15 seconds and about two minutes, still more typically between about 20 seconds and about one minute.

The select voltage method is somewhat more adaptable to changing conditions, in part because a zero basis is established by measuring both the current attributable to oxidation of $C_1$s only and the current attributable to oxidation of both $C_1$s and PMIDA, and further because of the availability of an algorithm that compensates for changes in temperature, absolute voltage and rest potential.

Figure 10:
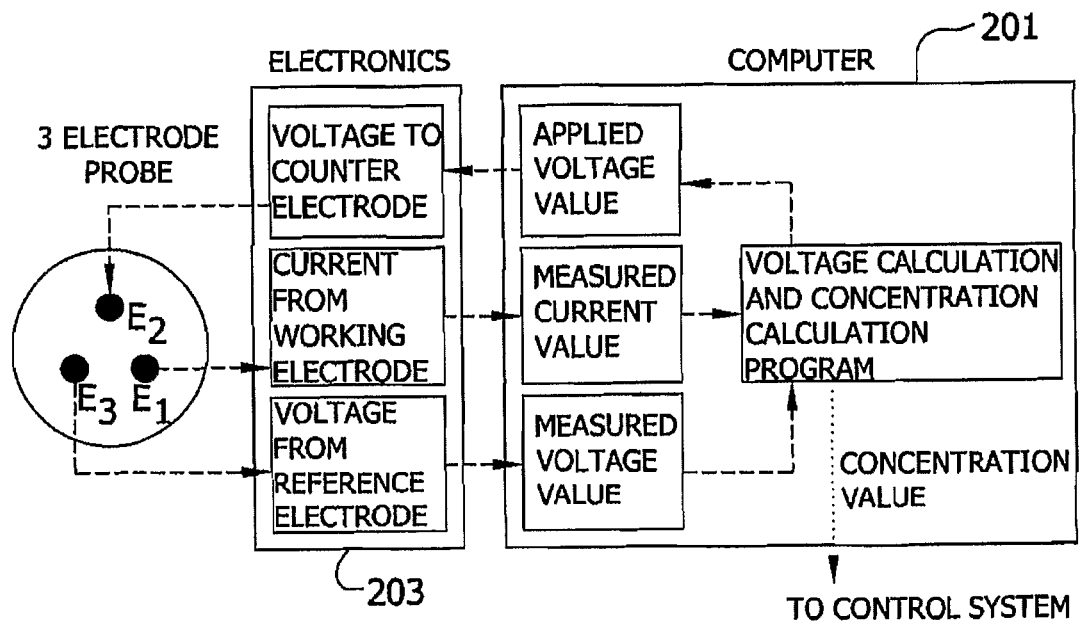
FIG. 10 is a diagram functionally illustrating the operation of a control system for implementing a select voltage method for detecting the residual PMIDA content during the catalytic oxidation of PMIDA to glyphosate, and/or the end point of the catalytic oxidation reaction.

FIG. 10 schematically illustrates a control system for implementing the select voltage method for tracking the conversion of PMIDA. A computer controller 201 is programmed to impose a select voltage between working electrode $E_1$ and counterelectrode $E_2$. In response to a voltage signal from across reference electrode $E_3$ and working electrode $E_1$, an output signal from the computer adjusts impedance in the electronic circuitry 203 to maintain the voltage at the desired value $V_1$ or $V_2$ as the case may be, depending on which cycle the computer is running. The resulting current ($I_1$ or $I_{1+2}$) is sensed by a current sensor in the circuitry 203 and a current signal transmitted to the computer 201. Voltage $V_1$, which is sufficient only for $C_1$ compound oxidation, is applied alternately to a voltage $V_2$, which sufficient for oxidation of both $C_1$ compounds and PMIDA. Typically, each voltage is applied for a period of between about 10 and about 20 seconds, with a rest interval between applications of typically between about 10 and 20 seconds. The resulting current $I_1$ or $I_{1+2}$ is sensed across the working electrode $E_1$ and the counterelectrode electrode $E_2$ and transmitted to the computer processor 201. The computer is programmed with an algorithm by which the current $I_2$ can be computed from measured currents $I_1$ and $I_{1+2}$, and from which the computer determines the residual concentration of PMIDA, effectively from the difference between $I_1$ and $I_{1+2}$, i.e., $I_2$, but preferably from measurements that include applied voltages and rest potentials, for example per regression equation 1-1. An output signal is transmitted to a readout device that may be positioned on a control panel and/or on or in the vicinity of the reactor. As further discussed hereinbelow, the output signal from computer 201 may be used in feedback control of an independent process variable such as, e.g., the reaction temperature, intensity of agitation, the rate and/or pressure of oxygen supply or, in a continuous reaction system, the rate of introduction of PMIDA feed solution to the reactor and the rate of withdrawal of product reaction mixture therefrom.

Select current and select voltage electrochemical oxidation methods can also be used in combination to estimate conversion and/or determine end point of the oxidation reaction. One alternative which can be used for this purpose, and interpreted with respect to either voltage as function of current or current as a function of voltage, is the current scanning method that is described hereinabove. Whether current response to voltage and voltage response to current are gathered dynamically by scanning, or by separately applied select current and select discrete voltage(s), an algorithm may be derived by regression analysis using current response to applied voltage and voltage response to applied current density. The product of each of these responses and an appropriate coefficient is incorporated as a term in a polynomial expression for residual PMIDA content of the reaction medium. Generally, voltage response to select current appears as a negative term in an expression for residual PMIDA, while current response to select voltage is a positive term. The precision of the determination can be enhanced by including the rest potential, which essentially corresponds to the oxidation potential of the aqueous medium, and can be measured using an oxidation/reduction potential probe. Generally, the oxidation potential appears as a negative term in the regression equation. The coefficients are specific to the conditions of the particular reaction, the nature, loading, age and activity of the catalyst, and at least potentially to the peculiarities of the particular reactor configuration. However, based on the description herein, they can be readily derived by those skilled in the art from standard regression analysis.

Figure 11:
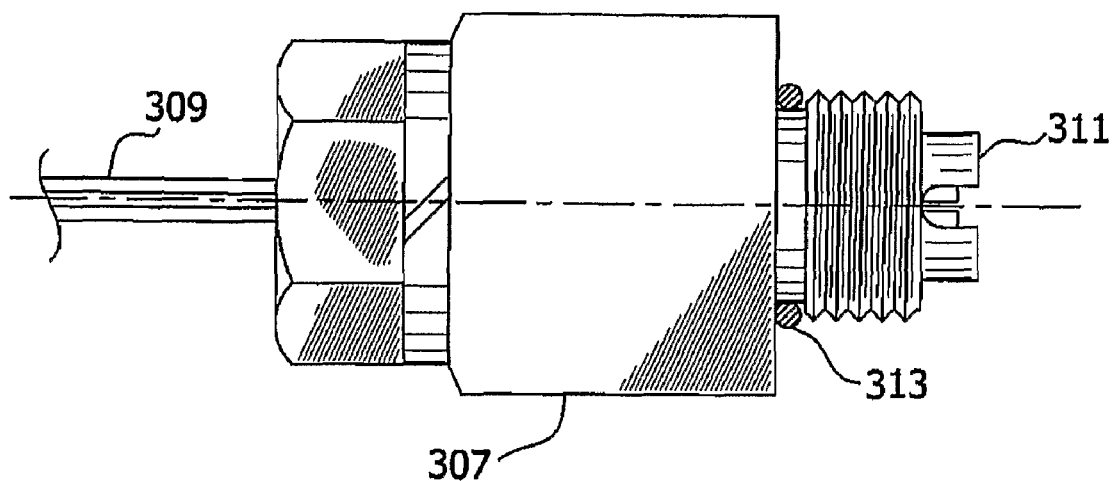
FIG. 11 is side elevation drawing of a probe that may be used to carry electrodes that are mounted in a process stream for measurement of electrochemical oxidation potential.
Figure 12:
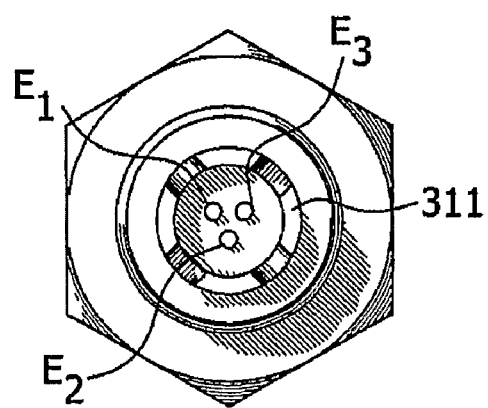
FIG. 12 is front elevation of the probe of FIG. 11.
Figure 13:
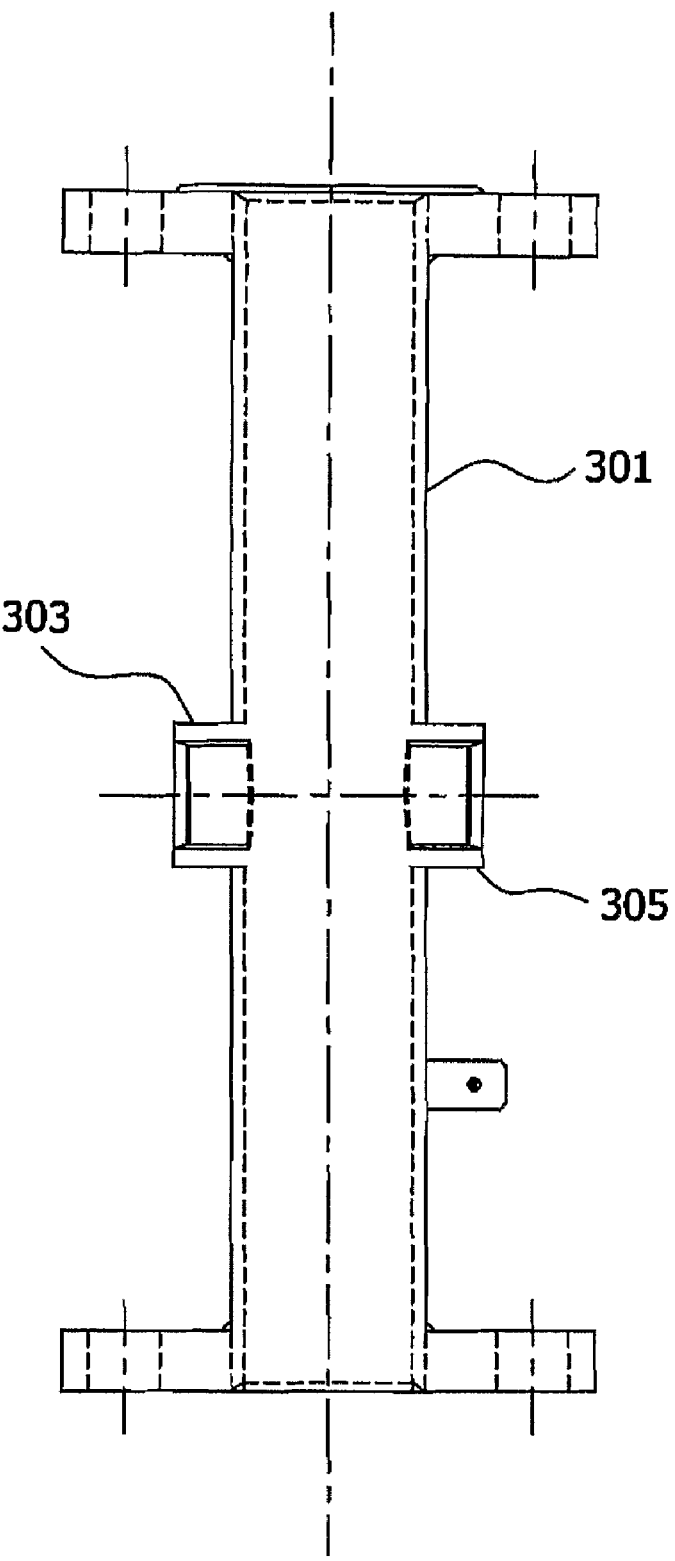
FIG. 13 is a drawing in section of a pipe spool within which the probe of FIGS. 11 and 12 may be inserted.
Figure 16:
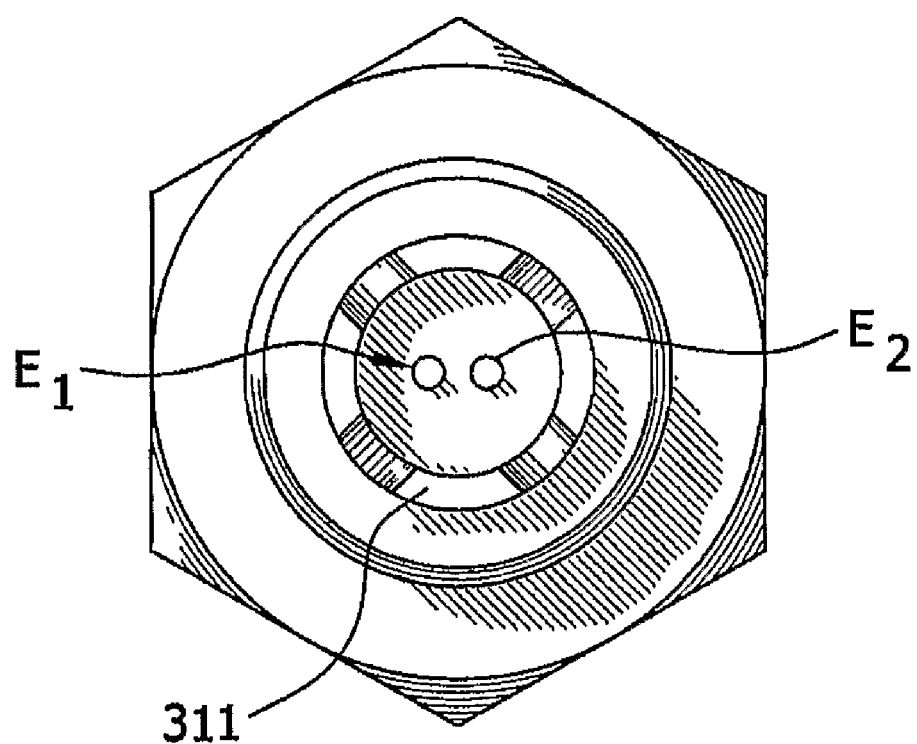
FIG. 16 is an end view of an electrode probe that is similar to FIG. 12 but showing only two electrodes (i.e., a working electrode and a counterelectrode) as used in an electrochemical oxidation method for determining residual PMIDA or $C_1$ by-products.

In practice of the select voltage method, or in sweeping the voltage, data may be gathered by which the requisite batch reaction time or continuous reactor residence time necessary to obtain a target conversion and/or residual PMIDA content may be projected in the manner described above in the case of FTIR. For example, a series of current responses may be obtained in response to a select applied voltage, or a plurality of discrete select voltages. Based on a known or determined order of reaction, these responses may be used to project the batch reaction time or continuous reaction residence time necessary to achieve a target conversion of PMIDA to glyphosate or another intermediate for glyphosate and/or a target end point defined by residual PMIDA concentration. The projection may be made based on a known or determined relationship between residual PMIDA content and the current response at a plurality of the series of applied voltages. At least two or more of the applied current determinations are preferably obtained under non-zero order reaction conditions. As in the case of projections based on FTIR, oxygen consumption, or $CO_2$ generation, the order of the reaction and the rate constant may be determined from historical HPLC data, FTIR data, other analytical data, or operational data obtained from laboratory and/or industrial oxidation reactions. Where the projection is made on the basis of substantially first order reaction, the end point may be projected based on a straight line plot of the logarithm of the remaining PMIDA concentration vs. time.

Where the electrodes used in either the select current or select voltage electrochemical oxidation method are inserted in a recirculation line, e.g., a slip stream of the reaction mixture circulating through an external heat exchanger, the electrodes may conveniently be mounted on a probe that is inserted in a pipe spool such as that illustrated in FIG. 13. A flanged pipe pool 301 is provided with an internally threaded lateral entry coupling 303 that is adapted for insertion of the probe. As illustrated in the drawing, the spool includes a second internally threaded coupling 305 so that two probes can be accommodated by the same spool. The probe as illustrated in FIGS. 11 and 12 includes a bushing 307 that is threadably received in coupling 303 or 305, and a cable 309 which carries leads for the electrodes. The probe is sealed against leakage of process liquid by an O-ring 313. The cable passes through and is sealed within the bushing. As shown in FIG. 12, the probe comprises three electrodes, i.e., working electrode $E_1$, counterelectrode $E_2$, and reference electrode $E_3$. FIG. 16 is an end view of a two electrode probe. Thus, the electrode probe may be adapted for use in either the select current or stepped voltage method as described above. Typically, coupling 305, bushing 307 and electrodes $E_1$, $E_2$, and $E_3$ are positioned normal to the direction of flow of aqueous reaction medium through spool 301. An annular shroud 311, generally coaxial with bushing 307 and coupling 305, serves to provide at least some reasonable degree of protection for the electrodes against erosion that otherwise may result from action of the flowing reaction mixture, and especially catalyst that is ordinarily suspended therein. The shroud may be slotted at positions around its circumference to allow adequate circulation of bulk liquid to the electrode surfaces. The shroud and other wetted surfaces of probe are preferably constructed of a corrosion resistant alloy such as, for example, alloy 825 of alloy 276.

In providing for two separate probes, the arrangement of FIG. 13 allows for operation using a variety of different electrode combinations; and in particular for redundant measurement against the contingency that one electrode probe may become fouled or polarized and give a false reading. Thus, for example, using the arrangement provided in FIG. 13 the electrochemical detection methods may use an electrochemical circuit comprising a single dual electrode probe of the type illustrated in FIGS. 11 and 12, or two single isolated electrodes; and may provide for redundant measurement, or two dual isolated electrodes.

For proper calibration and operation of the select current and select voltage electrochemical oxidation methods, it is desirable to establish whether: (i) the aqueous medium subject to the method has an oxidation potential sufficient for the various reactions to proceed in the voltage ranges described above; or instead (ii) the oxidation potential is so low that detection can proceed only at the relatively high potentials that are necessary for solely electrolytic oxidation. Ordinarily, it may also be desirable to maintain the oxidation potential of the analyte medium in one condition or the other, i.e., at an oxidation potential sufficient for PMIDA to be electrochemically oxidized in the range of 0.7 to 1.0 volt, or at oxidation potential insufficient for oxidation of PMIDA to proceed until a significantly higher threshold voltages is imposed.

Measurement of oxidation voltages and currents may further be complicated by the presence of catalyst in the aqueous reaction medium that is subjected to the end point detection method. It has been observed that the presence of catalyst tends to promote higher currents at a given voltage and vice versa. Because the catalyst has a significant oxygen carrying capacity, it is believed that the effect of catalyst may be to transport oxygen to the electrodes, either by collisions between catalyst and the electrodes or by oxygen enrichment of the solution in proximity to the electrodes. With reference to FIGS. 1 and 2, for example, the voltage and current responses to an electrode probe placed in one or more of reactors 101, 103 and 105, or in a circulating line for an external heat exchanger associated with such reactor(s), may differ significantly from the response obtained by application of current or voltage to a sample of the aqueous medium from which the catalyst has been removed, as by filtration. Similarly, the responses obtained from a probe in a reactor or reactor circulating line may differ significantly from the response that is observed upon application or current or voltage to the aqueous reaction medium downstream of filter 107. The select voltage method may be calibrated by periodic assays of the reaction mixture and comparison of current at discrete select voltages with assay for PMIDA, formaldehyde and formic acid.

Figure 14:
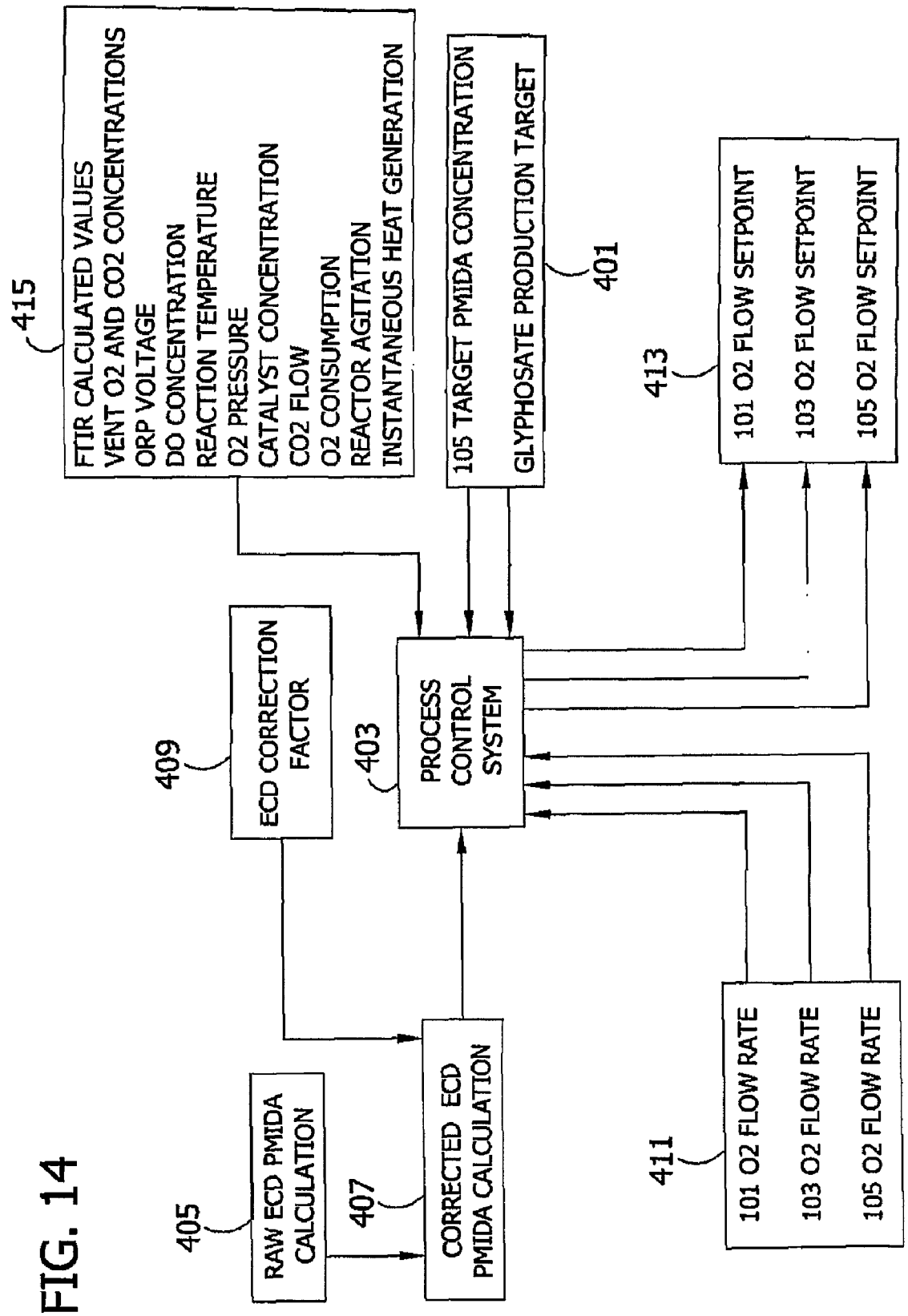
FIG. 14 is a block diagram illustrating a scheme for controlling PMIDA conversion in a reaction system of the type illustrated in FIGS. 1 and 2.

FIG. 14 illustrates a scheme for control of the PMIDA conversion in a reaction system of the type illustrated in FIGS. 1 and 2, and more particularly for controlling the conditions of the reaction to achieve and maintain a target PMIDA concentration in the reaction medium exiting the reaction system. In the process control scheme of FIG. 14, conversion of PMIDA is established and maintained by an appropriate combination of reactor residence time, PMIDA concentration, reaction temperature, intensity of agitation and oxygen flow rate. A conventional process control instrumentation system, indicated collectively and schematically at 403, is provided for measurement and control of PMIDA feed rate, temperature in the reactors, and calculation of oxygen flow setpoints to each of reactors 101, 103 and 105. Signals from sensors and controllers including but not limited to those listed in block 415, are transmitted to 403 for adjusting the control set points of oxygen into the several reactors 413.

A select voltage or select current system 405 provides a raw estimate of residual PMIDA content based on the response obtained in an appropriate reaction stream or sample. For example, an electrochemical detection probe may be positioned in reactor 105, in a line circulating aqueous reaction medium between reactor 105 and an external heat exchanger associated therewith, or in the line exiting filter 107. Optionally, measurements may be taken in both reactor 105, or its circulating line, and in the exit stream from filter 107. The measurement in reactor 105 or its circulating line provides a value that may be used for control with somewhat less response lag than is incurred where the control function responds to the PMIDA value obtained in the stream exiting filter 107. Otherwise, placing a probe in the filtrate is generally advantageous because it measures PMIDA content in the substantial absence of catalyst, and is, therefore, less subject to vagaries of catalyst activity, concentration, etc. However, the stream exiting the filter may in some instances have a relatively low dissolved oxygen content. Care must be taken to determine whether the oxidation potential of the filtrate is sufficient for electrochemical oxidation in the preferred ranges discussed above. Optionally, the filtrate may be aerated to make certain that its oxidation potential is sufficient for oxidation of PMIDA at a voltage in the range of about 0.7 to about 1.0. Alternatively, the filtrate may be purposefully subjected to electrochemical oxidation under oxygen starved conditions, in which case $C_1$ oxidation may typically be observed in the range between about 1.5 and about 2 volts, and PMIDA oxidation may be observed in the range between about 3.5 and about 5 volts.

A raw estimate of PMIDA concentration is computed by function block 405 according to an algorithm such as equation 1-1 above. A correction factor for the raw PMIDA estimate is computed in function block 409 according to an empirical correction algorithm which compares previous raw PMIDA estimated from 405 with measured laboratory values at known PMIDA concentration. A function block 407 applies the correction factor to a raw PMIDA computation to obtain a corrected PMIDA concentration. Signals reflecting the corrected PMIDA concentration are transmitted as an input to process control system 403, which is programmed with an algorithm for computing adjusted set points of the oxygen flow 413 based on inputs from $O_2$ flowrates 411 at levels calculated to afford the desired conversion and residual PMIDA content in the aqueous product reaction mixture exiting reactor 105 and/or filter 107 as specified by manual inputs from 401.

In some instances, it may be useful to not only compensate for the oxidation of $C_1$s in estimating residual PMIDA content by electrochemical oxidation, but also to obtain a separate estimate of the residual concentration(s) of the $C_1$ compounds themselves. The principles as applied above may be applied to obtain such indication. In the select voltage method, for example, a separate algorithm may be developed by regression analysis comparing $I_1$ with analytical data for formaldehyde and formic acid, and with other parameters of the process such as temperature, rest potential, etc.

As described in further detail above with respect to FTIR, and below with respect to heat generation, in a batch mode the rate constant and the order of the reaction may be estimated from the rate of decline in the reaction rate as a function of time as determined from a plurality of analyses and/or current responses and/or other operational data obtained during the course of the reaction in which the end point is projected, or from a preceding batch. More particularly, the rate constant may be estimated from operational data based on the rate of exothermic heat generation, the rate of oxygen consumption in the reaction zone, the rate of generation of $CO_2$ in the reaction zone, or combinations thereof.

Similar determinations can be made from data obtained at different residence times in a continuous reaction system. For example, where the reaction is conducted in a continuous back mixed reaction zone under non-zero order conditions, a projection may be made based on the PMIDA content of the reaction medium exiting the penultimate reactor. The order of the reaction and the kinetic rate constant can be estimated based on historical operational or analytical data obtained from laboratory and/or industrial oxidation reactions, including recently preceding operations in the continuous back mixed reaction zone. For example, the kinetic rate constant may be estimated from the PMIDA content of the feed solution entering the back mixed reaction zone, and the PMIDA content of the solution withdrawn from the back mixed reaction zone as a function of the residence time therein.

According to a still further alternative, the PMIDA conversion and/or end point may be estimated from cumulative heat generation in the reaction zone during the course of the reaction. Because the oxidation reaction is exothermic, means are provided for transfer of reaction heat from the reaction mixture under feedback temperature control. Thus, if a cooling fluid such as a source of cooling water is passed through a heat exchanger, e.g., cooling coils, a cooling jacket or an external heat exchanger, for controlling the reaction temperature, the extent of reaction can be estimated from the cumulative heat dissipation over the batch cycle, as may be determined from an integrated average of the product of cooling fluid flow rate and temperature rise through the heat exchanger during the course of the batch. Thus, the method comprises continually or repetitively measuring heat generation during the course of the reaction, preferably by continually or repetitively measuring both the flow rate of the coolant and the temperature rise through the heat exchanger, and computing the cumulative heat generation within a batch reaction zone at any point in a batch reaction cycle, or in a continuous reaction zone comprising a particular reactor or the total of all reactors in a series of CSTRs. To estimate the conversion, the heat generated in the reaction zone is compared with the mass of PMIDA charged to the reaction zone and the exothermic heat of reaction for the oxidation of PMIDA to glyphosate. In a continuous reaction system, such comparison can be made over a select time period, or repetitively over similar select time periods. Based on historical analytical data, the value thus obtained can be adjusted for heat generated in the oxidation of formaldehyde to formic acid, and formic acid to $CO_2$. Alternatively, an estimate of residual $C_1$ content may be based, for example, on FTIR or electrochemical oxidation data. Using residual $C_1$s concentrations as determined by electrochemical oxidation, a material balance may be computed to determine the quantities of formaldehyde and formic acid consumed by oxidation vs. vent loss. A $C_1$ heat balance based on the material balance provides a $C_1$ oxidation heat component by which the gross heat generation observed can be adjusted to determine the quantity of heat associated with oxidation of PMIDA. For this purpose, the PMIDA charge may be either the initial charge to a batch reaction zone or the quantity charged to a continuous reaction zone over the period during which the cumulative heat generation is measured. In estimating conversion from the cumulative heat generation, the precision of the estimate is enhanced by a careful and accurate measurement of the PMIDA charge to a batch reactor, or of the integrated average instantaneous rate at which PMIDA is charged to a continuous reaction system.

Figure 15:
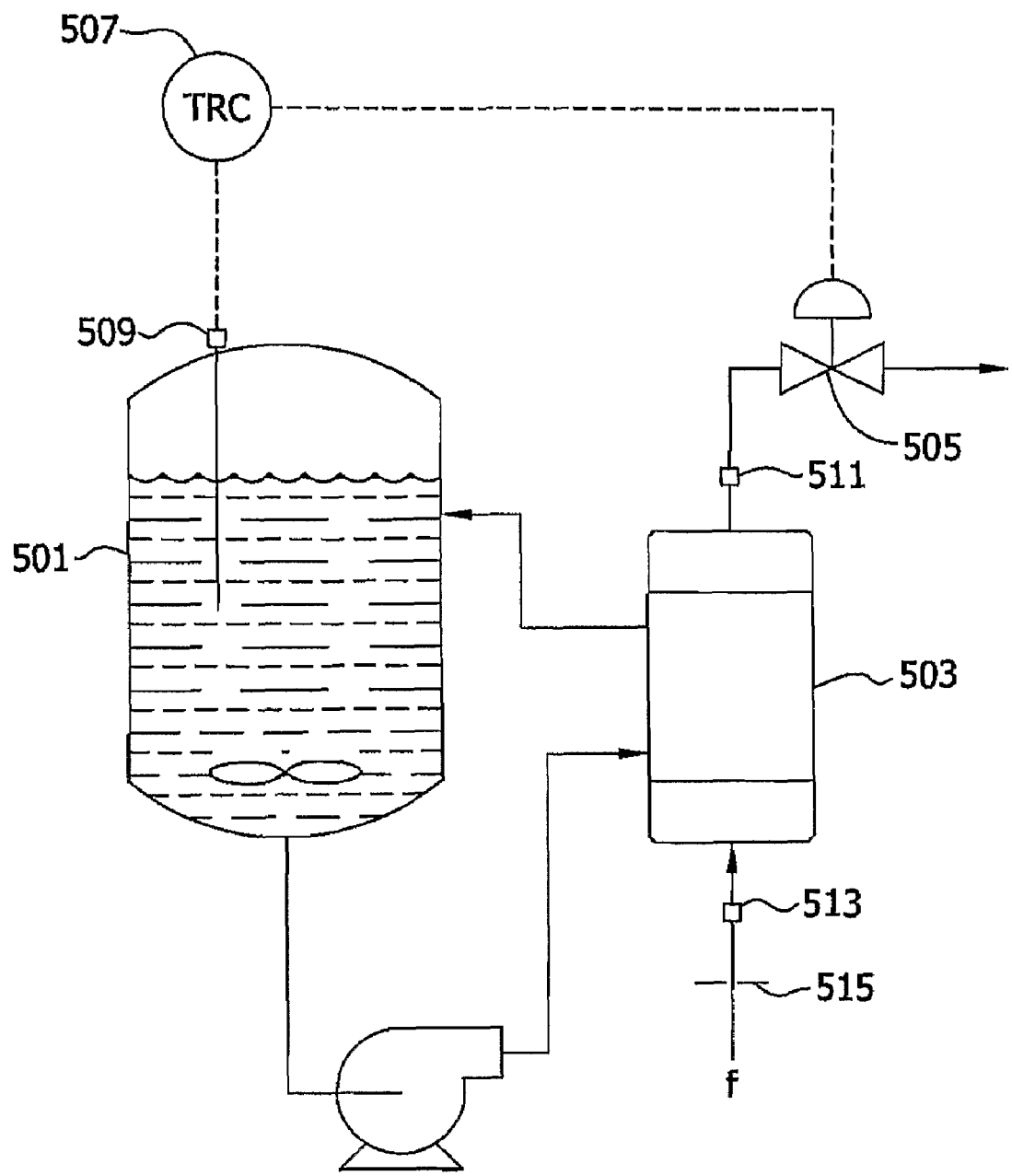
FIG. 15 is a flow sheet and instrumentation diagram for a batch oxidation reactor illustrating the controls and measurements by which cumulative heat generation embodiments of the invention may be implemented.

Practice of the cumulative heat balance method for estimation of PMIDA conversion is illustrated in FIG. 15. As schematically illustrated, the reaction system comprises a single batch oxidation reactor 501 and a single external heat exchanger 503 through which the reaction mixture is circulated during the course of reaction. A cooling fluid is passed through exchanger 503 at a rate which is regulated by a control valve 505 and by a temperature controller 507 in response to a reaction mixture temperature sensor 509 to maintain a constant temperature of the reaction mixture. Temperature sensors 511 and 513 continually measure the temperature of the cooling fluid entering ($T_{c,0}$) and exiting ($T_{c,f}$) heat exchanger 503. By means of an orifice or magnetic flowmeter 515, the flow rate (F) of coolant through the heat exchanger is also continually measured. Subject to adjustment for heat generated in the oxidation of formaldehyde to formic acid and formic acid to carbon dioxide, estimation of PMIDA conversion from cumulative or differential heat generation may be illustrated as follows:

In determining exothermic heat generated during a batch or continuous oxidation reaction, the following terms may be defined for use in quantifying heat rejected to the external heat exchanger 503 as shown in FIG. 15, assuming a well mixed reactor and approximately steady state across the heat exchanger:

$\dot{Q}$=Heat removal rate via heat exchanger, ~steady state across heat exchanger J/sec F(t)=cooling water flow, varies with time [=] kg/sec $T_{c,0}$=inlet cooling water temperature [=] ° C.

$T_{c,f}$(t)=outlet cooling water temperature, varies with time [=] ° C.

$C_c$=heat capacity of cooling water $$[=]\frac{J}{kg\,°\,C.}$$

Assuming steady state across heat exchanger:

$$\dot{Q}=F(t)C_C(T_{c,f}(t)-T_{c,0}) \qquad (5\text{-}1)$$

R=reaction rate [=] kg/sec

T(t)=reactor temperature [=] ° C.

M=total reaction mass [=] kg, assumed to remain substantially constant $M_0$=initial mass PMIDA [=] kg $M_f$=final (i.e., residual) PMIDA [=] kg $C_p$=heat capacity of raw mass [=] J/kg° C.

$T_R$=reference temperature [=] ° C.

$\Delta H_R$=heat of reaction [=] J/kg, negative for exothermic reactions $$\frac{d(C_p M(T - T_R))}{dt} = -(R \Delta H_R) - \dot{Q} \qquad (5\text{-}2)$$

$Q_E$=cumulative heat removed from system [=] J $$Q_E = \int \dot{Q} dt \qquad (5\text{-}3)$$

Integrate equation 5-2 from some initial time in a batch (e.g., at t=0, when the reactor temperature is $T_0$) through some final time (e.g., t=f, when the reactor temperature is $T_f$):

$$C_p M(T_f - T_0) = -\Delta H_R(M_o - M_f) - Q_E \qquad (5\text{-}4)$$

or $$Q_E = -\Delta H_R(M_o - M_f) - C_p M(T_f - T_0) \qquad (5\text{-}5)$$

$$M_f = M_o + \frac{\int F(t) C_c (T_{c,f} - T_{c,o}) dt + C_p M(T_f - T_0)}{\Delta H_R} \qquad (5\text{-}6)$$

Further as described above with respect to cumulative oxygen consumption and carbon dioxide generation, the accuracy with which cumulative exothermic heat generation is used to estimate conversion and/or residual PMIDA content can be enhanced by combining measurement of heat generation with other methods for determining conversion. For example, a base point PMIDA content can be determined analytically from a sample taken at a relatively high conversion, and heat generation measured from the time (or location within a continuous oxidation reactor system) at which the base point sample is taken. As in the case of determining conversion and/or end point from oxygen consumption or $CO_2$ generation, error in measurement of cumulative heat release, or arising from heat generation other than from oxidation of PMIDA, or PMIDA and $C_1$ by-products, is a fraction only of the incremental heat generation during the final stage of conversion after the base point rather than a fraction of the total exothermic heat generated in the conversion of all PMIDA charged to the reactor.

This combined method enjoys the same advantages as the combined analytical and oxygen consumption method, or combined analytical and $CO_2$ generation method, as described above. Thus, it is governed by chemical analysis up to the high conversion base point during which such analysis is the most reliable, then switches at the base point to cumulative heat generation over the final stage of the reaction, during which the latter method typically provides accuracy superior to that of chemical analysis.

In this combined method, compensation for formation and consumption of formaldehyde and formic acid can be accomplished in the same manner as generally described above with respect to the oxygen consumption method, and elaborated below with respect to the heat generation method.

Application of cumulative heat generation after the base point may be illustrated mathematically as follows:

where:

$CO_{2gen}$=cumulative $CO_2$ generation from $t_o$ through t

Gly=N-(phosphonomethyl)glycine

FM=formaldehyde ($CH_2O$) at time t subsequent to the base point

FA=formic acid at time t subsequent to the base point $FM_0$=formaldehyde at the base point as measured analytically $FA_0$=formic acid at base point as measured analytically $t_0$=time at the base point analysis (e.g., by FTIR)

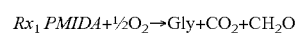

$Rx_1$ PMIDA+½$O_2$→Gly+$CO_2$+$CH_2O$

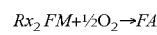

$Rx_2$ FM+½$O_2$→FA

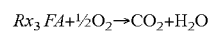

$Rx_3$ FA+½$O_2$→$CO_2$+$H_2O$

For this reaction system (total molar basis):

$$\overline{CO}_{2gen} = 2(PMIDA_o - PMIDA) - (FM + FA) + (FM_o + FA_o)$$

$$PMIDA = -\left(\frac{\overline{CO}_{2gen} + FM + FA - FM_o - FA_o}{2}\right) + PMIDA_o$$

$$Q_E = \int_{t_o}^{t} \dot{Q} dt = \int_{t_o}^{t} F(t) C_c (T_{c,f}(t) - T_{c,o}) dt$$

Equation (5-2) (modified) wherein $R_i$ is the rate of reaction for reactions $Rx_1$, $Rx_2$ and $Rx_3$ above and $Q_{loss}$ is heat loss from the reactor system:

$$\frac{d C_p M(T - T_R)}{dt} = -\sum_{i=1}^{3} R_i \Delta H_{Rxi} - \dot{Q} - \dot{Q}_{loss}$$

For any initial time to (but not limited to literal $t_o$=0) the total heat removed via a heat exchanger through time t=

$$Q_E = \int_{t_o}^{t} \dot{Q} dt = \int_{t_o}^{t} F(t) C_c (T_{c,f}(t) - T_{c,o}) dt$$

Integrate Equation 5-2 (modified):

$$\int_{t_o}^{t} \frac{d C_p M(T - T_R)}{dt} dt = -\int_{t_o}^{t} \left(\sum R_i \Delta H_{Rxi}\right) dt - \int_{t_o}^{t} \dot{Q} dt - \int_{t_o}^{t} \dot{Q}_{loss} dt$$

At high conversion, the left side of this equation can be assumed approximately zero because at this point in the reaction, the reactor temperature is typically well-controlled and approximately constant. Moreover, in the last term on the right side of the equation, $Q_{loss}$ can be assumed approximately a constant for a given reactor system.

$$Q_E + Q_{loss}(t - t_o) = -\int_{t_o}^{t}\left(\sum R_i \Delta H_{Rxi}\right) dt$$

For the given reaction system (simplified with three reactions) the reactions can be rewritten:

$Rx_A = PMIDA + 1.5O_2 \rightarrow Gly + 2CO_2 + H_2O$ $\Delta H_A = \Delta H_{Rx1} + \Delta H_{Rx2} + \Delta H_{Rx3}$ $Rx_B = PMIDA + 1O_2 \rightarrow Gly + CO_2 + FA$ $\Delta H_B = \Delta H_{Rx1} + \Delta H_{Rx2}$ $Rx_C = PMIDA + 0.5O_2 \rightarrow Gly + CO_2 + FM$ $\Delta H_C = \Delta H_{Rx1}$ where:
$\Delta H_{Rx1}$ = exothermic heat of reaction for $Rx_1$
$\Delta H_{Rx2}$ = exothermic heat of reaction for $Rx_2$
$\Delta H_{Rx3}$ = exothermic heat of reaction for $Rx_3$ The extent of each the three reactions may be determined by measuring:

$\Delta FM$ and $\Delta FA$ $Heat_C = (FM - FM_0)\Delta H_c = (FM - FM_0)\Delta H_{Rx1}$ $Heat_B = (FA - FA_0)\Delta H_b = (FA - FA_0)(\Delta H_{Rx1} + \Delta H_{Rx2})$ $Heat_A = [(PMIDA_0 - PMIDA) - (FM - FM_0) - (FA - FA_0)]$
$(\Delta H_{Rx1} + \Delta H_{Rx2} + \Delta H_{Rx3})$ Therefore, $Q_E + \dot{Q}_{loss}(t - t_0) = -(Heat_A + Heat_B + Heat_C)$ $Q_E + \dot{Q}_{loss}(t - t_o) = (PMIDA - PMIDA_0)(\Delta H_{Rx1} + \Delta H_{Rx2} + \Delta H_{Rx3}) - (FM_0 - FM)(\Delta H_{Rx2} + \Delta H_{Rx3}) - (FA_0 - FA)(\Delta H_{Rx3})$ Based on the relationship set forth above, the residual PMIDA present at any given time subsequent to the base point can be determined and converted to a concentration. Likewise, those skilled in the art will understand that the same principles can be applied to estimate conversion and/or residual PMIDA content at any given location in a continuous oxidation reactor system downstream of the location from which the base point sample is taken.

A third approach uses reaction kinetics and thereby avoids dual measurement (i.e., FTIR+heat release or FTIR+cumulative $CO_2$) and so that just FTIR or HPLC can be used.

$$\frac{dPMIDA}{dt} = -k_{Rx1}[PMIDA] \quad (10\text{-}1)$$

$$\frac{dFM}{dt} = k_{Rx1}[PMIDA] - k_{Rx2}[FM] \quad (10\text{-}2)$$

$$= -\frac{dPMIDA}{dt} - k_{Rx2}[FM]$$

$$\frac{dFA}{dt} = k_{Rx2}[FM] - k_{Rx3}[FA] \quad (10\text{-}3)$$

where:
$k_{Rx1}$ = rate constant for conversion of PMIDA to glyphosate per $Rx_1$
$k_{Rx2}$ = rate constant for conversion of $CH_2O$ to formic acid per $Rx_2$
$k_{Rx3}$ = rate constant for conversion of formic acid to $CO_2$ per $Rx_3$ As those skilled in the art will understand, the rate constants as derived above actually constitute a composite of the actual rate constant and certain other variables, including mass transfer coefficients and dissolved oxygen content of the aqueous medium.

After the PMIDA concentration of the oxidation reaction solution has been measured analytically, e.g., by FTIR, at relatively high conversion in the non-zero order regime, e.g., 90% to 95%, the FTIR value is used to calculate $k_{Rx1}$ per equation 10-1. From the established value of $k_{Rx1}$ and the formaldehyde material balance based on further analytical data for formaldehyde, the value of $k_{Rx2}$ may be determined from equation 10-2; and from the established value of $k_{Rx3}$ and the material balance for formic acid based on further analytical data for formic acid, the value of $k_{Rx3}$ may be determined from equation 10-3. The values of $k_{Rx1}$, $k_{Rx2}$ and $k_{Rx3}$ may then be used to calculate a new PMIDA concentration. This iterative calculation is continued while the PMIDA concentration can be reliably measured using FTIR. Once the concentration of PMIDA can no longer be reliably measured using FTIR, the ratio of $k_{Rx2}/k_{Rx3}$ based on the previous calculations can be used to calculate $k_{Rx1}[PMIDA]$ by monitoring the concentration of formaldehyde. The ratio of $k_{Rx2}/k_{Rx3}$ may be modified in subsequent calculations based on operational experience and historical data, e.g., based on prior batches, to further refine this approach. This iterative calculation can be alternatively practiced using PMIDA concentration measured by HPLC.

Since the oxidation of PMIDA may be approximated as first order, the residual PMIDA content may also be inferred from the residual rate of reaction, as indicated by the instantaneous residual rate of heat generation, at the end of the batch, at the exit of a fixed bed reactor, or under the terminal conditions prevailing in the last of a series of CSTRs. In this regard, the inferences based on the progressively declining rate of reaction during non-zero order reaction are drawn substantially as is described above for the estimation of conversion and/or end point from oxygen consumption or $CO_2$ generation. Essentially, the residual PMIDA concentration is determinable from the instantaneous rate of heat generation as related to the mass of aqueous reaction medium contained in or flowing through the reaction zone. This method can be calibrated in the manner described above with respect to the oxygen consumption method, i.e., by estimation of the kinetic rate constant or function thereof from long term or short term historical data. Moreover, the estimate of the rate constant can be further updated in the manner described above, i.e., from the first derivative of the heat generation rate during the non-zero order reaction regime, i.e., the second derivative of cumulative heat generation. Data for updating such estimate can be generated by measuring the instantaneous rate of heat generation as a function of time under non-zero order reaction conditions, i.e., at different points in time toward the end of a batch reaction cycle, or at differing residence times under terminal conditions prevailing in the final stage of a continuous reaction system. As the catalyst ages and its activity declines, the effect on first order rate constants can be periodically re-calibrated by sampling the final stage of a continuous reaction system, or batch reactor near the end of the reaction cycle.

Under approximately first order reaction conditions, the reaction rate is approximately proportional to the product of residual PMIDA content and dissolved oxygen concentration. Where dissolved oxygen is maintained at a reasonable stable level, the reaction may be proportional to residual PMIDA concentration. Thus, where the value of the kinetic rate constant is known, e.g., from a series of samples taken at discrete intervals of time during the non-zero order reaction period of a recent batch, a recent series of batches, or during a discrete series of operations at differing flow rates in a continuous reaction system, residual PMIDA may also be estimated from the instantaneous rate of heat generation that is associated with the oxidation of PMIDA:

Continuous (steady-state) or batch with $$\frac{dT}{dt} \approx O$$

Assume:

$$R = k \cdot m(t)$$

m(t)=system mass of PMIDA

Substitute into equation 5-2 ($C_p$, M, $T_0$ constant)

$$C_p M \frac{dT}{dt} = -\Delta H_R k m(t) - \dot{Q}$$

Assume $$\frac{dT}{dt} \approx O$$

at end of reaction:

$$\dot{Q} = -\Delta H_R k \cdot m \quad (6\text{-}1)$$

$$m = \frac{\dot{Q}}{-\Delta H_R \cdot k} \quad (6\text{-}2)$$

The value of k is dependent on catalyst activity and, thus tends to decline over time. However, the value of k can be constantly updated by measuring both the rate of heat generation and the rate at which the rate of heat generation declines during the non-zero order reaction period of a batch reaction system. Similar information may be provided by operating at different residual times in the non-zero order zone within a continuous reaction system, e.g., the last of a series of CSTRs, or the zone near the exit of a plug flow reactor:

$$R = k \cdot m$$

for batch when $$\frac{dT}{dt} \approx O \quad (6\text{-}3)$$

$$\frac{dm}{dt} = -km = +\frac{\dot{Q}}{\Delta H_R}$$

$$\frac{d^2m}{dt^2} = -k\frac{dm}{dt} = \frac{\frac{dQ}{dt}}{\Delta H_R} \quad (6\text{-}4)$$

$$\frac{-k\dot{Q}}{\Delta H_R} = \frac{+\frac{d\dot{Q}}{dt}}{\Delta H_R}$$

$$k = \left(-\frac{d\dot{Q}}{dt}\right)\frac{1}{\dot{Q}} \quad (6\text{-}5)$$

An updated estimate of the kinetic rate constant, as obtained, for example, from a given PMIDA oxidation reaction batch, may be used in estimating residual PMIDA in a subsequent batch using the same catalyst mass under the same reaction conditions. In a series of continuous reaction zones, the updated rate constant, as based on sampling or inferred from the rate of decline in the rate of heat generation across the final reaction zone during a select period of operation, may be used in estimating conversions and controlling residence times and oxygen flow rates during other operations, such as: (i) conversion of PMIDA to glyphosate in the same reactor at a different point in real time; (ii) conversion of PMIDA to glyphosate in the same reactor at a different residence time; (iii) conversion of PMIDA to glyphosate in a different final back mixed reaction zone; and combinations thereof. Note that the mathematical principles for estimation of conversion and rate constant, as outlined above with respect to heat generation, are equally applicable to other methods for determining conversion, including oxygen consumption, $CO_2$ generation and various analytical methods.

Heat generation data may be used to project the conversion or reaction end point in the manner described above with respect to FTIR, but more particularly as described in connection with the oxygen consumption method. While FTIR provides a direct measure of PMIDA content, the oxygen consumption, carbon dioxide generation and heat generation methods all yield data which are a function of PMIDA content, but the nature of the function must be separately established. The description above with regard to oxygen consumption deals with this element of the method. Further in connection with the estimation or projection of conversion and end point by heat generation, operational data may also be used to estimate the order of reaction and/or the kinetic rate constant, again essentially in the manner described above with respect to FTIR, as modified according the description set forth above for the oxygen consumption method.

To compensate for oxidation of $C_1$ compounds in the differential heat generation method, residual formaldehyde and formic acid concentrations under terminal conditions can also be directly measured or estimated from historical data as described above with regard to the estimation of PMIDA conversion from oxygen consumption and/or $CO_2$ generation. Alternatively, as noted above, the measured cumulative heat generation can be adjusted for the effect of $C_1$ oxidation by estimating residual $C_1$ content from electrochemical oxidation data for $C_1$ compounds. Moreover, from historical operating data, the kinetic rate constants for oxidation of formaldehyde and formic acid may be a known or knowable function of the kinetic rate constant for oxidation of PMIDA, as each of these varies with changing catalyst activity and the oxidation/reduction potential of the aqueous medium.

Also as in the case of oxygen consumption and/or $CO_2$ generation, the conversions estimated from cumulative heat generation in a continuous reaction system may be adjusted by any difference in the molar rate at which PMIDA is introduced into the reaction system vs. the molar rate at which the sum of glyphosate and unreacted PMIDA are withdrawn therefrom.

Preferably, estimation of conversion by heat generation is further adjusted for various heat losses from the system, including conductive heat losses to the environment, sensible heat loss to the vent gas ($O_2$, $CO_2$ and any other inerts), and evaporative heat loss reflected by the water vapor, formaldehyde and formic acid content of the vent gas. To further refine the estimate obtained from cumulative or differential heat generation data, the estimate of the sum of the effects of environmental heat loss and heat loss to said vent gas from a given reaction batch in a particular reaction zone is adjusted by comparison of actual conversion data for a given period of operation to an estimate of conversion that had been computed for a previous batch as produced in said particular reaction zone. Similarly, the estimate for such losses from a continuous reactor for a particular period of operation can be adjusted by comparison with actual conversion data for the same period of operation at an earlier time.

Estimation of conversion from heat generation data may be used in combination with either or both of the oxygen consumption and carbon dioxide generation methods described hereinabove. As noted, it may also be used together with data from electrochemical oxidation, either for estimation of $C_1$ compounds alone, or for a corroborative estimate of PMIDA also. As stated above, the various methods of the invention can be used in various combinations to maximize the information obtained and enhance process control schemes. Such combinations may be particularly useful where one method is used to monitor the conversion of PMIDA and another method is used to evaluate the kinetics of the reaction or compensate for $C_1$ content. All combinations are permutations of these methods are contemplated because, as described above, all of them have the capability of providing useful data on conversion of PMIDA, kinetic rate constants and order of reaction. And all can be used either to detect or to project the end point of the reaction or the proper residence time to achieve a desired conversion.

Multiple combinations of these methods may be suitable for $C_1$ compensation. For example, FTIR or HPLC may provide a determination of formaldehyde and formic acid content sufficient to adjust an estimate of PMIDA content based on oxygen consumption, heat generation, electrochemical oxidation or carbon dioxide generation. The value of on-line FTIR for this purpose may be enhanced if the instrument is tuned specifically to follow the formaldehyde and formic acid concentrations. Moreover, non-dispersive i.r. can also be used to monitor $C_1$s. Additionally or alternatively, a stoichiometric comparison of cumulative oxygen consumption with cumulative $CO_2$ generation may provide a basis for estimating the fraction of formaldehyde and formic acid that are produced in the oxidation of PMIDA but not oxidized to $CO_2$. For this purpose, it may be useful to monitor the difference in instantaneous oxygen consumption and $CO_2$ generation, and integrate this difference over time to estimate the accumulation of $C_1$s and/or the destruction thereof. In a further alternative, select voltage electrochemical oxidation may be useful for determination of $C_1$s while conversion of PMIDA may be monitored by instantaneous heat generation, cumulative heat generation, instantaneous oxygen consumption, cumulative oxygen consumption, FTIR, HPLC, and/or carbon dioxide generation, optionally in combination with select voltage and/or select current electrochemical oxidation. Where oxygen consumption and/or carbon dioxide generation are used either as primary methods for monitoring PMIDA consumption, or in an auxiliary role for monitoring $C_1$s, the composition of the vent gas exiting the liquid phase is preferably monitored as described above with respect to detection of end point by vent gas $O_2$ or $CO_2$ content, e.g., by directing a sample of the liquid phase to a gas/liquid separator or by use of a probe which determines the content of nascent gas phase in the liquid phase. Where select voltage electrochemical oxidation is used to monitor PMIDA, PMIDA and $C_1$s, or $C_1$s alone, it may be periodically calibrated by assaying the reaction mixture, e.g., by HPLC.

Under certain conditions, time alone may function as a useful measure of conversion and/or end point, or may be used in combination with any one or any combination of the other methods described herein for the purpose. Where batch PMIDA and catalyst charge, or continuous reactor PMIDA and catalyst charge rate, can be precisely measured and reliably controlled, temperature, oxygen flow and agitation precisely and consistently controlled, successive batches or successive operations can be reasonably controlled based on assay of immediately preceding batches and measurement of reaction time. In such operations, it may be desirable to introduce the PMIDA charge from a weigh tank and provide positive shut-off valves or disconnect the charge line from the reactor after charging is complete. Timed reaction may be an attractive alternative where, e.g., a batch reactor is operated with a dedicated catalyst mass, i.e., a catalyst mass that is segregated from other catalyst masses that are used in the same or other reactors in a glyphosate manufacturing facility. If, for example, two separate catalyst masses are dedicated to a given reactor so that one is being used in the oxidation reaction while the other is being recovered by filtration, the reaction time for each batch (n) can be guided by the reaction time and assay of batch (n−2), after which the reaction time for batch (n+1) can be guided by reaction time and assay of batch (n−1), and so on. In a carefully controlled system, monitoring of total oxygen delivered to the reactor may be used as an alternative to timing the reaction, or as a cross-check against determination of conversion or end point by time alone. Note that, where oxygen input is monitored, it is also useful to monitor oxygen consumption, so that the oxygen consumption method described above provides a further cross-check against determination of conversion and/or end point based on time and/or cumulative oxygen flow.

The various methods of the invention for monitoring PMIDA content can be used in monitoring streams other than the product reaction solution obtained in a PMIDA oxidation reactor. For example, in response to PMIDA concentration in crystallization mother liquor streams such as, e.g., streams 129 and 131 of FIGS. 1 and 2, PMIDA purge streams, such as purge 133 of FIGS. 1 and 2, adjustments may be made to the conditions of operation of a crystallization process, the purge fraction, or the division and allocation of process streams for purposes of allocating unreacted PMIDA among plural glyphosate products. The methods of the invention may also be useful, for example, in monitoring the operation of an ion exchange system, and in particular for identifying breakthrough of chlorides or PMIDA from an ion exchange column whose duty is to remove them from a stream also comprising glyphosate as disclosed hereinabove.

Where the order of the oxidation reactions and the rate constants thereof, etc. are initially determined by laboratory experimentation, such data may be combined with exothermic heats of reaction, material balances, energy balances (including estimates of environmental heat losses and both sensible and latent heat losses to reaction gases), and other process parameters to generate a mathematical model predictive of conversion and end point as a function of the temperature, oxygen flow, dissolved oxygen, oxidation/reduction potential, agitation, feed composition and other process variables that may be imposed and/or measured in the field. Where the model is based on oxygen consumption, carbon dioxide generation, and/or heat consumption, it can and preferably does account for the impact of the oxidation of formaldehyde to formic acid and formic acid to carbon dioxide on these observed effects. Such an algorithm may integrate any number of the end point and conversion methods described herein, including not only FTIR, but also $O_2$ consumption, $CO_2$ generation, vent gas analyses, dissolved oxygen, etc. From a select combination of such data, a virtual reaction model may be established from which end points can be projected with great accuracy. Moreover, such projections may utilize FTIR or other measurements that are taken, for example, when 10% or more of PMIDA feed remains unreacted and a pseudo zero order reaction, still prevails, e.g., in the next to last of a series of CSTRs or at a point in a batch cycle when reaction rate remains directly proportional to dissolved oxygen concentration independently of PMIDA content. A control system that is programmed with such a model may function to adjust independent variables to consistently achieve a target PMIDA concentration in the product reaction solution. For example, in a batch reaction system, the point at which oxygen flow is ramped down or terminated can be adjusted in response to such a predictive model. In a continuous reaction system, feed rates may be adjusted to alter residence times in order to achieve a desired conversion and target exit PMIDA content. In either batch or continuous operation, a controller programmed with such an algorithm may be used to adjust temperature, oxygen flow rates, oxygen pressure, intensity of agitation, etc.

In accordance with the invention, the algorithm may be updated by computer evaluation of actual plant operating data, including a combination of actual operating conditions and precise laboratory analyses of process samples that are taken routinely in the course of operations. Such computer evaluation and adjustment may be directly programmed into the operational end point estimation and control system to further refine the virtual process model that is used in further and ongoing end point projection.

A programmed control scheme that incorporates a virtual model of the reactor, but which may also integrate other considerations such as market factors is described below.

Programmed Control Scheme

The present invention contemplates the use of essentially all combinations and permutations of the various measures that are described hereinabove for reducing the PMIDA content of a glyphosate product. The invention further contemplates the use of one or more of the above-described schemes for monitoring PMIDA conversion, and identifying a reaction end point based on residual PMIDA content. In this regard, the programmed control scheme may comprise the programmed end point and oxygen flow control models that are illustrated in FIGS. 10 and 14, but is not limited thereto. FIG. 14 provides closed loop control of conversion by regulating oxygen flow in response to residual PMIDA content. In some instances, this may suffice for satisfactory control. In other instances, it may not be technically feasible or economically attractive to achieve a target PMIDA concentration by resort solely to increased oxygen flow rate, or solely to increased purge, or solely to any other single process control stratagem. Although certain process modifications such as ion exchange, where justified, may be quite sufficient to achieve any desired PMIDA level, there can still be advantages in adopting ion exchange in combination with other operational variations.

In practicing the various methods of the invention, operational stability, economic optimization, product and emission specification and/or other advantages and constraints may be met or achieved by a programmed control scheme under which a combination of various measures such as increased oxygen flow, purge adjustment, allocation of PMIDA among plural product forms, ion exchange conditions, process flows, reactor and crystallizer temperatures, reactor and crystallizer pressures, etc., may be monitored and controlled at values which achieve a target PMIDA specification in one or more product forms according to an optimal or otherwise desirable operational mode. In this connection, it will be understood that what is referred to as the process control system 403 in FIG. 14 may be programmed to integrate input signals other than PMIDA content and oxygen flow and generate output signals other than oxygen flow set points. The input signals may include, e.g., reaction temperatures, oxygen flow, oxygen pressure, catalyst concentration, catalyst age and activity, heat generation dissolved oxygen, oxygen content of vent gas, $CO_2$ content of vent gas, ORP and various scheduling parameters, in addition to signals from one or more of the methods described above for monitoring PMIDA conversion and/or identifying oxidation reaction end points. In accordance with such a control scheme, signals conveying the prevailing values of various parameters and the control set points for the control loops for such parameters may be transmitted to a programmed controller which, in response to these inputs, may generate output signals to adjust the various set points according to an algorithm inscribed in controller software. For example, the algorithm may be adapted to achieve a target PMIDA content in a specified glyphosate product form at minimum cost, and/or at maximum throughput, and/or to meet other product specifications, and/or to conform to emission standards, etc.

Such a program may be periodically adjusted as necessary to reflect changes in raw material prices, product demand, production scheduling, environmental conditions, etc.

Although the various methods of the invention have been described above with respect to the catalytic oxidation of PMIDA to glyphosate, the methods are effective in other oxidation processes. For example, PMIDA conversion and end point detection can be provided in the oxidation of PMIDA to N-(phosphonomethyl)iminodiacetic acid-N-oxide by reaction with a peroxide compound in the presence of a metal catalyst as described in U.S. Pat. Nos. 5,043,475, 5,077,431 and/or 5,095,140. Each of the various methods described herein can be applied to the peroxide oxidation process. FTIR and HPLC analyses operate on the same principles as for catalytic oxidation to glyphosate. Reaction material balances for oxygen consumption and $CO_2$ generation are different but known, as are energy balances for heat generation. For electrochemical methods, the oxidation voltage for oxidation of PMIDA to N-(phosphonomethyl)iminodiacetic acid-N-oxide may not be known but can be experimentally determined by methods known to the art.

Glyphosate Product

By implementation of one or more of the process modifications and stratagems as described above, a manufactured glyphosate product may be recovered and removed from the process in a desired form with a PMIDA content of less than, 6,000 ppm, 5,000 ppm, 4,000 ppm, 3,000 ppm, 2,000 ppm, 1,000 ppm, 600 ppm or even significantly lower. A glyphosate product of such low PMIDA level can be produced, for example, in the form of a solid crystalline glyphosate acid, or in the form of an aqueous concentrate of glyphosate salt, such as a potassium or isopropylamine salt having a glyphosate content of at least about 360 gpl, a.e., preferably at least about 500 gpl, a.e., more preferably at least about 600 gpl, a.e.

Glyphosate having a relatively low PMIDA content, e.g., not greater than about 0.45 wt. % acid equivalent on a glyphosate, a.e., basis, can be prepared by any of a variety of manufacturing processes. Significant commercial advantages result from the preparation of glyphosate by a process comprising the catalytic oxidation of a PMIDA substrate as described in detail hereinabove. Glyphosate obtained in this manner has a very low glyphosine content, typically less than about 0.010 wt. % acid equivalent on a glyphosate a.e. basis. It generally has a small but acceptable glycine content, i.e., at least about 0.02 wt. % acid equivalent as also computed on a glyphosate, a.e., basis. PMIDA-derived glyphosate product may also include small, but acceptable concentrations of a number of other by-products and impurities. These may include for example: iminodiacetic acid or salt thereof (IDA) in a concentration of at least about 0.02 wt. % acid equivalent on a glyphosate, a.e., basis; N-methyl glyphosate or a salt thereof (NMG) in a concentration of at least about 0.01 wt. % on a glyphosate, a.e., basis; N-formylglyphosate or a salt thereof (NFG) in a concentration of at least about 0.010 wt. % acid equivalent on a glyphosate, a.e., basis; iminobis (methylenephosphonic acid) or a salt thereof (iminobis) in a concentration of at least about 0.010 wt. % acid equivalent on a glyphosate, a.e., basis; and N-methylaminomethylphosphonic acid (MAMPA) or a salt thereof in a concentration of at least about 0.010 wt. % acid equivalent on a glyphosate, a.e., basis.

These relative proportions generally apply regardless of the form of the glyphosate product, i.e., regardless of whether it is in the form of solid state glyphosate acid or a concentrated aqueous liquid solution comprising a glyphosate salt such as, for example, a potassium, isopropylamine, monoammonium or diammonium salt. Preferred aqueous concentrates comprise at least about 360 grams per liter glyphosate on an acid equivalent basis, with proportionate minor concentrations of the common by-products and impurities as listed above.

Further detailed limits and ranges for IDA, NMG, AMPA, NFG, iminobis, and MAMPA are set out below. All are expressed on an acid equivalent basis relative to glyphosate, a.e.

More typically, the IDA content may be between about 0.02 wt. % and about 1.5 wt. %, e.g., between about 0.05 wt. % and about 1.0 wt. %, on a glyphosate a.e. basis. Preferably, the IDA content is not greater than about 0.58 wt. %, not greater than about 0.55 wt. %, or not greater than about 0.50 wt. % on the same basis. In most operations, the product obtained has an IDA content between about 0.1 and about 0.58 wt. %, between about 0.1 and about 0.55 wt. %, between about 0.02 and about 0.55 wt. %, or between about 0.1 and about 0.50 wt. %.

Generally, the NMG content is between about 0.02 and about 1.5 wt. %, for example, between about 0.02 and about 1.0 wt. %, or between about 0.070 and about 1 wt. % on a glyphosate, a.e., basis. Preferably, the NMG content is not greater than about 0.55 wt. % or not greater than about 0.50 wt. %.

The glyphosate product also typically contains aminomethylphosphonic acid or a salt thereof (AMPA) in a concentration that may be incrementally higher than that of glyphosate products which have relatively higher residual PMIDA content. For example, the AMPA content may range between about 0.15 and about 2 wt. %, more typically between about 0.2 and about 1.5 wt. % aminomethylphosphonic acid or a salt thereof on a glyphosate, a.e., basis. In most instances, the AMPA content is at least about 0.30 wt. % on the same basis.

The NFG content is ordinarily between about 0.01 and about 1.5 wt. %, e.g., between about 0.03 and about 1.0 wt. %, more typically between about 0.010 and about 0.70 wt. % on a glyphosate, a.e., basis. It is generally preferred that the NFG content be not greater than about 0.70 wt. %, not greater than about 0.60 wt. %, not greater than about 0.50 wt. %, not greater than about 0.40 wt. %, or not greater than about 0.30 wt. % on the same basis.

Typically the iminobis content of the glyphosate product is between about 0.1 and about 1.5 wt. %, e.g., between about 0.2 and about 1.0 wt. % on a glyphosate, a.e., basis. Preferably, the iminobis content is not greater than about 0.8 wt. % iminobis(methylenephosphonic acid), normally between about 0.2 and about 0.8 wt. % on the same basis.

The MAMPA content is ordinarily between 0.1 about and about 2 wt. %, e.g., between 0.15 about and about 1.0 wt. % on a glyphosate, a.e., basis. Most typically, the MAMPA content is at least about 0.25 wt. % MAMPA on the same basis. Most PMIDA-derived product comprises between about 0.25 and about 0.6 wt. % MAMPA.

Although the typical levels of these various impurities and by-products are inconsequential so far as the function, use and handling of the glyphosate product is concerned, they serve as markers which distinguish a product produced by catalytic oxidation of PMIDA from glyphosate product as produced by other processes. The presence of such impurities and by-products in the upper portions of the above described ranges have some measurable impact on manufacturing process yields, and thus on product manufacturing cost.

To provide a reliable commercial source of glyphosate having a relatively low residual PMIDA content, it is necessary to either operate the manufacturing process on a sustained basis to consistently produce glyphosate product of low PMIDA content, or to segregate product from designated operations in order to accumulate commercial quantities of low PMIDA product.

Although glyphosate products having a low PMIDA content have been incidentally produced on a transient basis during startup of a manufacturing facility for the catalytic oxidation of PMIDA to glyphosate, or in operation well below rated capacity, the processes of the prior art have not been effective for the preparation of a low PMIDA glyphosate product on a continuing basis during steady state operations at or near capacity. Thus, each of the various glyphosate products of the invention encompasses a lot, run, shipment, segregate, campaign or supply of glyphosate product as produced by a process capable of maintaining a low PMIDA content on a continuing basis. According to the present invention, such a lot, run, shipment, campaign, segregate or supply comprises a quantity of solid state glyphosate acid, or concentrated aqueous solution of glyphosate salt, comprising at least 1500 metric tons, preferably at least about 3000 metric tons, glyphosate on a glyphosate a.e. basis.

For purposes of this invention, a "lot" may be considered a designated quantity of glyphosate product that is produced under substantially consistent process conditions in a particular manufacturing facility during a defined period of operations or over a designated period of time. Production of the lot may be interrupted for production of other glyphosate product or non-glyphosate product, or purge of impurities from the process, but not otherwise by catalyst replacement, turnaround or startup operations. Glyphosate may be produced according to various different processes, some of which (e.g., a process comprising the aqueous phase catalytic oxidation of PMIDA) can be conducted in either a batch or continuous mode in the oxidation step and/or or in the recovery of glyphosate by crystallization thereof from an aqueous medium. With reference to a process comprising a batch reaction and/or batch glyphosate crystallization operation, it is understood that a lot may comprise the product of a plurality of batches.

A "run" is quantity of glyphosate product made in a particular manufacturing facility in continuing or consecutive operations over a designated period without interruption for maintenance, catalyst replacement, or catalyst loading. It may include both startup and steady state operations. With reference to a batch reaction and/or batch glyphosate crystallization operation, it is understood that a run may comprise the product of a plurality of batches.

A "campaign" is a series of runs conducted over an identifiable period of time during which the runs may be interrupted by other runs not part of the campaign or by purge of impurities, or for maintenance, but not by turnaround or catalyst replacement. No more than one of the runs may include startup operations; provided, however, that more than one of the runs may comprise operation at a rate more than 30% below established capacity. Compare the description of startup operations as set out hereinbelow.

A "shipment" is a commercial quantity of glyphosate product transported to a particular customer or user in either a single unit, single combination of units, consecutive units, or consecutive combinations of units without interruption by transport of a commercial quantity of a glyphosate product of materially different average PMIDA content on a glyphosate, a.e., basis to the same user or customer. A materially different PMIDA content is PMIDA content that is either more than 0.15 wt. % higher than the average PMIDA content of the shipment on a glyphosate, a.e., basis, more than 35% higher than the average PMIDA content of the shipment on a PMIDA basis, or is above 4500 ppm on a glyphosate a.e. basis.

A "supply" is a series of shipments that may be interrupted by other shipments of glyphosate product to other customers or users.

A "segregate" is a quantity of glyphosate product that is isolated from other glyphosate product produced in the same manufacturing facility over the same period of time (i.e., the time during which the segregate is produced). The segregate may be produced in different runs, and may be allocated among different shipments or different supplies.

Startup operations are operations that are conducted in a manufacturing facility in which glyphosate product has not previously been produced, or directly following interruption of the production of glyphosate product and removal of a substantial fraction of the inventory of process liquids contained in process equipment, with the effect of lowering the total inventory of by-products and impurities in the process facility by at least 25 wt. %. Impurities and by-products include PMIDA, IDA, AMPA, NMG, NFG, iminobis(methylenephosphonic acid), MAMPA, formic acid, NMIDA, glycine and glyphosine. For purposes of this invention, operations at a rate that is more than 30% below currently established capacity of a manufacturing facility is also deemed within the ambit of startup operations.

Following are Examples presented to illustrate the present invention and are not intended to limit the scope of this invention. The examples will permit better understanding of the invention and perception of its advantages and certain variations of execution.

Example 1

Use of Dual Probe Electrode in Electrochemical Oxidation Method for End Point Determination in Catalytic Batch Oxidation of PMIDA to Glyphosate To a 1 liter autoclave pressure vessel was charged 11.4 grams of 99% purity PMIDA. 1.4 grams of fresh activated carbon catalyst was added, along with 420 grams of water. The pressure vessel was closed, and agitation at 300 rpm was started. The dual probe electrode was mounted in the bottom of this vessel. Oxygen gas was introduced subsurface into the vessel, and the pressure was allowed to rise to 60 psig. Excess oxygen and other off gases were allowed to vent to atmosphere. The reaction mass self heated to 90° C., and was maintained at this temperature by heat removal through a chilled water cooling coil. The progress of the reaction was followed by tracking the voltage response. After about 30 minutes, the voltage began to rise, indicating the disappearance of PMIDA. After a voltage rise of 0.2 volts, the reaction was stopped. The glyphosate solution was pumped out of the autoclave through a fritted filter, leaving the carbon catalyst behind. The filtrate solution was cooled, and the glyphosate allowed to crystallize. Residual PMIDA was determined to be very low.

Example 2

Use of Cumulative Heat and $CO_2$ Gas Evolution to Track the Progress of the Reaction of PMIDA to Glyphosate The referenced chemical process takes place in two steps. In the first, PMIDA is oxidized to PMIDA N-oxide with hydrogen peroxide in the presence of a tungsten catalyst. This PMIDA N-oxide intermediate material is isolated, and then catalytically decomposed to glyphosate accompanied by an equimolar generation of $CO_2$. This catalytic decomposition is highly exothermic, and is controlled by the rate of vanadium sulfate catalyst addition. If the catalyst addition is too fast, the reaction can overheat and switch to an uncontrolled thermal decomposition. The rate of $CO_2$ evolution is used to track the reaction rate and control catalyst addition. The cumulative heat generation in this step is used to determine when the reaction reaches 90% completion, at which point the catalyst addition is stopped.

Into a 16000 liter vessel was added 2100 liters of water, 1600 kg of PMIDA and 4 kg of $Na_2WO_4$ catalyst. This slurry was heated to 60° C. 394 liters of $H_2O_2$ was slowly added to form the PMIDA N-oxide. Excess peroxide was destroyed with addition of sodium metabisulfite. The intermediate (PMIDA N-oxide) material slurry was pumped to a 12000 liter vessel, where 3 kg of 33% $VOSO_4$ was slowly added. $CO_2$ evolution was closely monitored to track reaction rate, and cumulative heat was used to track the % completion of the reaction. If $CO_2$ evolution exceeded 2000 liters per minute, the rate of catalyst addition was slowed or stopped until the $CO_2$ evolution rate dropped below 2000 liters per minutes. Reaction heat was totalized until about 290,000 kCal of heat was removed (90% completion). At this point, the catalyst addition was stopped, and the reaction slurry cooled. Solid glyphosate was separated by centrifugation. PMIDA and PMIDA N-oxide levels were found to be very low.

In view of the above, it will be seen that the several objects of the invention are achieved and other advantageous results attained.

As various changes could be made in the above description without departing from the scope of the invention, it is intended that all matter contained in the above description or shown in the accompanying drawings shall be interpreted as illustrative and not in a limiting sense.

When introducing elements of the present invention or the preferred embodiments thereof, the articles "a", "an", "the", and "said" are intended to mean that there are one or more of the elements. The terms "comprising", "including," and "having" are intended to be inclusive and mean that there may be additional elements other than the listed elements.

What is claimed is:

1. A method for monitoring or detecting the conversion of N-phosphonomethyl)iminodiacetic acid to N-phosphonomethyl)glycine or another intermediate for N-phosphonomethyl)glycine in the course of the catalytic oxidation of N-(phosphonomethyl)iminodiacetic acid in an aqueous medium, the method comprising:
   monitoring the aminomethylphosphonic acid content of said aqueous medium for aminomethylphosphonic concentration and/or rate of aminomethylphosphonic acid production data; and
   determining the conversion or identifying an end point of the reaction based on the aminomethylphosphonic acid content of said medium, wherein the conversion or end point is identified based on historical data correlating the rate of change in said aminomethylphosphonic acid content data with the conversion or residual N-(phosphonomethyl) iminodiacetic acid content of the aqueous liquid medium, wherein the conversion or end point is determined after at least 95% of the N-(phosphonomethyl) iminodiacetic acid has been converted.

2. A method as set forth in claim 1 wherein conversion or end point is determined as a function of absolute concentration of aminomethylphosphonic acid in the aqueous medium as attained after a minimum batch reaction time or a minimum residence time sufficient so that, under the conditions prevailing in the reaction zone, there is a unique correlation between the aminomethylphosphonic acid content of the medium vs. conversion and/or residual N-(phosphonomethyl)iminodiacetic acid content in the course of further reaction subsequent to said minimum reaction time or residence time.

3. A method as set forth in claim 1 wherein conversion or end point is determined as a function of absolute aminomethylphosphonic acid content of the aqueous medium as attained in a batch reaction or in a continuous reaction zone during non-zero order conversion of N-(phosphonomethyl)iminodiacetic acid to N-(phosphonomethyl)glycine or said another intermediate.

4. A method as set forth in claim 1 wherein conversion or end point is determined as a function of absolute concentration of aminomethylphosphonic acid in the aqueous medium as attained during a period a batch reaction, or in a continuous reaction zone.

5. A method as set forth in claim 1 wherein said historical data comprises analytical data or operational data obtained from laboratory and/or industrial oxidation reactions.

6. A method as set forth in claim 1 comprising monitoring the rate of change of the aminomethylphosphonic acid content of said aqueous medium as a function of batch reaction time or continuous oxidation residence time.

7. A method as set forth in claim 5 comprising monitoring the rate of change of aminomethylphosphonic acid content of the aqueous medium after a minimum batch reaction time or a minimum residence time sufficient so that, under the conditions prevailing in the reaction zone, there is a unique correlation between rate of change of the aminomethylphosphonic acid content of the aqueous medium vs. conversion and/or residual N-(phosphonomethyl)iminodiacetic acid content in the course of further reaction subsequent to said minimum reaction time or residence time.

8. A method as set forth in claim 6 wherein a desired conversion or end point is identified based on historical data correlating the rate of change in the aminomethylphosphonic acid content of the aqueous medium with the conversion or residual N-(phosphonomethyl)iminodiacetic acid content of the aqueous liquid medium.

9. A method as set forth in claim 8 wherein said historical data comprises analytical data or operational data obtained from laboratory and/or industrial oxidation reactions.

10. A method as set forth in claim 1 comprising monitoring the aminomethylphosphonic acid content of the aqueous medium during non-zero order conversion of N-(phosphonomethyl)iminodiacetic acid to N-(phosphonomethyl)glycine or said another intermediate.

* * * * *